(12) United States Patent
Okano et al.

(10) Patent No.: US 9,862,774 B2
(45) Date of Patent: Jan. 9, 2018

(54) PHARMACEUTICAL COMPOSITION FOR TREATMENT AND/OR PREVENTION OF CANCER

(71) Applicant: TORAY INDUSTRIES, INC., Tokyo (JP)

(72) Inventors: Fumiyoshi Okano, Kanagawa (JP); Takanori Saito, Kanagawa (JP); Yoshitaka Minamida, Kanagawa (JP); Takayoshi Ido, Kanagawa (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 14/910,878

(22) PCT Filed: Aug. 8, 2014

(86) PCT No.: PCT/JP2014/071094
§ 371 (c)(1),
(2) Date: Feb. 8, 2016

(87) PCT Pub. No.: WO2015/020212
PCT Pub. Date: Feb. 12, 2015

(65) Prior Publication Data
US 2016/0297889 A1 Oct. 13, 2016

(30) Foreign Application Priority Data
Aug. 9, 2013 (JP) ................................. 2013-166164

(51) Int. Cl.
| C07K 16/30 | (2006.01) |
| C07K 16/28 | (2006.01) |
| A61K 39/395 | (2006.01) |
| A61K 45/06 | (2006.01) |
| A61K 47/68 | (2017.01) |
| A61K 39/00 | (2006.01) |

(52) U.S. Cl.
CPC ........ *C07K 16/30* (2013.01); *A61K 39/39558* (2013.01); *A61K 45/06* (2013.01); *A61K 47/6851* (2017.08); *C07K 16/28* (2013.01); *C07K 16/303* (2013.01); *C07K 16/3015* (2013.01); *C07K 16/3023* (2013.01); *C07K 16/3038* (2013.01); *C07K 16/3046* (2013.01); *C07K 16/3053* (2013.01); *C07K 16/3061* (2013.01); *C07K 16/3069* (2013.01); *A61K 2039/505* (2013.01); *C07K 2317/24* (2013.01); *C07K 2317/41* (2013.01); *C07K 2317/52* (2013.01); *C07K 2317/56* (2013.01); *C07K 2317/565* (2013.01); *C07K 2317/732* (2013.01)

(58) Field of Classification Search
CPC . C07K 16/30; C07K 16/3015–16/3069; C07K 16/461–16/467; A61K 39/395; A61K 39/39558
See application file for complete search history.

(56) References Cited

U.S. PATENT DOCUMENTS

| 5,698,396 A | 12/1997 | Pfreundschuh |
| 6,335,170 B1 | 1/2002 | Orntoft |
| 6,444,425 B1 | 9/2002 | Reed et al. |
| 7,449,184 B2 | 11/2008 | Allison et al. |
| 7,485,302 B2 | 2/2009 | Adams et al. |
| 7,745,391 B2 | 6/2010 | Mintz et al. |
| 8,211,634 B2 | 7/2012 | Depinho et al. |
| 8,709,418 B2 | 4/2014 | Okano et al. |
| 8,828,398 B2 | 9/2014 | Kobayashi et al. |
| 8,911,740 B2 | 12/2014 | Saito et al. |
| 8,937,160 B2 | 1/2015 | Kobayashi et al. |
| 9,115,200 B2 | 8/2015 | Okano et al. |
| 9,175,074 B2 | 11/2015 | Okano et al. |
| 9,180,187 B2 | 11/2015 | Ido et al. |
| 9,180,188 B2 | 11/2015 | Kobayashi et al. |
| 9,181,334 B2 | 11/2015 | Kobayashi et al. |
| 9,181,348 B2 | 11/2015 | Kobayashi et al. |

(Continued)

FOREIGN PATENT DOCUMENTS

| CN | 1705676 A | 12/2005 |
| CN | 101120252 A | 2/2008 |
| CN | 101189516 A | 5/2008 |
| CN | 101836116 A | 9/2010 |
| CN | 102170907 A | 8/2011 |

(Continued)

OTHER PUBLICATIONS

Non-Final Office Action dated May 19, 2016, in U.S. Appl. No. 14/415,090.
Non-Final Office Action dated May 19, 2016, in U.S. Appl. No. 14/415,520.
Russian Decision on Grant for Russian Application No. 2012137504/10, dated Jun. 22, 2016, with an English translation.
Russian Office Action for Russian Application No. 2014138041/10, dated Jul. 5, 2016, with an English translation.

(Continued)

*Primary Examiner* — Jessica H Roark
(74) *Attorney, Agent, or Firm* — Birch, Stewart, Kolasch & Birch, LLP

(57) ABSTRACT

It is intended to provide a CAPRIN-1-targeting antibody superior in antitumor activity to conventional antibodies, and use thereof as a therapeutic and/or preventive agent for a cancer. The present invention provides an antibody targeting a CAPRIN-1 polypeptide specifically expressed on the surface of cancer cells, and use of the antibody as a therapeutic and/or preventive agent for a cancer. The present invention provides an antibody which comprises a heavy chain variable region comprising complementarity-determining regions of SEQ ID NOs: 1, 2, and 3 and a light chain variable region comprising complementarity-determining regions of SEQ ID NOs: 4, 5, and 6 and has immunological reactivity with a CAPRIN-1 protein, or a fragment thereof, and a pharmaceutical composition for the treatment and/or prevention of a cancer, comprising this antibody or fragment as an active ingredient.

24 Claims, No Drawings

(56) References Cited

U.S. PATENT DOCUMENTS

| | | |
|---|---|---|
| 9,260,513 B2 | 2/2016 | Kobayashi et al. |
| 9,266,958 B2 | 2/2016 | Kobayashi et al. |
| 9,273,128 B2 | 3/2016 | Okano et al. |
| 9,273,130 B2 | 3/2016 | Kobayashi et al. |
| 9,409,993 B2 | 8/2016 | Minamida et al. |
| 9,416,191 B2 | 8/2016 | Kobayashi et al. |
| 9,416,193 B2 | 8/2016 | Saito et al. |
| 9,428,581 B2 | 8/2016 | Saito et al. |
| 9,573,993 B2 | 2/2017 | Okano et al. |
| 2002/0006404 A1 | 1/2002 | Hanna et al. |
| 2003/0118599 A1 | 6/2003 | Algate et al. |
| 2003/0190640 A1 | 10/2003 | Faris et al. |
| 2004/0029114 A1 | 2/2004 | Mack et al. |
| 2004/0236091 A1 | 11/2004 | Chicz et al. |
| 2004/0258678 A1 | 12/2004 | Bodary et al. |
| 2005/0003390 A1 | 1/2005 | Axenovich et al. |
| 2005/0032113 A1 | 2/2005 | Tanaka et al. |
| 2005/0129690 A1 | 6/2005 | Bowdish et al. |
| 2005/0244413 A1 | 11/2005 | Adolf et al. |
| 2006/0019256 A1 | 1/2006 | Clarke et al. |
| 2006/0069054 A1 | 3/2006 | Houghton et al. |
| 2006/0275305 A1 | 12/2006 | Bryant |
| 2007/0048301 A1 | 3/2007 | Bodary-Winter et al. |
| 2007/0083334 A1 | 4/2007 | Mintz et al. |
| 2007/0154931 A1 | 7/2007 | Radich et al. |
| 2007/0264253 A1 | 11/2007 | Liu et al. |
| 2008/0075722 A1 | 3/2008 | DePinho et al. |
| 2008/0107668 A1 | 5/2008 | Philip et al. |
| 2008/0161293 A1 | 7/2008 | Yoshinaga et al. |
| 2008/0306018 A1 | 12/2008 | Croce et al. |
| 2010/0068724 A1 | 3/2010 | Fung et al. |
| 2011/0123492 A1 | 5/2011 | Okano et al. |
| 2011/0136121 A1 | 6/2011 | Okano et al. |
| 2011/0189700 A1 | 8/2011 | Moses et al. |
| 2011/0256144 A1 | 10/2011 | Okano et al. |
| 2012/0171699 A1 | 7/2012 | Goodman et al. |
| 2012/0214975 A1 | 8/2012 | Sandig et al. |
| 2012/0294860 A1 | 11/2012 | Ido et al. |
| 2012/0301471 A1 | 11/2012 | Kobayashi et al. |
| 2012/0301476 A1 | 11/2012 | Okano et al. |
| 2012/0321641 A1 | 12/2012 | Okano et al. |
| 2013/0045210 A1 | 2/2013 | Kobayashi et al. |
| 2013/0071398 A1 | 3/2013 | Saito et al. |
| 2014/0154261 A1 | 6/2014 | Okano et al. |
| 2014/0178373 A1 | 6/2014 | Kobayashi et al. |
| 2014/0179558 A1 | 6/2014 | Ido et al. |
| 2014/0186359 A1 | 7/2014 | Okano et al. |
| 2014/0193434 A1 | 7/2014 | Kobayashi et al. |
| 2014/0199311 A1 | 7/2014 | Kobayashi et al. |
| 2014/0308283 A1 | 10/2014 | Minamida et al. |
| 2015/0004171 A1 | 1/2015 | Kobayashi et al. |
| 2015/0017172 A1 | 1/2015 | Kobayashi et al. |
| 2015/0044221 A1 | 2/2015 | Kobayashi et al. |
| 2015/0050283 A1 | 2/2015 | Okano et al. |
| 2015/0185222 A1 | 7/2015 | Ido et al. |
| 2015/0198603 A1 | 7/2015 | Ido et al. |
| 2015/0218285 A1 | 8/2015 | Saito et al. |
| 2015/0299314 A1 | 10/2015 | Saito et al. |
| 2016/0297889 A1 | 10/2016 | Okano et al. |

FOREIGN PATENT DOCUMENTS

| | | |
|---|---|---|
| CN | 102171570 A | 8/2011 |
| EP | 2207037 A1 | 7/2010 |
| EP | 2322221 A1 | 5/2011 |
| EP | 2325648 A1 | 5/2011 |
| EP | 2 532 366 A1 | 12/2012 |
| EP | 2 532 680 A1 | 12/2012 |
| EP | 2532367 A1 | 12/2012 |
| EP | 2532743 A1 | 12/2012 |
| EP | 2740794 A1 | 8/2014 |
| EP | 2832365 A1 | 2/2015 |
| EP | 2832368 A1 | 2/2015 |
| JP | 2002-540790 A | 12/2002 |
| JP | 2003-528587 A | 9/2003 |
| JP | 2006-318040 A | 11/2006 |
| JP | 2013-502205 A | 1/2013 |
| JP | 2013-505028 A | 2/2013 |
| RU | 2 161 042 C2 | 12/2000 |
| RU | 2234942 C2 | 8/2004 |
| RU | 2244720 C2 | 1/2005 |
| RU | 2006137060 A | 4/2006 |
| RU | 2297241 C2 | 4/2007 |
| RU | 2306952 C2 | 9/2007 |
| RU | 2319709 C2 | 3/2008 |
| RU | 2 391 982 C2 | 6/2010 |
| RU | 2012137503 A | 3/2014 |
| RU | 2012137505 A | 3/2014 |
| WO | WO 96/09551 A1 | 3/1996 |
| WO | WO 00/04149 A2 | 1/2000 |
| WO | WO 00/05266 A1 | 2/2000 |
| WO | WO 00/60077 A2 | 10/2000 |
| WO | WO 01/32910 A2 | 5/2001 |
| WO | WO 01/72295 A2 | 10/2001 |
| WO | WO 02/078524 A2 | 10/2002 |
| WO | WO 02/083070 A2 | 10/2002 |
| WO | WO 02/092001 A2 | 11/2002 |
| WO | WO 03/007889 A2 | 1/2003 |
| WO | WO 2004/076682 A2 | 9/2004 |
| WO | WO 2004/097051 A2 | 11/2004 |
| WO | WO 2005/007830 A2 | 1/2005 |
| WO | WO 2005/100998 A2 | 10/2005 |
| WO | WO 2005/116076 A2 | 12/2005 |
| WO | WO 2006/002378 A2 | 1/2006 |
| WO | WO 2007/150077 A2 | 12/2007 |
| WO | WO 2008/031041 A2 | 3/2008 |
| WO | WO 2008/059252 A2 | 5/2008 |
| WO | WO 2008/073162 A2 | 6/2008 |
| WO | WO 2008/088583 A2 | 7/2008 |
| WO | WO 2009/113742 A2 | 9/2009 |
| WO | WO 2009/117277 A2 | 9/2009 |
| WO | WO 2010/016525 A1 | 2/2010 |
| WO | WO 2010/016526 A1 | 2/2010 |
| WO | WO 2010/016527 A1 | 2/2010 |
| WO | WO 2011/096517 A1 | 8/2011 |
| WO | WO 2011/096519 A1 | 8/2011 |
| WO | WO 2011/096528 A1 | 8/2011 |
| WO | WO 2011/096533 A1 | 8/2011 |
| WO | WO 2011/096534 A1 | 8/2011 |
| WO | WO 2011/098535 A1 | 8/2011 |
| WO | WO 2012/005550 A2 | 1/2012 |
| WO | WO 2012/013609 A1 | 2/2012 |
| WO | WO 2013/018885 A1 | 2/2013 |
| WO | WO 2013/018886 A1 | 2/2013 |
| WO | WO 2013/018894 A1 | 2/2013 |
| WO | WO 2013/147176 A1 | 10/2013 |
| WO | WO 2013/147189 A1 | 10/2013 |

OTHER PUBLICATIONS

Akiyoshi, "Cancer Vaccine Therapy Using Peptides Derived from Tumor-Rejection Antigens," Jpn J Cancer Chemother., vol. 24, No. 5, Mar. 1997, pp. 511-519, with English Abstract (p. 519).

Australian Patent Examination Report No. 1, dated Oct. 14, 2014, for Australian Application No. 2009278387.

Balmaña et al., "BRCA in breast cancer: ESMO Clinical Recommendations," Annals of Oncology, vol. 20, Supplement 4, May 2009, pp. iv19-iv20.

Bodey et al., "Failure of Cancer Vaccines: The Significant Limitations of this Approach to Immunotherapy," Anticancer Research, vol. 20, 2000, pp. 2665-2676.

Bodey et al., "MAGE-1, a Cancer/Testis-Antigen, Expression in Childhood Astrocytomas as an Indicator of Tumor Progression," in vivo, vol. 16, 2002, pp. 583-588.

Brand et al., "Prospect for Anti-HER2 Receptor Therapy in Breast Cancer," Anticancer Research, vol. 26, 2006, pp. 463-470.

Brass et al., "Translation initiation factor eIF-4gamma is encoded by an amplified gene and induces an immune response in squamous cell lung carcinoma," Human Molecular Genetics, vol. 6, No. 1, 1997, pp. 33-39.

(56) References Cited

OTHER PUBLICATIONS

Buchsbaum et al., "Treatment of Pancreatic Cancer Xenografts with Erbitux (IMC-C225) Anti-EGFR Antibody, Gemcitabine, and Radiation," Int. J. Radiation Oncology Biol. Phys., vol. 54, No. 4, 2002, pp. 1180-1193, XP-002358776.

Chamberlain et al., "Innovations and strategies for the development of anticancer vaccines," Expert Opinion on Pharmacotherapy, vol. 1, No. 4, 2000, pp. 603-614.

Chames et al., "Therapeutic Antibodies for the Treatment of Pancreatic Cancer," The Scientific World Journal, vol. 10, Jan. 1, 2010, pp. 1107-1120.

Chinese Office Action and Search Report, dated May 9, 2013, for Chinese Application No. 201180016730.5, with an English translation.

Comtesse et al., "Probing the human natural autoantibody repertoire using an immunoscreening approach," Clinical and Experimental Immunology, vol. 121, 2000, pp. 430-436.

Chinese Office Action and Search Report, dated Jul. 27, 2015, for Chinese Application No.

Corada et al., "Monoclonal antibodies directed to different regions of vascular endothelial cadherin extracellular domain affect adhesion and clustering of the protein and modulate endothelial permeability," Blood, vol. 97, No. 6, Mar. 15, 2001, pp. 1679-1684.

De Pascalis et al., "Grafting of "Abbreviated" Complementary-Determining Regions Containing Specificity-Determining Residues Essential for Ligand Contact to Engineer a Less Immunogenic Humanized Monoclonal Antibody," J. Immunol., vol. 169, 2002, pp. 3076-3084.

Ellis et al., "Identification and Characterization of a Novel Protein (p137) Which Transcytoses Bidirectionally in Caco-2 Cells", The Journal of Biological Chemistry, Sep. 1, 1995, vol. 270, No. 35, pp. 20717-20723.

Esteva et al., "Chemotheraphy of Metastatic Breast Cancer: What to Expect in 2001 and Beyond," The Oncologist, vol. 6, 2001, pp. 133-146.

Evans et al., "Vaccine therapy for cancer—fact or fiction?", Q J Med, vol. 92, 1999, pp. 299-307.

Extended European Search Report, dated Aug. 13, 2013, for European Application No. 11739882.6.

Extended European Search Report, dated Aug. 26, 2011, for European Application No. 09805010.7.

Extended European Search Report, dated Feb. 2, 2015, for European Application No. 12819473.5.

Extended European Search Report, dated Jan. 29, 2015, for European Application No. 12819899.1.

Extended European Search Report, dated Jan. 30, 2013, for European Application No. 09805009.9.

Extended European Search Report, dated Mar. 18, 2015, for European Application No. 12820225.6.

Extended European Search Report, dated Mar. 2, 2015, for European Application No. 12819759.7.

Extended European Search Report, dated Mar. 23, 2015, for European Application No. 12820596.0.

Extended European Search Report, dated Nov. 6, 2013, for European Application No. 11739876.8.

Extended European Search Report, dated Sep. 22, 2015, for European Application No. 13767612.8.

Extended European Search Report, dated Sep. 22, 2015, for European Application No. 13769665.4.

GenBank Accession No. AAU93399, cytoplasmic activation—proliferation-associated protein 1 [Gallus gallus], Sep. 22, 2005, 1 page.

GenBank Accession No. BAF96513, RNA granule protein 105 [Mus musculus], Jan. 5, 2008, 1 page.

GeneCards, "Cell Cycle Associated Protein 1—Biological research products for CAPRIN 1," updated Mar. 19, 2013, 10 pages.

Gong et al.,"Caprin-1 is a novel microRNA-223 target for regulating the proliferation and invasion of human breast cancer cells", Biomedicine & Pharmacotherapy, vol. 67, 2013, pp. 629-636.

Grill et al., "Activation/Division of Lymphocytes Results in Increased Levels of Cytoplasmic Activation/Proliferation-Associated Protein-1: Prototype of a New Family of Proteins," The Journal of Immunology, vol. 172, 2004, pp. 2389-2400.

Güre et al., "Human Lung Cancer Antigens Recognized by Autologous Antibodies: Definition of a Novel cDNA Derived from the Tumor Suppressor Gene Locus on Chromosome 3p21.3," Cancer Research, vol. 58, Mar. 1, 1998, pp. 1034-1041.

Gure et al., "SSX: A Multigene Family with Several Members Transcribed in Normal Testis and Human Cancer," International Journal of Cancer, vol. 72, 1997, pp. 965-971.

Harlow et al., "Antibodies a Laboratory Manual", Cold Spring Harbor Laboratory, Chapter 3, 1988, pp. 23-34.

Houghton et al., "Evaluation of Single-Agent Therapy in Human Colorectal Tumour Xenografts," Br. J. Cancer, vol. 37, 1978, pp. 833-840.

Hugo Gene Nomenclature Committee, Gene Symbol Report, CAPRIN1, Approved Name: Cell Cycle Associated Protein 1, HGNC ID: HGNC:6743, Nov. 3, 2012, 2 pages.

International Search Report and Written Opinion of the International Searching Authority (PCT/ISA/210 and PCT/ISA/237), dated Mar. 1, 2011, for International Application No. PCT/JP2011/052413, with an English translation of the International Search Report only.

International Search Report and Written Opinion of the International Searching Authority (PCT/ISA/210 and PCT/ISA/237), dated Mar. 15, 2011, for International Application No. PCT/JP2011/052384, with an English translation of the International Search Report only.

International Search Report and Written Opinion of the International Searching Authority (PCT/ISA/210 and PCT/ISA/237), dated Mar. 8, 2011, for International Application No. PCT/JP2011/052403, with an English translation of the International Search Report only.

International Search Report and Written Opinion of the International Searching Authority (PCT/ISA/210 and PCT/ISA/237), dated Mar. 8, 2011, for International Application No. PCT/JP2011/052414, with an English translation of the International Search Report only.

International Search Report and Written Opinion of the International Searching Authority (PCT/ISA/210 and PCT/ISA/237), dated Oct. 6, 2009, for International Application No. PCT/JP2009/063882, with an English translation of the International Search Report only.

International Search Report and Written Opinion of the International Searching Authority (PCT/ISA/210 and PCT/ISA/237), dated Sep. 8, 2009, for International Application No. PCT/JP2009/063883, with an English translation of the International Search Report only.

International Search Report and Written Opinion of the International Searching Authority (PCT/ISA/220, PCT/ISA/210 and PCT/ISA/237), dated Nov. 18, 2014, for International Application No. PCT/JP2014/071094.

Itoh et al., "HUB1 is an autoantigen frequently eliciting humoral immune response in patients with adult T cell leukemia," International Journal of Oncology, vol. 14, No. 4, Apr. 1999, pp. 703-708 (Abstract only provided).

Jang et al., "Antihypertensive Angiotensin I-Converting Enzyme Inhibitory Activity and Antioxidant Activity of Vitis hybrid-Vitis coignetiae Red Wine Made with *Saccharomyces cerevisiae*," Mycobiology, vol. 39, No. 2, 2011, pp. 137-139.

Jungbluth et al., "Immunohistochemical Analysis of NY-ESO-1 Antigen Expression in Normal and Malignant Human Tissues," International Journal of Cancer, vol. 92, 2001, pp. 856-860.

Jäger et al., "Identification of a Tissue-specific Putative Transcription Factor in Breast Tissue by Serological Screening of a Breast Cancer Library," Cancer Research, vol. 61, Mar. 1, 2001, pp. 2055-2061.

Kaddar et al., "Two new miR-16 targets: caprin-1 and HMGA1, proteins implicated in cell proliferation," Biology of the Cell, vol. 101, No. 9, Feb. 27, 2009, pp. 511-524.

(56) References Cited

OTHER PUBLICATIONS

Kajiji et al., "Six Monoclonal Antibodies to Human Pancreatic Cancer Antigens," Cancer Research, vol. 47, Mar. 1, 1987, pp. 1367-1376.

Karauzum et al., "Caprin 1 is Frequently Overexpressed in Human Lymphomas," American Society of Human Genetics, Cancer Genetics, Program No. 1190W, Oct. 12, 2011, One page (Abstract only provided).

Kataja et al., "Primary breast cancer: ESMO Clinical Recommendations for diagnosis, treatment and follow-up," Annals of Oncology, vol. 20, Supplement 4, May 2009, pp. iv10-iv14.

Katsafanas et al., "Colocalization of Transcription and Translation within Cytoplasmic Poxvirus Factories Coordinates Viral Expression and Subjugates Host Functions," Cell Host & Microbe, vol. 2, Oct. 2007, pp. 221-228.

Katsafanas et al., "Vaccinia Virus Intermediate Stage Transcription is Complemented by Ras-GTPase-activating Protein SH3 Domain-binding Protein (G3BP) . . . ," Journal of Biological Chemistry, vol. 279, No. 50, Dec. 10, 2004, pp. 52210-52217.

Kohler et al., "Tumor antigen analysis in neuroblastoma by serological interrogation of bioinformatic data," Cancer Science, vol. 101, No. 11, Nov. 2010, pp. 2316-2324.

Kolobova et al., "Microtubule-dependent association of AKAP350A and CCAR1 with RNA stress granules," Experimental Cell Research, vol. 315, 2009 (Available online Dec. 3, 2008), pp. 542-555.

Lu et al., "Identification of an immunological signature of tumor rejection in the neu transgenic mouse," 2007 AACR Annual Meeting, Apr. 14-18, 2007 (Presentation conducted on Apr. 17, 2007), One page (Abstract only provided).

Lu et al., "Targeting serum antibody for cancer diagnosis: a focus on colorectal cancer," Expert Opinion on Therapeutic Targets, vol. 11, No. 2, 2007, pp. 235-244.

Müller-Pillasch et al., "Identification of a new tumour-associated antigen TM4SF5 and its expression in human cancer," Gene, vol. 208, 1998, pp. 25-30.

Munodzana et al., "Conformational Dependence of Anaplasma marginale Major Surface Protein 5 Surface-Exposed B-Cell Epitopes", Infection and Immunity, vol. 66, No. 6, Jun. 1998, pp. 2619-2624.

Nakamura et al. "Gene Expression Profile of Metastatic Human Pancreatic Cancer Cells Depends on the Organ Microenvironment," Cancer Research, vol. 67, No. 1, Jan. 1, 2007, pp. 139-148.

NCBI Reference Sequence, Bos taurus cell cycle associated protein 1 (CAPRIN1), mRNA, Feb. 9, 2008, Accession No. NM_001076062, XM_615677, 2 pages.

NCBI Reference Sequence, caprin-1 [Bos taurus], 2009, Accession No. NP_001069530, XP_615677, 1 page.

NCBI Reference Sequence, caprin-1 [Gallus gallus], 2005, Accession No. NP_001026536, XP_423820, 1 page.

NCBI Reference Sequence, caprin-1 isoform 1 [*Homo sapiens*], 1995, Accession No. NP_005889, 3 pages.

NCBI Reference Sequence, caprin-1 isoform 2 [*Homo sapiens*], 1995, Accession No. NP_976240, 3 pages.

NCBI Reference Sequence, caprin-1 isoform a [Mus musculus], 1996, Accession No. NP_058019, 3 pages.

NCBI Reference Sequence, caprin-1 isoform b [Mus musculus], 1996, Accession No. NP_001104760, 3 pages.

NCBI Reference Sequence, caprin-1 isoform c [Mus musculus], 1996, Accession No. NP_001104761, 4 pages.

NCBI Reference Sequence, Gallus gallus cell cycle associated protein 1 (CAPRIN1), mRNA, Sep. 25, 2007, Accession No. NM_001031365, XM_423820, 2 pages.

NCBI Reference Sequence, *Homo sapiens* cell cycle associated protein 1 (CAPRIN1), transcript variant 1, mRNA, Feb. 11, 2008, Accession No. NM_005898, 7 pages.

NCBI Reference Sequence, *Homo sapiens* cell cycle associated protein 1 (CAPRIN1), transcript variant 2, mRNA, Feb. 10, 2008, Accession No. NM_203364, 6 pages.

NCBI Reference Sequence, Mus musculus cell cycle associated protein 1 (Caprin1), transcript variant 1, mRNA, Feb. 10, 2008, Accession No. NM_016739, 6 pages.

NCBI Reference Sequence, Mus musculus cell cycle associated protein 1 (CAPRIN1), transcript variant 2, mRNA, Feb. 11, 2008, Accession No. NM_001111289, 6 pages.

NCBI Reference Sequence, Mus musculus cell cycle associated protein 1 (CAPRIN1), transcript variant 3, mRNA, Feb. 11, 2008, Accession No. NM_001111290, 6 pages.

NCBI Reference Sequence, Mus musculus cell cycle associated protein 1 (Caprin1), transcript variant 4, mRNA, Feb. 10, 2008, Accession No. NM_001111291, 5 pages.

NCBI Reference Sequence, Mus musculus cell cycle associated protein 1 (Caprin1), transcript variant 5, mRNA, Feb. 11, 2008, Accession No. NM_001111292, 5 pages.

NCBI Reference Sequence, PREDICTED: Canis lupus familiaris cell cycle associated protein 1 (CAPRIN1), transcript variant 2, mRNA, Aug. 30, 2005, Accession No. XM_853016, 3 pages.

NCBI Reference Sequence, Predicted: caprin-1 [Equus caballus], 2008, Accession No. XP_001492799, 1 page.

NCBI Reference Sequence, Predicted: caprin-1 isoform 2 [Canis lupus familiaris], Dec. 2, 2011, Accession No. XP_858109, 1 page.

Nelson et al., "Screening for Breast Cancer: An Update for the U.S. Preventive Services Task Force," Annals of Internal Medicine, vol. 151, No. 10, Nov. 17, 2009, pp. 727-737.

Okano et al., "Abstract 519: Identification of a novel target for antibody therapy of breast cancer", Cancer Research, vol. 72, Issue 8, Supplement 1, Apr. 15, 2012, XP-002700046, 2 pages (Abstract only provided).

Padlan, "X-Ray Crystallography of Antibodies," Advances in Protein Chemistry, vol. 49, 1996, pp. 57-133.

Pegram et al., "Rational Combinations of Trastuzumab with Chemotherapeutic Drugs Used in the Treatment of Breast Cancer," Journal of the National Cancer Institute, vol. 96, No. 10, May 19, 2004, pp. 739-749.

Polyak et al., "Alanine-170 and proline-172 are critical determinants for extracellular CD20 epitopes; heterogeneity in the fine specificity of CD20 monoclonal antibodies is defined by additional requirements imposed by both amino acid . . . ", Blood, vol. 99, No. 9, May 1, 2002, pp. 3256-3262.

Punt et al., "Edrecolomab alone or in combination with fluorouracil and folinic acid in the adjuvant treatment of stage III colon cancer: a randomised study," Lancet, vol. 360, No. 9334, Aug. 31, 2002, pp. 671-677 (Abstract only provided).

Qiu et al., "Targeting a ribonucleoprotein complex containing the caprin-1 protein and the c-Myc mRNA suppresses tumor growth in mice: an identification of a novel oncotarget", Oncotarget, vol. 6, No. 4, Dec. 10, 2014, pp. 2148-2163.

R & D Systems, "IHC Products & Protocol Guide," printed Jan. 9, 2014, pp. 1-112.

Riechmann et al., "Reshaping human antibodies for therapy," Nature, vol. 332, Mar. 24, 1988, pp. 323-327.

Russian Notice of Allowance, dated Jun. 7, 2013, for Russian Application No. 2011108260/10, with an English translation.

Russian Office Action, dated Jan. 28, 2015, for Russian Application No. 2012137502/10, with a partial English translation.

Russian Office Action, dated Jul. 3, 2015, for Russian Application No. 2012137503/10, with an English translation.

Sabile et al., "Caprin-1, a novel Cyr61-interacting protein, promotes osteosarcoma tumor growth and lung metastasis in mice", Biochimica et Biophysica Acta, vol. 1832, 2013 (available online Mar. 23, 2013), pp. 1173-1182.

Saffari et al., "Identification of novel p53 target genes by cDNA AFLP in glioblastoma cells", Cancer Letters, vol. 273, 2009, pp. 316-322.

Sahin et al., "Human neoplasms elicit multiple specific immune responses in the autologous host," Proceedings of the National Academy of Sciences USA, vol. 92, Dec. 1995, pp. 11810-11813.

Scanlan et al., "Cancer-related Serological Recognition of Human Colon Cancer: Identification of Potential Diagnostic and Immunotherapeutic Targets," Cancer Research, vol. 62, Jul. 15, 2002, pp. 4041-4047.

(56) References Cited

OTHER PUBLICATIONS

Scanlan et al., "Characterization of Human Colon Cancer Antigens Recognized by Autologous Antibodies," International Journal of Cancer, vol. 76, 1998, pp. 652-658.
Solomon et al., "Distinct Structural Features of Caprin-1 Mediate Its Interaction with G3BP-1 and Its Induction of Phosphorylation of Eukaryotic Translation Initiation Factor 2α, Entry to Cytoplasmic Stress . . . ," Molecular and Cellular Biology, vol. 27, No. 6, Mar. 2007, pp. 2324-2342, XP-002690351.
Strome et al., "A Mechanistic Perspective of Monoclonal Antibodies in Cancer Therapy Beyond Target-Related Effects," The Oncologist, vol. 12, 2007, pp. 1084-1095.
Türeci et al., "The SSX-2 Gene, Which is Involved in the t(X; 18) Translocation of Synovial Sarcomas, Codes for the Human Tumor Antigen HOM-MEL-40," Cancer Research, vol. 56, Oct. 15, 1996, pp. 4766-4772.
UniProtKB/Swiss-Prot, RecName: Full=Caprin-1; AltName: Full=Cell cycle-associated protein 1; AltName: Full=Cytoplasmic activation- and proliferation-associated protein 1; AltName: Full=GPI-anchored membrane protein 1 . . . , Jun. 10, 2008, Accession No. Q14444, 6 pages.
UniProtKB/Swiss-Prot, RecName: Full=Caprin-1; AltName; Full=Cytoplasmic activation- and proliferation-associated protein 1; AltName: Full=RNA granule protein 105 [Bos taurus], Jun. 10, 2008, Accession No. Q1LZB6, 2 pages.
Vajdos et al., "Comprehensive Functional Maps of the Antigen-binding Site of an Anti-ErbB2 Antibody Obtained with Shotgun Scanning Mutagenesis," J. Mol. Biol., vol. 320, 2002, pp. 415-428.
Van Der Bruggen et al., "A Gene Encoding an Antigen Recognized by Cytolytic T Lymphocytes on a Human Melanoma," Science, vol. 254, Dec. 13, 1991, pp. 1643-1647 (Also published in Journal of Immunology, vol. 178, 2007, pp. 2617-2621).
Wang et al., "Absence of Caprin-1 Results in Defects in Cellular Proliferation", The Journal of Immunology, vol. 175, 2005, pp. 4274-4282.
Yanai et al., "Dlk-1, a cell surface antigen on foetal hepatic stem/progenitor cells, is expressed in hepatocellular, colon, pancreas and breast carcinomas at a high frequency," The Journal of Biochemistry, vol. 148, No. 1, 2010 (Published online Mar. 30, 2010), pp. 85-92.

Yarilin, "The Fundamentals of Immunology," Moscow: Meditsina, 1999, pp. 598-600 (4 pages total), ISBN 5-225-02755-5.
Carter, "Potent antibody therapeutics by design", Nature Reviews Immunology, vol. 6, May 2006 (Published online Apr. 7, 2006), pp. 343-357.
Extended European Search Report, dated Jan. 11, 2016, for European Application No. 13820574.5.
GenBank Accession No. BC001731, *Homo sapiens* cell cycle associated protein 1, mRNA (cDNA clone MGC: 1378 Image: 3355481), complete cds, Sep. 11, 2007, 3 pages.
Huang et al., "IgG Isotype Conversion of a Novel Human Anti-carcinoembryonic Antigen Antibody to Increase its Biological Activity," Anticancer Research, vol. 26, No. 2A, 2006, pp. 1057-1063.
Shibaguchi et al., "New Human Antibody IgG Subclass Conversion for Enhancement of Tumor-Cytotoxic Activity," Research, vol. 11, No. 3, 2006, pp. 15-16, with a partial English translation.
Decision on Grant of Patent for Invention issued May 16, 2016, in Russian Patent Application No. 2014108049, with English translation.
Decision on Grant of Patent for Invention dated Mar. 13, 2017, in Russian Patent Application No. 2012137503, with English translation.
Decision on Grant of Patent for Invention dated Mar. 29, 2017, in Russian Patent Application No. 2014108048, with English translation.
Examination Report dated Feb. 23, 2017, in Indian Patent Application No. 960/KOLNP/2011.
Extended European Search Report dated Feb. 27, 2017, in European Patent Application No. 14834828.7.
NCBI Reference Sequence:NP_005889 for human CAPRIN-1, printed Apr. 2017.
Non-Final Office Action dated Apr. 26, 2017, in U.S. Appl. No. 13/057,515.
Non-Final Office Action dated May 15, 2017, in U.S. Appl. No. 15/092,469.
Official Action dated Apr. 17, 2017, in Russian Patent Application No. 2014143785/10(070690), with English translation.
Roitt et al., "NK cells and K cells use several different receptors on the surface, to identify their targets," Immunology (2000), p. 181, with English translation.
Russian Office Action and Search Report for Russian Application No. 2014143784, dated Jan. 19, 2017, including a partial English translation.

SEQUENCE LISTING

<160> NUMBER OF SEQ ID NOS: 34

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide derived from rabbit

<400> SEQUENCE: 1

Ser His Ser Leu Gly
1               5

```
<210> SEQ ID NO 2
<211> LENGTH: 16
<212> TYPE: PRT
<213> ORGANISM: Artificial Sequence
<220> FEATURE:
<223> OTHER INFORMATION: Synthetic peptide derived from rabbit

<400> SEQUENCE: 2

Asp Ile Arg Ser Gly Gly Ser Ala Tyr Tyr Ala Asn Trp Ala Lys Gly
1               5                   10                  15

<210> SEQ ID NO 3
<211> LENGTH: 13
<212> TYPE: PRT
<213> ORGANISM: Artificial Sequence
<220> FEATURE:
<223> OTHER INFORMATION: Synthetic peptide derived from rabbit

<400> SEQUENCE: 3

Thr Asn Gly Pro Ser Asp Leu Thr Asn Arg Leu Asp Leu
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic peptide derived from rabbit

<400> SEQUENCE: 4

Gln Ala Ser Gln Ser Leu Tyr Asn Asn Glu Asn Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide derived from rabbit

<400> SEQUENCE: 5

Gly Ala Ser Thr Leu Ala Ser
1               5

<210> SEQ ID NO 6
<211> LENGTH: 13
<212> TYPE: PRT
<213> ORGANISM: Artificial Sequence
<220> FEATURE:
<223> OTHER INFORMATION: Synthetic peptide derived from rabbit

<400> SEQUENCE: 6

Leu Gly Glu Phe Ser Cys Gly Ser Ala Asp Cys Phe Ala
1               5                   10

<210> SEQ ID NO 7
<211> LENGTH: 121
<212> TYPE: PRT
<213> ORGANISM: Homo sapiens

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser His
            20                  25                  30

Ser Leu Gly Trp Val Arg Gln Ala Pro Gly Lys Gly Leu Glu Trp Ile
```

```
                    35                  40                  45

Gly Asp Ile Arg Ser Gly Gly Ser Ala Tyr Tyr Ala Asn Trp Ala Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Phe Cys Thr
                 85                  90                  95

Arg Thr Asn Gly Pro Ser Asp Leu Thr Asn Arg Leu Asp Leu Trp Gly
                100                 105                 110

Gln Gly Thr Leu Val Thr Val Ser Ser
            115                 120

<210> SEQ ID NO 8
<211> LENGTH: 121
<212> TYPE: PRT
<213> ORGANISM: Homo sapiens

<400> SEQUENCE: 8

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Ser Ser His
                 20                  25                  30

Ser Leu Gly Trp Val Arg Gln Ala Pro Gly Lys Gly Leu Glu Trp Ile
             35                  40                  45

Gly Asp Ile Arg Ser Gly Gly Ser Ala Tyr Tyr Ala Asn Trp Ala Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Thr
                 85                  90                  95

Arg Thr Asn Gly Pro Ser Asp Leu Thr Asn Arg Leu Asp Leu Trp Gly
                100                 105                 110

Gln Gly Thr Leu Val Thr Val Ser Ser
            115                 120

<210> SEQ ID NO 9
<211> LENGTH: 120
<212> TYPE: PRT
<213> ORGANISM: Homo sapiens

<400> SEQUENCE: 9

Gln Ser Leu Val Glu Ser Gly Gly Gly Leu Val Gln Pro Gly Gly Ser
 1               5                  10                  15

Leu Arg Leu Ser Cys Ala Ala Ser Gly Phe Ser Leu Ser Ser His Ser
                 20                  25                  30

Leu Gly Trp Val Arg Gln Ala Pro Gly Lys Gly Leu Glu Trp Ile Gly
             35                  40                  45

Asp Ile Arg Ser Gly Gly Ser Ala Tyr Tyr Ala Asn Trp Ala Lys Gly
 50                  55                  60

Arg Phe Thr Ile Ser Arg Thr Ser Lys Asn Thr Val Tyr Leu Gln
 65                  70                  75                  80

Met Asn Ser Leu Arg Ala Glu Asp Thr Ala Val Tyr Phe Cys Thr Arg
                 85                  90                  95

Thr Asn Gly Pro Ser Asp Leu Thr Asn Arg Leu Asp Leu Trp Gly Gln
                100                 105                 110

Gly Thr Leu Val Thr Val Ser Ser
            115
```

<210> SEQ ID NO 10
<211> LENGTH: 121
<212> TYPE: PRT
<213> ORGANISM: Homo sapiens

<400> SEQUENCE: 10

Glu Gln Ser Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser His
            20                  25                  30

Ser Leu Gly Trp Val Arg Gln Ala Pro Gly Lys Gly Leu Glu Trp Ile
        35                  40                  45

Gly Asp Ile Arg Ser Gly Gly Ser Ala Tyr Tyr Ala Asn Trp Ala Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Thr Asn Gly Pro Ser Asp Leu Thr Asn Arg Leu Asp Leu Trp Gly
            100                 105                 110

Gln Gly Thr Leu Val Thr Val Ser Ser
        115                 120

<210> SEQ ID NO 11
<211> LENGTH: 113
<212> TYPE: PRT
<213> ORGANISM: Homo sapiens

<400> SEQUENCE: 11

Ala Ile Gln Met Thr Gln Ser Pro Ser Ser Leu Ser Ala Ser Val Gly
1               5                   10                  15

Asp Arg Val Thr Ile Asn Cys Gln Ala Ser Gln Ser Leu Tyr Asn Asn
            20                  25                  30

Glu Asn Leu Ala Trp Phe Gln Gln Lys Pro Gly Lys Ala Pro Lys Arg
        35                  40                  45

Leu Ile Tyr Gly Ala Ser Thr Leu Ala Ser Gly Val Ser Ser Arg Phe
50                  55                  60

Ser Gly Ser Gly Ser Gly Thr Asp Phe Thr Leu Thr Ile Ser Ser Leu
65                  70                  75                  80

Gln Pro Glu Asp Phe Ala Ile Tyr Tyr Cys Leu Gly Glu Phe Ser Cys
                85                  90                  95

Gly Ser Ala Asp Cys Phe Ala Phe Gly Gly Gly Thr Lys Val Glu Ile
            100                 105                 110

Lys

<210> SEQ ID NO 12
<211> LENGTH: 113
<212> TYPE: PRT
<213> ORGANISM: Homo sapiens

<400> SEQUENCE: 12

Glu Ile Val Leu Thr Gln Ser Pro Ser Ser Leu Ser Ala Ser Val Gly
1               5                   10                  15

Asp Arg Val Thr Ile Asn Cys Gln Ala Ser Gln Ser Leu Tyr Asn Asn
            20                  25                  30

Glu Asn Leu Ala Trp Phe Gln Gln Lys Pro Gly Lys Val Pro Lys Arg
            35                  40                  45

Leu Ile Tyr Gly Ala Ser Thr Leu Ala Ser Gly Val Ser Ser Arg Phe
     50                  55                  60

Ser Gly Ser Gly Ser Gly Thr Glu Phe Thr Leu Thr Ile Ser Asn Leu
65                  70                  75                  80

Gln Pro Glu Asp Phe Ala Thr Tyr Tyr Cys Leu Gly Glu Phe Ser Cys
                85                  90                  95

Gly Ser Ala Asp Cys Phe Ala Phe Gly Gly Gly Thr Lys Val Glu Ile
                100                 105                 110

Lys

<210> SEQ ID NO 13
<211> LENGTH: 113
<212> TYPE: PRT
<213> ORGANISM: Homo sapiens

<400> SEQUENCE: 13

Glu Gln Val Leu Thr Gln Ser Pro Ser Ser Leu Ser Ala Ser Val Gly
1               5                   10                  15

Asp Arg Val Thr Ile Asn Cys Gln Ala Ser Gln Ser Leu Tyr Asn Asn
            20                  25                  30

Glu Asn Leu Ala Trp Phe Gln Gln Lys Pro Gly Lys Val Pro Lys Arg
            35                  40                  45

Leu Ile Tyr Gly Ala Ser Thr Leu Ala Ser Gly Val Ser Ser Arg Phe
     50                  55                  60

Ser Gly Ser Gly Ser Gly Thr Glu Phe Thr Leu Thr Ile Ser Asn Leu
65                  70                  75                  80

Gln Pro Glu Asp Phe Ala Ile Tyr Tyr Cys Leu Gly Glu Phe Ser Cys
                85                  90                  95

Gly Ser Ala Asp Cys Phe Ala Phe Gly Gly Gly Thr Lys Val Glu Ile
                100                 105                 110

Lys

<210> SEQ ID NO 14
<211> LENGTH: 113
<212> TYPE: PRT
<213> ORGANISM: Homo sapiens

<400> SEQUENCE: 14

Asp Ile Val Leu Thr Gln Ser Pro Ser Ser Leu Ser Ala Ser Val Gly
1               5                   10                  15

Asp Arg Val Thr Ile Asn Cys Gln Ala Ser Gln Ser Leu Tyr Asn Asn
            20                  25                  30

Glu Asn Leu Ala Trp Phe Gln Gln Lys Pro Gly Lys Val Pro Lys Arg
            35                  40                  45

Leu Ile Tyr Gly Ala Ser Thr Leu Ala Ser Gly Val Ser Ser Arg Phe
     50                  55                  60

Ser Gly Ser Gly Ser Gly Thr Glu Phe Thr Leu Thr Ile Ser Ser Leu
65                  70                  75                  80

Gln Cys Glu Asp Phe Ala Ile Tyr Tyr Cys Leu Gly Glu Phe Ser Cys
                85                  90                  95

Gly Ser Ala Asp Cys Phe Ala Phe Gly Gly Gly Thr Lys Val Glu Ile
                100                 105                 110

Lys

-continued

```
<210> SEQ ID NO 15
<211> LENGTH: 112
<212> TYPE: PRT
<213> ORGANISM: Homo sapiens

<400> SEQUENCE: 15

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Leu Tyr Asn Asn Glu
            20                  25                  30

Asn Leu Ala Trp Phe Gln Gln Lys Pro Gly Lys Val Pro Lys Arg Leu
        35                  40                  45

Ile Tyr Gly Ala Ser Thr Leu Ala Ser Gly Val Ser Ser Arg Phe Ser
    50                  55                  60

Gly Ser Gly Ser Gly Thr Glu Phe Thr Leu Thr Ile Ser Ser Leu Gln
65                  70                  75                  80

Cys Glu Asp Phe Ala Ile Tyr Tyr Cys Leu Gly Glu Phe Ser Cys Gly
                85                  90                  95

Ser Ala Asp Cys Phe Ala Phe Gly Gly Gly Thr Lys Val Glu Ile Lys
            100                 105                 110

<210> SEQ ID NO 16
<211> LENGTH: 5562
<212> TYPE: DNA
<213> ORGANISM: Homo sapiens
<220> FEATURE:
<221> NAME/KEY: CDS
<222> LOCATION: (190)..(2319)

<400> SEQUENCE: 16
cagagggctg ctggctggct aagtccctcc cgctcccggc tctcgcctca ctaggagcgg      60
ctctcggtgc agcgggacag ggcgaagcgg cctgcgccca cggagcgcgc gacactgccc     120
ggaagggacc gccaccccttg ccccctcagc tgcccactcg tgatttccag cggcctccgc    180 gcgcgcacg atg ccc tcg gcc acc agc cac agc ggg agc ggc agc aag tcg    231
          Met Pro Ser Ala Thr Ser His Ser Gly Ser Gly Ser Lys Ser
          1               5                   10 tcc gga ccg cca ccg ccg tcg ggt tcc tcc ggg agt gag gcg gcc gcg    279
Ser Gly Pro Pro Pro Pro Ser Gly Ser Ser Gly Ser Glu Ala Ala Ala
15                  20                  25                  30 gga gcc ggg gcc gcc gcg ccg gct tct cag cac ccc gca acc ggc acc    327
Gly Ala Gly Ala Ala Ala Pro Ala Ser Gln His Pro Ala Thr Gly Thr
                35                  40                  45 ggc gct gtc cag acc gag gcc atg aag cag att ctc ggg gtg atc gac    375
Gly Ala Val Gln Thr Glu Ala Met Lys Gln Ile Leu Gly Val Ile Asp
            50                  55                  60 aag aaa ctt cgg aac ctg gag aag aaa aag ggt aag ctt gat gat tac    423
Lys Lys Leu Arg Asn Leu Glu Lys Lys Lys Gly Lys Leu Asp Asp Tyr
        65                  70                  75 cag gaa cga atg aac aaa ggg gaa agg ctt aat caa gat cag ctg gat    471
Gln Glu Arg Met Asn Lys Gly Glu Arg Leu Asn Gln Asp Gln Leu Asp
    80                  85                  90 gcc gtt tct aag tac cag gaa gtc aca aat aat ttg gag ttt gca aaa    519
Ala Val Ser Lys Tyr Gln Glu Val Thr Asn Asn Leu Glu Phe Ala Lys
95                  100                 105                 110 gaa tta cag agg agt ttc atg gca cta agt caa gat att cag aaa aca    567
Glu Leu Gln Arg Ser Phe Met Ala Leu Ser Gln Asp Ile Gln Lys Thr
                115                 120                 125 ata aag aag aca gca cgt cgg gag cag ctt atg aga gaa gaa gct gaa    615
```

```
              Ile Lys Lys Thr Ala Arg Arg Glu Gln Leu Met Arg Glu Ala Glu
                          130                 135                 140 cag aaa cgt tta aaa act gta ctt gag cta cag tat gtt ttg gac aaa        663
Gln Lys Arg Leu Lys Thr Val Leu Glu Leu Gln Tyr Val Leu Asp Lys
            145                 150                 155 ttg gga gat gat gaa gtg cgg act gac ctg aaa caa ggt ttg aat gga        711
Leu Gly Asp Asp Glu Val Arg Thr Asp Leu Lys Gln Gly Leu Asn Gly
160                 165                 170 gtg cca ata ttg tcc gaa gag gag ttg tca ttg ttg gat gaa ttc tat        759
Val Pro Ile Leu Ser Glu Glu Glu Leu Ser Leu Leu Asp Glu Phe Tyr
175                 180                 185                 190 aag cta gta gac cct gaa cgg gac atg agc ttg agg ttg aat gaa cag        807
Lys Leu Val Asp Pro Glu Arg Asp Met Ser Leu Arg Leu Asn Glu Gln
                195                 200                 205 tat gaa cat gcc tcc att cac ctg tgg gac ctg ctg gaa ggg aag gaa        855
Tyr Glu His Ala Ser Ile His Leu Trp Asp Leu Leu Glu Gly Lys Glu
            210                 215                 220 aaa cct gta tgt gga acc acc tat aaa gtt cta aag gaa att gtt gag        903
Lys Pro Val Cys Gly Thr Thr Tyr Lys Val Leu Lys Glu Ile Val Glu
        225                 230                 235 cgt gtt ttt cag tca aac tac ttt gac agc acc cac aac cac cag aat        951
Arg Val Phe Gln Ser Asn Tyr Phe Asp Ser Thr His Asn His Gln Asn
240                 245                 250 ggg ctg tgt gag gaa gaa gag gca gcc tca gca cct gca gtt gaa gac        999
Gly Leu Cys Glu Glu Glu Glu Ala Ala Ser Ala Pro Ala Val Glu Asp
255                 260                 265                 270 cag gta cct gaa gct gaa cct gag cca gca gaa gag tac act gag caa       1047
Gln Val Pro Glu Ala Glu Pro Glu Pro Ala Glu Glu Tyr Thr Glu Gln
                275                 280                 285 agt gaa gtt gaa tca aca gag tat gta aat aga cag ttc atg gca gaa       1095
Ser Glu Val Glu Ser Thr Glu Tyr Val Asn Arg Gln Phe Met Ala Glu
            290                 295                 300 aca cag ttc acc agt ggt gaa aag gag cag gta gat gag tgg aca gtt       1143
Thr Gln Phe Thr Ser Gly Glu Lys Glu Gln Val Asp Glu Trp Thr Val
        305                 310                 315 gaa acg gtt gag gtg gta aat tca ctc cag cag caa cct cag gct gca       1191
Glu Thr Val Glu Val Val Asn Ser Leu Gln Gln Gln Pro Gln Ala Ala
320                 325                 330 tcc cct tca gta cca gag ccc cac tct ttg act cca gtg gct cag gca       1239
Ser Pro Ser Val Pro Glu Pro His Ser Leu Thr Pro Val Ala Gln Ala
335                 340                 345                 350 gat ccc ctt gtg aga aga cag cga gta caa gac ctt atg gca caa atg       1287
Asp Pro Leu Val Arg Arg Gln Arg Val Gln Asp Leu Met Ala Gln Met
                355                 360                 365 cag ggt ccc tat aat ttc ata cag gat tca atg ctg gat ttt gaa aat       1335
Gln Gly Pro Tyr Asn Phe Ile Gln Asp Ser Met Leu Asp Phe Glu Asn
            370                 375                 380 cag aca ctt gat cct gcc att gta tct gca cag cct atg aat cca aca       1383
Gln Thr Leu Asp Pro Ala Ile Val Ser Ala Gln Pro Met Asn Pro Thr
        385                 390                 395 caa aac atg gac atg ccc cag ctg gtt tgc cct cca gtt cat tct gaa       1431
Gln Asn Met Asp Met Pro Gln Leu Val Cys Pro Pro Val His Ser Glu
400                 405                 410 tct aga ctt gct cag cct aat caa gtt cct gta caa cca gaa gcg aca       1479
Ser Arg Leu Ala Gln Pro Asn Gln Val Pro Val Gln Pro Glu Ala Thr
415                 420                 425                 430 cag gtt cct ttg gta tca tcc aca agt gag ggg tac aca gca tct caa       1527
Gln Val Pro Leu Val Ser Ser Thr Ser Glu Gly Tyr Thr Ala Ser Gln
                435                 440                 445
```

| | | |
|---|---|---|
| ccc ttg tac cag cct tct cat gct aca gag caa cga cca cag aag gaa<br>Pro Leu Tyr Gln Pro Ser His Ala Thr Glu Gln Arg Pro Gln Lys Glu<br>                   450                          455                    460 | | 1575 |
| cca att gat cag att cag gca aca atc tct tta aat aca gac cag act<br>Pro Ile Asp Gln Ile Gln Ala Thr Ile Ser Leu Asn Thr Asp Gln Thr<br>         465                        470                         475 | | 1623 |
| aca gca tca tca tcc ctt cct gct gcg tct cag cct caa gta ttt cag<br>Thr Ala Ser Ser Ser Leu Pro Ala Ala Ser Gln Pro Gln Val Phe Gln<br>    480                         485                       490 | | 1671 |
| gct ggg aca agc aaa cct tta cat agc agt gga atc aat gta aat gca<br>Ala Gly Thr Ser Lys Pro Leu His Ser Ser Gly Ile Asn Val Asn Ala<br>495                       500                       505                   510 | | 1719 |
| gct cca ttc caa tcc atg caa acg gtg ttc aat atg aat gcc cca gtt<br>Ala Pro Phe Gln Ser Met Gln Thr Val Phe Asn Met Asn Ala Pro Val<br>                  515                      520                     525 | | 1767 |
| cct cct gtt aat gaa cca gaa act tta aaa cag caa aat cag tac cag<br>Pro Pro Val Asn Glu Pro Glu Thr Leu Lys Gln Gln Asn Gln Tyr Gln<br>         530                        535                       540 | | 1815 |
| gcc agt tat aac cag agc ttt tct agt cag cct cac caa gta gaa caa<br>Ala Ser Tyr Asn Gln Ser Phe Ser Ser Gln Pro His Gln Val Glu Gln<br>    545                       550                       555 | | 1863 |
| aca gag ctt cag caa gaa cag ctt caa aca gtg gtt ggc act tac cat<br>Thr Glu Leu Gln Gln Glu Gln Leu Gln Thr Val Val Gly Thr Tyr His<br>         560                        565                     570 | | 1911 |
| ggt tcc cca gac cag tcc cat caa gtg act ggt aac cac cag cag cct<br>Gly Ser Pro Asp Gln Ser His Gln Val Thr Gly Asn His Gln Gln Pro<br>575                     580                       585                   590 | | 1959 |
| cct cag cag aac act gga ttt cca cgt agc aat cag ccc tat tac aat<br>Pro Gln Gln Asn Thr Gly Phe Pro Arg Ser Asn Gln Pro Tyr Tyr Asn<br>                  595                      600                     605 | | 2007 |
| agt cgt ggt gtg tct cgt gga ggc tcc cgt ggt gct aga ggc ttg atg<br>Ser Arg Gly Val Ser Arg Gly Gly Ser Arg Gly Ala Arg Gly Leu Met<br>                     610                      615                     620 | | 2055 |
| aat gga tac cgg ggc cct gcc aat gga ttc aga gga gga tat gat ggt<br>Asn Gly Tyr Arg Gly Pro Ala Asn Gly Phe Arg Gly Gly Tyr Asp Gly<br>         625                        630                       635 | | 2103 |
| tac cgc cct tca ttc tct aac act cca aac agt ggt tat aca cag tct<br>Tyr Arg Pro Ser Phe Ser Asn Thr Pro Asn Ser Gly Tyr Thr Gln Ser<br>    640                       645                       650 | | 2151 |
| cag ttc agt gct ccc cgg gat tac tct ggc tat caa cgg gat gga tat<br>Gln Phe Ser Ala Pro Arg Asp Tyr Ser Gly Tyr Gln Arg Asp Gly Tyr<br>655                     660                       665                   670 | | 2199 |
| cag cag aat ttc aag cga ggc tct ggg cag agt gga cca cgg gga gcc<br>Gln Gln Asn Phe Lys Arg Gly Ser Gly Gln Ser Gly Pro Arg Gly Ala<br>                  675                      680                     685 | | 2247 |
| cca cga ggt cgt gga ggg ccc cca aga ccc aac aga ggg atg ccg caa<br>Pro Arg Gly Arg Gly Gly Pro Pro Arg Pro Asn Arg Gly Met Pro Gln<br>         690                        695                     700 | | 2295 |
| atg aac act cag caa gtg aat taa tctgattcac aggattatgt ttaatcgcca<br>Met Asn Thr Gln Gln Val Asn<br>         705 | | 2349 |
| aaaacacact ggccagtgta ccataatatg ttaccagaag agttattatc tatttgttct | | 2409 |
| cccttcagg aaacttattg taaagggact gttttcatcc cataaagaca ggactacaat | | 2469 |
| tgtcagcttt ctattacctg gatatggaag gaaactattt ttactctgca tgttctgtcc | | 2529 |
| taagcgtcat cttgagcctt gcacatgata ctcagattcc tcaccttgc ttaggagtaa | | 2589 |
| aacaatatac tttacagggt gataataatc tccatagtta tttgaagtgg cttgaaaaag | | 2649 |
| gcaagattga cttttatgac attggataaa atctacaaat cagccctcga gttattcaat | | 2709 |

```
gataactgac aaactaaatt atttccctag aaaggaagat gaaaggagtg gagtgtggtt    2769
tggcagaaca actgcatttc acagcttttc cagttaaatt ggagcactga acgttcagat    2829
gcataccaaa ttatgcatgg gtcctaatca cacatataag gctggctacc agctttgaca    2889
cagcactgtt catctggcca aacaactgtg gttaaaaaca catgtaaaat gcttttttaac   2949 agctgatact gtataagaca aagccaagat gcaaaattag gctttgattg gcacttttttg  3009 aaaaatatgc aacaaatatg ggatgtaatc cggatggccg cttctgtact taatgtgaaa   3069
tatttagata ccttttttgaa cacttaacag tttctttgag acaatgactt ttgtaaggat   3129
tggtactatc tatcattcct tatgacatgt acattgtctg tcactaatcc ttggattttg   3189
ctgtattgtc acctaaattg gtacaggtac tgatgaaaat ctctagtgga taatcataac   3249
actctcggtc acatgttttt ccttcagctt gaaagcttttt ttttaaaagg aaagatacc   3309 aaatgcctgc tgctaccacc cttttcaatt gctatctttt gaaaggcacc agtatgtgtt   3369
ttagattgat ttccctgttt cagggaaatc acggacagta gtttcagttc tgatggtata   3429
agcaaaacaa ataaaacgtt tataaaagtt gtatcttgaa acactggtgt tcaacagcta   3489
gcagcttatg tgattcaccc catgccacgt tagtgtcaca aattttatgg tttatctcca   3549
gcaacatttc tctagtactt gcacttatta tcttttgtct aatttaaccct taactgaatt   3609 ctccgtttct cctggaggca tttatattca gtgataattc cttcccttag atgcataggg   3669
agagtctcta aatttgatgg aaatggacac ttgagtagtg acttagcctt atgtactctg   3729
ttggaatttg tgctagcagt ttgagcacta gttctgtgtg cctaggaagt taatgctgct   3789
tattgtctca ttctgacttc atggagaatt aatcccacct ttaagcaaag gctactaagt   3849
taatggtatt ttctgtgcag aaattaaatt ttatttttcag catttagccc aggaattctt   3909
ccagtaggtg ctcagctatt taaaaacaaa actattctca acattcatc attagacaac    3969 tggagttttt gctggttttg taacctacca aaatggatag gctgttgaac attccacatt   4029
caaaagtttt gtagggtggt gggaaatggg ggatcttcaa tgtttatttt aaaataaaat   4089
aaaataagtt cttgactttt ctcatgtgtg gttgtggtac atcatattgg aagggttaac   4149
ctgttacttt ggcaaatgag tatttttttg ctagcacctc cccttgcgtg ctttaaatga   4209
catctgcctg ggatgtacca caaccatatg ttacctgtat cttagggggaa tggataaaat   4269 atttgtggtt tactgggtaa tccctagatg atgtatgctt gcagtcctat ataaaactaa   4329
atttgctatc tgtgtagaaa ataatttcat gacatttaca atcaggactg aagtaagttc   4389
ttcacacagt gacctctgaa tcagtttcag agaagggatg ggggagaaaa tgccttctag   4449
gttttgaact tctatgcatt agtgcagatg ttgtgaatgt gtaaaggtgt tcatagtttg   4509 actgttttcta tgtatgtttt ttcaaagaat tgttcctttt tttgaactat aattttttctt   4569 ttttttggtta ttttaccatc acagtttaaa tgtatatctt ttatgtctct actcagacca    4629 tattttttaaa ggggtgcctc attatggggc agagaacttt tcaataagtc tcattaagat   4689
ctgaatcttg gttctaagca ttctgtataa tatgtgattg cttgtcctag ctgcagaagg   4749 cctttttgttt ggtcaaatgc atatttttagc agagtttcaa ggaaatgatt gtcacacatg   4809
tcactgtagc ctcttggtgt agcaagctca catacaaaat acttttgtat atgcataata   4869
taaatcatct catgtggata tgaaacttct tttttaaaac ttaaaaaggt agaatgttat   4929
tgattacctt gattagggca gttttatttc cagatcctaa taattcctaa aaatatgga   4989 aaagtttttt ttcaatcatt gtaccttgat attaaaacaa atatcccttta agtatttcta   5049
```

```
atcagttagc ttctacagtt cttttgtctc cttttatatg cagctcttac gtgggagact    5109
tttccactta aaggagacat agaatgtgtg cttattctca gaaggttcat taactgaggt    5169
gatgagttaa caactagttg agcagtcagc ttcctaagtg ttttaggaca tttgttcatt    5229
atattttccg tcatataact agaggaagtg gaatgcagat aagtgccgaa ttcaaaccct    5289
tcattttatg tttaagctcc tgaatctgca ttccacttgg gttgttttta agcattctaa    5349
attttagttg attataagtt agatttcaca gaatcagtat tgcccttgat cttgtccttt    5409
ttatggagtt aacggggagg aagacccctc aggaaaacga aagtaaattg ttaaggctca    5469
tcttcatacc tttttccatt ttgaatccta caaaaatact gcaaaagact agtgaatgtt    5529
taaaattaca ctagattaaa aatatgaaa gtc                                  5562
```

<210> SEQ ID NO 17
<211> LENGTH: 709
<212> TYPE: PRT
<213> ORGANISM: Homo sapiens

<400> SEQUENCE: 17

```
Met Pro Ser Ala Thr Ser His Ser Gly Ser Gly Ser Lys Ser Gly
1               5                   10                  15

Pro Pro Pro Pro Ser Gly Ser Ser Gly Ser Glu Ala Ala Gly Ala
                20                  25                  30

Gly Ala Ala Ala Pro Ala Ser Gln His Pro Ala Thr Gly Thr Gly Ala
            35                  40                  45

Val Gln Thr Glu Ala Met Lys Gln Ile Leu Gly Val Ile Asp Lys Lys
50                  55                  60

Leu Arg Asn Leu Glu Lys Lys Gly Lys Leu Asp Asp Tyr Gln Glu
65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
                100                 105                 110

Gln Arg Ser Phe Met Ala Leu Ser Gln Asp Ile Gln Lys Thr Ile Lys
                115                 120                 125

Lys Thr Ala Arg Arg Glu Gln Leu Met Arg Glu Glu Ala Glu Gln Lys
130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175

Ile Leu Ser Glu Glu Glu Leu Ser Leu Leu Asp Glu Phe Tyr Lys Leu
                180                 185                 190

Val Asp Pro Glu Arg Asp Met Ser Leu Arg Leu Asn Glu Gln Tyr Glu
                195                 200                 205

His Ala Ser Ile His Leu Trp Asp Leu Leu Glu Gly Lys Glu Lys Pro
            210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
                245                 250                 255

Cys Glu Glu Glu Glu Ala Ala Ser Ala Pro Ala Val Glu Asp Gln Val
                260                 265                 270

Pro Glu Ala Glu Pro Glu Pro Ala Glu Glu Tyr Thr Glu Gln Ser Glu
                275                 280                 285
```

```
Val Glu Ser Thr Glu Tyr Val Asn Arg Gln Phe Met Ala Glu Thr Gln
    290                 295                 300

Phe Thr Ser Gly Glu Lys Glu Gln Val Asp Glu Trp Thr Val Glu Thr
305                 310                 315                 320

Val Glu Val Val Asn Ser Leu Gln Gln Gln Pro Gln Ala Ala Ser Pro
                325                 330                 335

Ser Val Pro Glu Pro His Ser Leu Thr Pro Val Ala Gln Ala Asp Pro
                340                 345                 350

Leu Val Arg Arg Gln Arg Val Gln Asp Leu Met Ala Gln Met Gln Gly
                355                 360                 365

Pro Tyr Asn Phe Ile Gln Asp Ser Met Leu Asp Phe Glu Asn Gln Thr
    370                 375                 380

Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
                405                 410                 415

Leu Ala Gln Pro Asn Gln Val Pro Val Gln Pro Glu Ala Thr Gln Val
                420                 425                 430

Pro Leu Val Ser Ser Thr Ser Glu Gly Tyr Thr Ala Ser Gln Pro Leu
                435                 440                 445

Tyr Gln Pro Ser His Ala Thr Glu Gln Arg Pro Gln Lys Glu Pro Ile
    450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
                485                 490                 495

Thr Ser Lys Pro Leu His Ser Ser Gly Ile Asn Val Asn Ala Ala Pro
                500                 505                 510

Phe Gln Ser Met Gln Thr Val Phe Asn Met Asn Ala Pro Val Pro Pro
    515                 520                 525

Val Asn Glu Pro Glu Thr Leu Lys Gln Gln Asn Gln Tyr Gln Ala Ser
    530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
                565                 570                 575

Pro Asp Gln Ser His Gln Val Thr Gly Asn His Gln Gln Pro Pro Gln
                580                 585                 590

Gln Asn Thr Gly Phe Pro Arg Ser Asn Gln Pro Tyr Tyr Asn Ser Arg
    595                 600                 605

Gly Val Ser Arg Gly Gly Ser Arg Gly Ala Arg Gly Leu Met Asn Gly
    610                 615                 620

Tyr Arg Gly Pro Ala Asn Gly Phe Arg Gly Gly Tyr Asp Gly Tyr Arg
625                 630                 635                 640

Pro Ser Phe Ser Asn Thr Pro Asn Ser Gly Tyr Thr Gln Ser Gln Phe
                645                 650                 655

Ser Ala Pro Arg Asp Tyr Ser Gly Tyr Gln Arg Asp Gly Tyr Gln Gln
                660                 665                 670

Asn Phe Lys Arg Gly Ser Gly Gln Ser Gly Pro Arg Gly Ala Pro Arg
    675                 680                 685

Gly Arg Gly Gly Pro Pro Arg Pro Asn Arg Gly Met Pro Gln Met Asn
    690                 695                 700
```

-continued

Thr Gln Gln Val Asn
705

```
<210> SEQ ID NO 18
<211> LENGTH: 3553
<212> TYPE: DNA
<213> ORGANISM: Homo sapiens
<220> FEATURE:
<221> NAME/KEY: CDS
<222> LOCATION: (190)..(2274)

<400> SEQUENCE: 18
```

| | | |
|---|---|---|
| cagagggctg ctggctggct aagtccctcc cgctcccggc tctcgcctca ctaggagcgg | 60 |
| ctctcggtgc agcgggacag ggcgaagcgg cctgcgccca cggagcgcgc gacactgccc | 120 |
| ggaagggacc gccacccttg cccctcagc tgcccactcg tgatttccag cggcctccgc | 180 |

| gcgcgcacg atg ccc tcg gcc acc agc cac agc ggg agc ggc agc aag tcg | 231 |
|---|---|
| Met Pro Ser Ala Thr Ser His Ser Gly Ser Gly Ser Lys Ser | |
| 1               5                   10 | |

| tcc gga ccg cca ccg ccg tcg ggt tcc tcc ggg agt gag gcg gcc gcg | 279 |
|---|---|
| Ser Gly Pro Pro Pro Pro Ser Gly Ser Ser Gly Ser Glu Ala Ala Ala | |
| 15                  20                  25                  30 | |

| gga gcc ggg gcc gcc gcg ccg gct tct cag cac ccc gca acc ggc acc | 327 |
|---|---|
| Gly Ala Gly Ala Ala Ala Pro Ala Ser Gln His Pro Ala Thr Gly Thr | |
| 35                  40                  45 | |

| ggc gct gtc cag acc gag gcc atg aag cag att ctc ggg gtg atc gac | 375 |
|---|---|
| Gly Ala Val Gln Thr Glu Ala Met Lys Gln Ile Leu Gly Val Ile Asp | |
| 50                  55                  60 | |

| aag aaa ctt cgg aac ctg gag aag aaa aag ggt aag ctt gat gat tac | 423 |
|---|---|
| Lys Lys Leu Arg Asn Leu Glu Lys Lys Lys Gly Lys Leu Asp Asp Tyr | |
| 65                  70                  75 | |

| cag gaa cga atg aac aaa ggg gaa agg ctt aat caa gat cag ctg gat | 471 |
|---|---|
| Gln Glu Arg Met Asn Lys Gly Glu Arg Leu Asn Gln Asp Gln Leu Asp | |
| 80                  85                  90 | |

| gcc gtt tct aag tac cag gaa gtc aca aat aat ttg gag ttt gca aaa | 519 |
|---|---|
| Ala Val Ser Lys Tyr Gln Glu Val Thr Asn Asn Leu Glu Phe Ala Lys | |
| 95                  100                 105                 110 | |

| gaa tta cag agg agt ttc atg gca cta agt caa gat att cag aaa aca | 567 |
|---|---|
| Glu Leu Gln Arg Ser Phe Met Ala Leu Ser Gln Asp Ile Gln Lys Thr | |
| 115                 120                 125 | |

| ata aag aag aca gca cgt cgg gag cag ctt atg aga gaa gaa gct gaa | 615 |
|---|---|
| Ile Lys Lys Thr Ala Arg Arg Glu Gln Leu Met Arg Glu Glu Ala Glu | |
| 130                 135                 140 | |

| cag aaa cgt tta aaa act gta ctt gag cta cag tat gtt ttg gac aaa | 663 |
|---|---|
| Gln Lys Arg Leu Lys Thr Val Leu Glu Leu Gln Tyr Val Leu Asp Lys | |
| 145                 150                 155 | |

| ttg gga gat gat gaa gtg cgg act gac ctg aaa caa ggt ttg aat gga | 711 |
|---|---|
| Leu Gly Asp Asp Glu Val Arg Thr Asp Leu Lys Gln Gly Leu Asn Gly | |
| 160                 165                 170 | |

| gtg cca ata ttg tcc gaa gag gag ttg tca ttg ttg gat gaa ttc tat | 759 |
|---|---|
| Val Pro Ile Leu Ser Glu Glu Glu Leu Ser Leu Leu Asp Glu Phe Tyr | |
| 175                 180                 185                 190 | |

| aag cta gta gac cct gaa cgg gac atg agc ttg agg ttg aat gaa cag | 807 |
|---|---|
| Lys Leu Val Asp Pro Glu Arg Asp Met Ser Leu Arg Leu Asn Glu Gln | |
| 195                 200                 205 | |

| tat gaa cat gcc tcc att cac ctg tgg gac ctg ctg gaa ggg aag gaa | 855 |
|---|---|
| Tyr Glu His Ala Ser Ile His Leu Trp Asp Leu Leu Glu Gly Lys Glu | |
| 210                 215                 220 | |

| aaa cct gta tgt gga acc acc tat aaa gtt cta aag gaa att gtt gag | 903 |
|---|---|
| Lys Pro Val Cys Gly Thr Thr Tyr Lys Val Leu Lys Glu Ile Val Glu | |
| 225                 230                 235 | |

```
cgt gtt ttt cag tca aac tac ttt gac agc acc cac aac cac cag aat      951
Arg Val Phe Gln Ser Asn Tyr Phe Asp Ser Thr His Asn His Gln Asn
    240                 245                 250 ggg ctg tgt gag gaa gaa gag gca gcc tca gca cct gca gtt gaa gac      999
Gly Leu Cys Glu Glu Glu Glu Ala Ala Ser Ala Pro Ala Val Glu Asp
255                 260                 265                 270 cag gta cct gaa gct gaa cct gag cca gca gaa gag tac act gag caa     1047
Gln Val Pro Glu Ala Glu Pro Glu Pro Ala Glu Glu Tyr Thr Glu Gln
                275                 280                 285 agt gaa gtt gaa tca aca gag tat gta aat aga cag ttc atg gca gaa     1095
Ser Glu Val Glu Ser Thr Glu Tyr Val Asn Arg Gln Phe Met Ala Glu
            290                 295                 300 aca cag ttc acc agt ggt gaa aag gag cag gta gat gag tgg aca gtt     1143
Thr Gln Phe Thr Ser Gly Glu Lys Glu Gln Val Asp Glu Trp Thr Val
        305                 310                 315 gaa acg gtt gag gtg gta aat tca ctc cag cag caa cct cag gct gca     1191
Glu Thr Val Glu Val Val Asn Ser Leu Gln Gln Gln Pro Gln Ala Ala
    320                 325                 330 tcc cct tca gta cca gag ccc cac tct ttg act cca gtg gct cag gca     1239
Ser Pro Ser Val Pro Glu Pro His Ser Leu Thr Pro Val Ala Gln Ala
335                 340                 345                 350 gat ccc ctt gtg aga aga cag cga gta caa gac ctt atg gca caa atg     1287
Asp Pro Leu Val Arg Arg Gln Arg Val Gln Asp Leu Met Ala Gln Met
                355                 360                 365 cag ggt ccc tat aat ttc ata cag gat tca atg ctg gat ttt gaa aat     1335
Gln Gly Pro Tyr Asn Phe Ile Gln Asp Ser Met Leu Asp Phe Glu Asn
            370                 375                 380 cag aca ctt gat cct gcc att gta tct gca cag cct atg aat cca aca     1383
Gln Thr Leu Asp Pro Ala Ile Val Ser Ala Gln Pro Met Asn Pro Thr
        385                 390                 395 caa aac atg gac atg ccc cag ctg gtt tgc cct cca gtt cat tct gaa     1431
Gln Asn Met Asp Met Pro Gln Leu Val Cys Pro Pro Val His Ser Glu
    400                 405                 410 tct aga ctt gct cag cct aat caa gtt cct gta caa cca gaa gcg aca     1479
Ser Arg Leu Ala Gln Pro Asn Gln Val Pro Val Gln Pro Glu Ala Thr
415                 420                 425                 430 cag gtt cct ttg gta tca tcc aca agt gag ggg tac aca gca tct caa     1527
Gln Val Pro Leu Val Ser Ser Thr Ser Glu Gly Tyr Thr Ala Ser Gln
                435                 440                 445 ccc ttg tac cag cct tct cat gct aca gag caa cga cca cag aag gaa     1575
Pro Leu Tyr Gln Pro Ser His Ala Thr Glu Gln Arg Pro Gln Lys Glu
            450                 455                 460 cca att gat cag att cag gca aca atc tct tta aat aca gac cag act     1623
Pro Ile Asp Gln Ile Gln Ala Thr Ile Ser Leu Asn Thr Asp Gln Thr
        465                 470                 475 aca gca tca tca tcc ctt cct gct gcg tct cag cct caa gta ttt cag     1671
Thr Ala Ser Ser Ser Leu Pro Ala Ala Ser Gln Pro Gln Val Phe Gln
    480                 485                 490 gct ggg aca agc aaa cct tta cat agc agt gga atc aat gta aat gca     1719
Ala Gly Thr Ser Lys Pro Leu His Ser Ser Gly Ile Asn Val Asn Ala
495                 500                 505                 510 gct cca ttc caa tcc atg caa acg gtt ttc aat atg aat gcc cca gtt     1767
Ala Pro Phe Gln Ser Met Gln Thr Val Phe Asn Met Asn Ala Pro Val
                515                 520                 525 cct cct gtt aat gaa cca gaa act tta aaa cag caa aat cag tac cag     1815
Pro Pro Val Asn Glu Pro Glu Thr Leu Lys Gln Gln Asn Gln Tyr Gln
            530                 535                 540 gcc agt tat aac cag agc ttt tct agt cag cct cac caa gta gaa caa     1863
Ala Ser Tyr Asn Gln Ser Phe Ser Ser Gln Pro His Gln Val Glu Gln
```

-continued

| | | | | | | | | | | | | | | | | |
|---|---|---|---|---|---|---|---|---|---|---|---|---|---|---|---|---|
| | | | | 545 | | | | | 550 | | | | | 555 | | |
| aca | gag | ctt | cag | caa | gaa | cag | ctt | caa | aca | gtg | gtt | ggc | act | tac | cat | 1911 |
| Thr | Glu | Leu | Gln | Gln | Glu | Gln | Leu | Gln | Thr | Val | Val | Gly | Thr | Tyr | His | |
| | 560 | | | | | 565 | | | | | 570 | | | | | |
| ggt | tcc | cca | gac | cag | tcc | cat | caa | gtg | act | ggt | aac | cac | cag | cag | cct | 1959 |
| Gly | Ser | Pro | Asp | Gln | Ser | His | Gln | Val | Thr | Gly | Asn | His | Gln | Gln | Pro | |
| 575 | | | | | 580 | | | | | 585 | | | | | 590 | |
| cct | cag | cag | aac | act | gga | ttt | cca | cgt | agc | aat | cag | ccc | tat | tac | aat | 2007 |
| Pro | Gln | Gln | Asn | Thr | Gly | Phe | Pro | Arg | Ser | Asn | Gln | Pro | Tyr | Tyr | Asn | |
| | | | | 595 | | | | | 600 | | | | | 605 | | |
| agt | cgt | ggt | gtg | tct | cgt | gga | ggc | tcc | cgt | ggt | gct | aga | ggc | ttg | atg | 2055 |
| Ser | Arg | Gly | Val | Ser | Arg | Gly | Gly | Ser | Arg | Gly | Ala | Arg | Gly | Leu | Met | |
| | | | 610 | | | | | 615 | | | | | 620 | | | |
| aat | gga | tac | cgg | ggc | cct | gcc | aat | gga | ttc | aga | gga | gga | tat | gat | ggt | 2103 |
| Asn | Gly | Tyr | Arg | Gly | Pro | Ala | Asn | Gly | Phe | Arg | Gly | Gly | Tyr | Asp | Gly | |
| | | 625 | | | | | 630 | | | | | 635 | | | | |
| tac | cgc | cct | tca | ttc | tct | aac | act | cca | aac | agt | ggt | tat | aca | cag | tct | 2151 |
| Tyr | Arg | Pro | Ser | Phe | Ser | Asn | Thr | Pro | Asn | Ser | Gly | Tyr | Thr | Gln | Ser | |
| | 640 | | | | | 645 | | | | | 650 | | | | | |
| cag | ttc | agt | gct | ccc | cgg | gat | tac | tct | ggc | tat | caa | cgg | gat | gga | tat | 2199 |
| Gln | Phe | Ser | Ala | Pro | Arg | Asp | Tyr | Ser | Gly | Tyr | Gln | Arg | Asp | Gly | Tyr | |
| 655 | | | | | 660 | | | | | 665 | | | | | 670 | |
| cag | cag | aat | ttc | aag | cga | ggc | tct | ggg | cag | agt | gga | cca | cgg | gga | gcc | 2247 |
| Gln | Gln | Asn | Phe | Lys | Arg | Gly | Ser | Gly | Gln | Ser | Gly | Pro | Arg | Gly | Ala | |
| | | | | 675 | | | | | 680 | | | | | 685 | | |
| cca | cga | ggt | aat | att | ttg | tgg | tgg | tga | tcctagctcc | | | | taagtggagc | | | 2294 |
| Pro | Arg | Gly | Asn | Ile | Leu | Trp | Trp | | | | | | | | | |
| | | | 690 | | | | | | | | | | | | | | ttctgttctg gccttggaag agctgttaat agtctgcatg ttaggaatac atttatcctt 2354 tccagacttg tgctaggga ttaaatgaaa tgctctgttt ctaaaactta atcttggacc 2414 caaattttaa tttttgaatg atttaatttt ccctgttact atataaactg tcttgaaaac 2474 tagaacatat tctcttctca gaaaaagtgt ttttccaact gaaaattatt tttcaggtcc 2534 taaaacctgc taaatgtttt taggaagtac ttactgaaac attttgtaa gacattttg 2594 gaatgagatt gaacatttat ataaatttat tattcctctt tcattttttt gaaacatgcc 2654 tattatattt tagggccaga caccctttaa tggccggata agccatagtt aacatttaga 2714 gaaccattta gaagtgatag aactaatgga atttgcaatg ccttttggac tctctattagt 2774 gatataaata tcaagttatt tctgactttt aaacaaaact cccaaattcc taacttattg 2834 agctatactt aaaaaaaatt acaggtttag agagtttttt gtttttcttt tactgttgga 2894 aaactacttc ccattttggc aggaagttaa cctatttaac aattagagct agcatttcat 2954 gtagtctgaa attctaaatg gttctctgat ttgagggagg ttaaacatca aacaggtttc 3014 ctctattggc cataacatgt ataaaatgtg tgttaaggag gaattacaac gtactttgat 3074 ttgaatacta gtagaaactg gccaggaaaa aggtacattt ttctaaaaat taatggatca 3134 cttgggaatt actgacttga ctagaagtat caaaggatgt ttgcatgtga atgtgggtta 3194 tgttctttcc caccttgtag catattcgat gaaagttgag ttaactgata gctaaaaatc 3254 tgttttaaca gcatgtaaaa agttatttta tctgttaaaa gtcattatac agttttgaat 3314 gttatgtagt ttcttttttaa cagtttaggt aataaggtct gttttcattc tggtgctttt 3374 attaattttg atagtatgat gttacttact actgaaatgt aagctagagt gtacactaga 3434 atgtaagctc catgagagca ggtaccttgt ctgtcttctc tgctgtatct attcccaacg 3494 cttgatgatg gtgcctggca catagtaggc actcaataaa tatttgttga atgaatgaa 3553

<210> SEQ ID NO 19
<211> LENGTH: 694
<212> TYPE: PRT
<213> ORGANISM: Homo sapiens

<400> SEQUENCE: 19

```
Met Pro Ser Ala Thr Ser His Ser Gly Ser Gly Ser Lys Ser Ser Gly
1               5                   10                  15

Pro Pro Pro Pro Ser Gly Ser Ser Ser Glu Ala Ala Gly Ala
            20                  25                  30

Gly Ala Ala Ala Pro Ala Ser Gln His Pro Ala Thr Gly Thr Gly Ala
        35                  40                  45

Val Gln Thr Glu Ala Met Lys Gln Ile Leu Gly Val Ile Asp Lys Lys
    50                  55                  60

Leu Arg Asn Leu Glu Lys Lys Gly Lys Leu Asp Asp Tyr Gln Glu
65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
            100                 105                 110

Gln Arg Ser Phe Met Ala Leu Ser Gln Asp Ile Gln Lys Thr Ile Lys
        115                 120                 125

Lys Thr Ala Arg Arg Glu Gln Leu Met Arg Glu Gly Ala Glu Gln Lys
130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175

Ile Leu Ser Glu Glu Glu Leu Ser Leu Leu Asp Glu Phe Tyr Lys Leu
            180                 185                 190

Val Asp Pro Glu Arg Asp Met Ser Leu Arg Leu Asn Glu Gln Tyr Glu
        195                 200                 205

His Ala Ser Ile His Leu Trp Asp Leu Leu Glu Gly Lys Glu Lys Pro
    210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
                245                 250                 255

Cys Glu Glu Glu Glu Ala Ala Ser Ala Pro Ala Val Gly Asp Gln Val
            260                 265                 270

Pro Glu Ala Glu Pro Glu Pro Ala Glu Glu Tyr Thr Glu Gln Ser Glu
        275                 280                 285

Val Glu Ser Thr Glu Tyr Val Asn Arg Gln Phe Met Ala Glu Thr Gln
    290                 295                 300

Phe Thr Ser Gly Glu Lys Glu Gln Val Asp Glu Trp Thr Val Glu Thr
305                 310                 315                 320

Val Glu Val Val Asn Ser Leu Gln Gln Gln Pro Gln Ala Ala Ser Pro
                325                 330                 335

Ser Val Pro Glu Pro His Ser Leu Thr Pro Val Ala Gln Ala Asp Pro
            340                 345                 350

Leu Val Arg Arg Gln Arg Val Gln Asp Leu Met Ala Gln Met Gln Gly
        355                 360                 365

Pro Tyr Asn Phe Ile Gln Asp Ser Met Leu Asp Phe Glu Asn Gln Thr
```

```
                    370                 375                 380
Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
                405                 410                 415

Leu Ala Gln Pro Asn Gln Val Pro Val Gln Pro Glu Ala Thr Gln Val
            420                 425                 430

Pro Leu Val Ser Ser Thr Ser Glu Gly Tyr Thr Ala Ser Gln Pro Leu
                435                 440                 445

Tyr Gln Pro Ser His Ala Thr Glu Gln Arg Pro Gln Lys Glu Pro Ile
            450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
                485                 490                 495

Thr Ser Lys Pro Leu His Ser Ser Gly Ile Asn Val Asn Ala Ala Pro
                500                 505                 510

Phe Gln Ser Met Gln Thr Val Phe Asn Met Asn Ala Pro Val Pro Pro
                515                 520                 525

Val Asn Glu Pro Glu Thr Leu Lys Gln Gln Asn Gln Tyr Gln Ala Ser
530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
                565                 570                 575

Pro Asp Gln Ser His Gln Val Thr Gly Asn His Gln Gln Pro Pro Gln
                580                 585                 590

Gln Asn Thr Gly Phe Pro Arg Ser Asn Gln Pro Tyr Tyr Asn Ser Arg
                595                 600                 605

Gly Val Ser Arg Gly Gly Ser Arg Gly Ala Arg Gly Leu Met Asn Gly
                610                 615                 620

Tyr Arg Gly Pro Ala Asn Gly Phe Arg Gly Gly Tyr Asp Gly Tyr Arg
625                 630                 635                 640

Pro Ser Phe Ser Asn Thr Pro Asn Ser Gly Tyr Thr Gln Ser Gln Phe
                645                 650                 655

Ser Ala Pro Arg Asp Tyr Ser Gly Tyr Gln Arg Asp Gly Tyr Gln Gln
                660                 665                 670

Asn Phe Lys Arg Gly Ser Gly Gln Ser Gly Pro Arg Gly Ala Pro Arg
                675                 680                 685

Gly Asn Ile Leu Trp Trp
                690

<210> SEQ ID NO 20
<211> LENGTH: 118
<212> TYPE: PRT
<213> ORGANISM: Artificial Sequence
<220> FEATURE:
<223> OTHER INFORMATION: Synthetic polypeptide derived from rabbit

<400> SEQUENCE: 20

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser His Ser
                20                  25                  30

Leu Gly Trp Val Arg Gln Ala Pro Gly Lys Gly Leu Glu Trp Ile Gly
```

35                  40                  45

Asp Ile Arg Ser Gly Gly Ser Ala Tyr Tyr Ala Asn Trp Ala Lys Gly
     50                  55                  60

Arg Phe Thr Ile Ser Arg Thr Ser Thr Thr Val Ala Leu Lys Met Thr
65                  70                  75                  80

Ser Leu Thr Thr Glu Asp Thr Ala Thr Tyr Phe Cys Thr Arg Thr Asn
                 85                  90                  95

Gly Pro Ser Asp Leu Thr Asn Arg Leu Asp Leu Trp Gly Gln Gly Thr
            100                 105                 110

Leu Val Thr Val Ser Ser
            115

<210> SEQ ID NO 21
<211> LENGTH: 112
<212> TYPE: PRT
<213> ORGANISM: Artificial Sequence
<220> FEATURE:
<223> OTHER INFORMATION: Synthetic polypeptide derived from rabbit

<400> SEQUENCE: 21

Gln Val Leu Thr Gln Thr Pro Ser Ser Val Ser Ala Ala Val Gly Gly
1               5                   10                  15

Thr Val Thr Ile Asn Cys Gln Ala Ser Gln Ser Leu Tyr Asn Asn Glu
            20                  25                  30

Asn Leu Ala Trp Phe Gln Gln Lys Pro Gly Gln Pro Pro Lys Arg Leu
        35                  40                  45

Ile Tyr Gly Ala Ser Thr Leu Ala Ser Gly Val Ser Ser Arg Phe Lys
    50                  55                  60

Gly Ser Gly Ser Gly Thr Gln Phe Thr Leu Thr Ile Gly Asp Val Gln
65                  70                  75                  80

Cys Asp Asp Ala Ala Ile Tyr Tyr Cys Leu Gly Glu Phe Ser Cys Gly
                85                  90                  95

Ser Ala Asp Cys Phe Ala Phe Gly Gly Gly Thr Glu Val Val Val Lys
            100                 105                 110

<210> SEQ ID NO 22
<211> LENGTH: 363
<212> TYPE: DNA
<213> ORGANISM: Homo sapiens

<400> SEQUENCE: 22
gaggtgcagc tcgtcgagag cggcggaggc ctcgtccaac tggaggcag cctgagactg      60 agttgcgccg cttccggctt cagcctgtcc agccactccc tcggctgggt gaggcaggcc    120
cctggcaagg gactggagtg gatcggcgat atccgcagcg gaggctccgc ttactatgcc    180
aactgggcta aggaaggtt caccatttcc cgggacaact ctaagaatac actgtatttg    240
caaatgaata gcttgcgcgc cgaggataca gccgtgtact ctgtacccg gacaaacgga    300 cccagcgacc tgaccaatag gctcgacctc tggggacagg gcacattggt gacagtgtcc    360
tca                                                                  363

<210> SEQ ID NO 23
<211> LENGTH: 363
<212> TYPE: DNA
<213> ORGANISM: Homo sapiens

<400> SEQUENCE: 23
gaggtgcagc tcgtcgagag cggcggaggc ctcgtccaac tggaggcag cctgagactg      60

```
agttgcgccg cttccggctt cagcctgtcc agccactccc tcggctgggt gaggcaggcc    120
cctggcaagg gactggagtg gatcggcgat atccgcagcg gaggctccgc ttactatgcc    180
aactgggcta agggaaggtt caccatttcc cgggacaaca gcaagaatac cctgtatttg    240
caaatgaata gcttgcgcgc cgaggataca gccgtgtact actgtacccg gacaaacgga    300
cccagcgacc tgaccaatag gctcgacctc tggggacagg gcacattggt gacagtgtcc    360
tca                                                                  363
```

<210> SEQ ID NO 24
<211> LENGTH: 360
<212> TYPE: DNA
<213> ORGANISM: Homo sapiens

<400> SEQUENCE: 24

```
cagagcctgg tcgagagcgg cggaggcctc gtgcaacccg gaggcagcct gcggctgagc    60
tgcgctgcca gcggcttttc cctctccagc cacagcctgg gatgggtcag gcaagcccct    120
ggcaaaggcc tcgagtggat tggcgatatc cggtccggag gcagcgccta ttacgctaac    180
tgggctaagg gaaggtttac catttcccgg accagctcca aaaacacagt gtatctgcaa    240
atgaattccc tgcgggccga agacacagcc gtctactttt gcacaaggac aaacggaccc    300
agcgacctca ccaataggct cgacctctgg ggacagggaa ccctcgtgac agtgtccagc    360
```

<210> SEQ ID NO 25
<211> LENGTH: 363
<212> TYPE: DNA
<213> ORGANISM: Homo sapiens

<400> SEQUENCE: 25

```
gaacagagcc tggtcgagag cggcggaggc ctcgtgcaac ccggaggcag cctgcggctg    60
agctgcgctg ccagcggctt ttccctctcc agccacagcc tgggatgggt caggcaagcc    120
cctggcaaag gcctcgagtg gattggcgat atccggtccg gaggcagcgc ctattacgct    180
aactgggcta agggaaggtt taccatttcc cgggataact ccaaaaacac actgtatctg    240
caaatgaatt ccctgcgggc cgaagacaca gccgtctact attgcacaag gacaaacgga    300
cccagcgacc tcaccaatag gctcgacctc tggggacagg gaaccctcgt gacagtgtcc    360
agc                                                                  363
```

<210> SEQ ID NO 26
<211> LENGTH: 339
<212> TYPE: DNA
<213> ORGANISM: Homo sapiens

<400> SEQUENCE: 26

```
gccatccaaa tgacacagag ccccagctcc ctctccgcca gcgtgggaga ccgggtgacc    60
atcaattgcc aggcttccca gtccctctac aataacgaaa acctcgcctg gttccaacag    120
aaacccggca aggtgcccaa gaggctcatc tacgagcca gcaccctggc ctccggagtg    180
tcctcccggt tctccggcag cggctctggc accgaattca cattgaccat tagcaacctg    240
cagcctgaga cttcgctac atactactgt ctggagagt tttcctgcgg cagcgccgat    300
tgcttcgcct ttggcggagg cacaaaggtc gagatcaaa                           339
```

<210> SEQ ID NO 27
<211> LENGTH: 339
<212> TYPE: DNA

<213> ORGANISM: Homo sapiens

<400> SEQUENCE: 27

| | |
|---|---|
| gagatcgtcc tgacacagag ccccagctcc ctctccgcca gcgtgggaga ccgggtgacc | 60 |
| atcaattgcc aggcttccca gtccctctac aataacgaaa acctcgcctg gttccaacag | 120 |
| aaacccggca aggtgcccaa gaggctcatc tacgagccag caccctggc ctccggagtg | 180 |
| tcctcccggt tctccggcag cggctctggc accgaattca cattgaccat tagcaacctg | 240 |
| cagcctgagg acttcgctac atactactgt ctgggagagt tttcctgcgg cagcgccgat | 300 |
| tgcttcgcct ttggcggagg cacaaaggtc gagatcaaa | 339 |

<210> SEQ ID NO 28
<211> LENGTH: 339
<212> TYPE: DNA
<213> ORGANISM: Homo sapiens

<400> SEQUENCE: 28

| | |
|---|---|
| gagcaggtcc tgacacagag ccccagctcc ctctccgcca gcgtgggaga ccgggtgacc | 60 |
| atcaattgcc aggcttccca gtccctctac aataacgaaa acctcgcctg gttccaacag | 120 |
| aaacccggca aggtgcccaa gaggctcatc tacgagccag caccctggc ctccggagtg | 180 |
| tcctcccggt tctccggcag cggctctggc accgaattca cattgaccat tagcaacctg | 240 |
| cagcctgagg acttcgctat ctactactgt ctgggagagt tttcctgcgg cagcgccgat | 300 |
| tgcttcgcct ttggcggagg cacaaaggtc gagatcaaa | 339 |

<210> SEQ ID NO 29
<211> LENGTH: 339
<212> TYPE: DNA
<213> ORGANISM: Homo sapiens

<400> SEQUENCE: 29

| | |
|---|---|
| gacattgtgc tcacccaatc cccttccagc ctgagcgcca gcgtgggaga ccgggtgaca | 60 |
| atcaattgcc aagccagcca gagcctgtat aacaatgaga atctggcttg gtttcagcaa | 120 |
| aagcctggca aagtgcctaa gcggctgatt tacgagccag caccctcgc cagcggcgtc | 180 |
| tccagcaggt tttccggatc cggatccgga accgaattca cactgacaat cagctccctc | 240 |
| cagtgtgagg atttcgctat ctattactgt ctggagagt tttcctgtgg cagcgccgat | 300 |
| tgcttttgcct ttggcggagg cacaaaggtc gagattaag | 339 |

<210> SEQ ID NO 30
<211> LENGTH: 336
<212> TYPE: DNA
<213> ORGANISM: Homo sapiens

<400> SEQUENCE: 30

| | |
|---|---|
| caagtgctca cccaatcccc ttccagcctg agcgccagcg tgggagaccg ggtgacaatc | 60 |
| aattgccaag ccagccagag cctgtataac aatgagaatc tggcttggtt tcagcaaaag | 120 |
| cctggcaaag tgcctaagcg gctgatttac ggagccagca ccctcgccag cggcgtctcc | 180 |
| agcaggtttt ccggatccgg atccggaacc gaattcacac tgacaatcag ctccctccag | 240 |
| tgtgaggatt tcgctatcta ttactgtctg ggagagtttt cctgtggcag cgccgattgc | 300 |
| tttgcctttg gcggaggcac aaaggtcgag attaag | 336 |

<210> SEQ ID NO 31
<211> LENGTH: 354

```
<212> TYPE: DNA
<213> ORGANISM: Artificial Sequence
<220> FEATURE:
<223> OTHER INFORMATION: Synthetic DNA derived from rabbit

<400> SEQUENCE: 31
cagtcgctgg aggagtccgg gggtcgcctg gtcacgcctg ggacacccct gacactcacc      60
tgcacagcct ctggattctc cctcagtagc cattcattgg gctgggtccg ccaggctcca     120
gggaaggggc tggaatggat cggagacatt aggagtggtg gtagcgcata ctacgcgaac     180
tgggcaaaag gccgattcac catctccaga acctcgacca cggtggctct gaagatgacc     240
agtctgacaa ccgaggacac ggccacctat ttctgtacca gaactaatgg tcccagtgat     300
ctgactaata ggttggatct ctggggccag ggcaccctgg tcaccgtctc ctca           354

<210> SEQ ID NO 32
<211> LENGTH: 336
<212> TYPE: DNA
<213> ORGANISM: Artificial Sequence
<220> FEATURE:
<223> OTHER INFORMATION: Synthetic DNA derived from rabbit

<400> SEQUENCE: 32
caagtactga cccagactcc atcctccgtg tctgcagctg tgggaggcac agtcaccatc      60
aactgccagg ccagtcagag tctttataat aacgaaaatt tagcctggtt tcagcagaaa     120
ccagggcagc ctcccaagcg cctgatctat ggtgcatcca ctctggcatc tggggtctca     180
tcgcggttca aaggcagtgg atctgggaca cagttcactc tcaccatcgg cgacgtgcag     240
tgtgacgatg ctgccattta ctattgtcta ggcgaattta gttgtggtag tgctgattgt     300
tttgctttcg gcggagggac cgaggtggtc gtcaaa                               336

<210> SEQ ID NO 33
<211> LENGTH: 330
<212> TYPE: PRT
<213> ORGANISM: Homo sapiens

<400> SEQUENCE: 33

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Leu Pro Glu Glu Lys Thr Ile Ser Lys Ala Lys Gly
    210                 215                 220

Gln Pro Arg Glu Pro Gln Val Tyr Thr Leu Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 34
<211> LENGTH: 330
<212> TYPE: PRT
<213> ORGANISM: Homo sapiens

<400> SEQUENCE: 34

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Glu Glu Lys Thr Ile Ser Lys Ala Lys Gly
    210             215                 220

Gln Pro Arg Glu Pro Gln Val Tyr Thr Leu Pro Pro Ser Arg Asp Glu
225             230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305             310                 315                 320

Gln Lys Ser Leu Ser Leu Ser Pro Gly Lys
                325                 330
```

PHARMACEUTICAL COMPOSITION FOR TREATMENT AND/OR PREVENTION OF CANCER

REFERENCE TO SEQUENCE LISTING SUBMITTED VIA EFS-WEB

This application includes an electronically submitted sequence listing in .txt format. The .txt file contains a sequence listing entitled "2016-06-03_1254-0582PUS1_ST25.txt" created on Jun. 3, 2016 and is 64,715 bytes in size. The sequence listing contained in this .txt file is part of the specification and is hereby incorporated by reference herein in its entirety.

TECHNICAL FIELD

The present invention relates to an antibody against CAPRIN-1 or a fragment thereof, and novel pharmaceutical use thereof as a therapeutic and/or preventive agent for a cancer, etc.

BACKGROUND ART

Cancers are diseases that account for the leading cause of death. The current treatment thereof consists principally of surgical therapy, which may be combined with radiation therapy and/or chemotherapy. In spite of the development of novel surgical techniques or the discovery of novel anticancer agents in recent years, the existing treatment of cancers has an insufficiently improved outcome, except for some cancers. With advances of molecular biology or cancer immunology, antibodies that specifically react with cancers, cancer antigens that are recognized by cytotoxic T cells, genes encoding such cancer antigens, and the like have been identified in recent years, raising expectations on specific cancer therapy targeting the cancer antigens.

Cytoplasmic-activation and proliferation-associated protein 1 (CAPRIN-1) has been known as an intracellular protein that is expressed upon activation or cell division of resting normal cells and forms cytoplasmic stress granules with intracellular RNAs to participate in the regulation of transport and translation of mRNAs. This protein has been found to be specifically expressed on the surface of cancer cells and is under study as a target of antibody drugs for cancer treatment (Patent Literatures 1 to 19).

CITATION LIST

Patent Literature

Patent Literature 1: WO2010/016526
Patent Literature 2: WO2011/096517
Patent Literature 3: WO2011/096528
Patent Literature 4: WO2011/096519
Patent Literature 5: WO2011/096533
Patent Literature 6: WO2011/096534
Patent Literature 7: WO2011/096535
Patent Literature 8: WO2013/018886
Patent Literature 9: WO2013/018894
Patent Literature 10: WO2013/018892
Patent Literature 11: WO2013/018891
Patent Literature 12: WO2013/018889
Patent Literature 13: WO2013/018883
Patent Literature 14: WO2013/125636
Patent Literature 15: WO2013/125654
Patent Literature 16: WO2013/125630
Patent Literature 17: WO2013/125640
Patent Literature 18: WO2013/147169
Patent Literature 19: WO2013/147176

SUMMARY OF INVENTION

Technical Problem

An object of the present invention is to produce an antibody that targets CAPRIN-1 specifically expressed on the surface of cancer cells and is superior in antitumor activity to conventional antibodies, and to provide use thereof as a therapeutic and/or preventive agent for a cancer.

Solution to Problem

Features of the present invention are as follows:

The present invention provides a pharmaceutical composition for the treatment and/or prevention of a cancer, comprising an antibody which comprises a heavy chain variable region comprising SEQ ID NOs: 1, 2, and 3 and a light chain variable region comprising SEQ ID NOs: 4, 5, and 6 and has immunological reactivity with a CAPRIN-1 protein, or a fragment thereof as an active ingredient.

In an embodiment thereof, the cancer is breast cancer, kidney cancer, pancreatic cancer, colorectal cancer, lung cancer, brain tumor, stomach cancer, uterine cancer, ovary cancer, prostate cancer, bladder cancer, esophagus cancer, leukemia, lymphoma, liver cancer, gallbladder cancer, sarcoma, mastocytoma, melanoma, adrenal cortex cancer, Ewing's tumor, Hodgkin's lymphoma, mesothelioma, multiple myeloma, testicle cancer, thyroid cancer, or head and neck cancer.

In another embodiment, the antibody is a human antibody, a humanized antibody, a chimeric antibody, a single-chain antibody, or a multispecific antibody (e.g., a bispecific antibody).

The present specification encompasses the contents described in the specification and/or drawings of Japanese Patent Application No. 2013-166164 on which the priority of the present application is based.

Advantageous Effects of Invention

The antibody against CAPRIN-1 according to the present invention damages cancer cells. Thus, the antibody against CAPRIN-1 according to the present invention is useful in the treatment and/or prevention of a cancer.

DESCRIPTION OF EMBODIMENTS

The antibody against a polypeptide of CAPRIN-1 used in the present invention can be evaluated for its antitumor activity, as mentioned later, by examining ex vivo whether or not to exhibit immunocyte-mediated cytotoxic activity against tumor cells expressing the polypeptide or by examining in vivo the inhibition of tumor growth in a cancer-bearing animal.

The antibody against CAPRIN-1 according to the present invention may be a monoclonal antibody or a polyclonal antibody and is preferably a monoclonal antibody. The antibody against CAPRIN-1 according to the present invention may be any type of antibody that can exert antitumor activity and includes, for example, recombinant antibodies (e.g., synthetic antibodies, multispecific antibodies (e.g., bispecific antibodies), humanized antibodies, chimeric antibodies, and single-chain antibodies (scFv)), human antibodies, and their antibody fragments (e.g., Fab, F(ab')$_2$, and Fv). These antibodies and fragments thereof can be prepared by methods generally known to those skilled in the art. When a subject is a human, a human antibody or a humanized antibody is desirable for circumventing or suppressing rejection.

The phrase "specifically binding to a CAPRIN-1 protein" means that the antibody specifically binds to the CAPRIN-1 protein without substantially binding to other proteins.

The subject according to the present invention, whose cancer is to be treated and/or prevented is a mammal such as a human, a pet animal, livestock, or a sport animal, and a preferred subject is a human.

Hereinafter, the preparation of the antigen, the preparation of the antibody, and the pharmaceutical composition according to the present invention will be described.

<Preparation of Antigen for Antibody Preparation>

A proteins or a fragment thereof used as a sensitizing antigen for obtaining the antibody against CAPRIN-1 according to the present invention is not limited by animal species serving as the origin thereof, including humans, dogs, cats, cattle, horses, mice, rats, and chickens. However, it is preferred to select the sensitizing antigen in view of compatibility with parent cells for use in cell fusion. In general, a mammal-derived protein is preferred. Particularly, a human-derived protein is preferred. For example, when CAPRIN-1 is human CAPRIN-1, the human CAPRIN-1 protein, a partial peptide thereof, cells expressing human CAPRIN-1, or the like can be used.

The nucleotide sequences and amino acid sequences of human CAPRIN-1 and homologs thereof can be obtained, for example, by making an access to GenBank (NCBI, USA) and using an algorithm such as BLAST or FASTA (Karlin and Altschul, Proc. Natl. Acad. Sci. USA, 90: 5873-5877, 1993, and Altschul et al., Nucleic Acids Res. 25: 3389-3402, 1997).

In the present invention, with reference to the nucleotide sequence (SEQ ID NO: 16 or 18) or amino acid sequence (SEQ ID NO: 17 or 19) of human CAPRIN-1, the target CAPRIN-1 is a nucleic acid or a protein consisting of a sequence having 70% to 100%, preferably 80% to 100%, more preferably 90% to 100%, further preferably 95% to 100%, for example, 97% to 100%, 98% to 100%, 99% to 100%, or 99.5% to 100% sequence identity to the nucleotide sequence or amino acid sequence of the ORF or mature portion of the reference (the amino acid sequences of SEQ ID NO: 17 and SEQ ID NO: 19 compared with each other differ in amino acid residues at and following position 690). In this context, the term "% sequence identity" means a percentage (%) of the number of identical amino acids (or bases) to the total number (including the number of gaps) of amino acids (or bases) when two sequences are aligned such that the maximum degree of similarity or identity can be achieved with or without introduced gaps.

The fragment of the CAPRIN-1 protein has a length ranging from the amino acid length of an epitope (antigenic determinant), which is the smallest unit recognized by the antibody, to less than the full length of the protein. The epitope refers to a polypeptide fragment having antigenicity or immunogenicity in mammals, preferably humans. Its smallest unit consists of approximately 7 to 12 amino acids, for example, 8 to 11 amino acids.

A polypeptide fragment comprising the aforementioned human CAPRIN-1 protein or a partial peptide thereof can be synthesized according to a chemical synthesis method, for example, an Fmoc (fluorenylmethyloxycarbonyl) or tBoc (t-butyloxycarbonyl) method (Seikagaku Jikken Koza 1 (Biochemical Experimentation Course 1 in English), the Japanese Biochemical Society ed., Protein Chemistry IV, Chemical Modification and Peptide Synthesis, Tokyo Kagaku Dojin Co., Ltd. (Japan), 1981). Also, the human CAPRIN-1 protein or the polypeptide fragment can be synthesized by a routine method using various commercially available peptide synthesizers. Alternatively, a polynucleotide encoding the polypeptide is prepared using a genetic engineering approach known in the art (Sambrook et al., Molecular Cloning, the 2nd edition. Current Protocols in Molecular Biology (1989), Cold Spring Harbor Laboratory Press: Ausubel et al., Short Protocols in Molecular Biology, the 3rd edition, A compendium of Methods from Current Protocols in Molecular Biology (1995). John Wiley & Sons; etc.), and this polynucleotide is incorporated into expression vectors, which are then transferred to host cells so that the polypeptide is produced in the host cells. In this way, the human CAPRIN-1 protein of interest or the polypeptide fragment thereof can be obtained.

The polynucleotide encoding the polypeptide can be readily prepared by a genetic engineering approach known in the art or a routine method using a commercially available nucleic acid synthesizer. For example, a DNA comprising the nucleotide sequence of human CAPRIN-1 gene can be prepared by PCR using a human chromosomal DNA or cDNA library as a template and a pair of primers designed so as to be able to amplify the nucleotide sequence. Reaction conditions for this PCR can be appropriately determined. Examples of the conditions can include, but are not limited to, 30 cycles each involving reaction steps consisting of 94° C. for 30 seconds (denaturation), 55° C. for 30 seconds to 1 minute (annealing), and 72° C. for 2 minutes (elongation) using thermostable DNA polymerase (e.g., Taq polymerase or Pfu polymerase) and a $Mg^{2+}$-containing PCR buffer, followed by reaction at 72° C. for 7 minutes. The PCR approach, conditions, etc., are described in, for example, Ausubel et al., Short Protocols in Molecular Biology, the 3rd edition, A Compendium of Methods from Current Protocols in Molecular Biology (1995), John Wiley & Sons (particularly, Chapter 15).

Also, appropriate probes or primers can be prepared on the basis of information on the nucleotide sequence of the CAPRIN-1 gene and the amino acid sequence of the CAPRIN-1 protein, and used in the screening of, for example, a human cDNA library, to isolate the desired DNA. It is preferred that the cDNA library should be produced from cells, organs, or tissues expressing the CAPRIN-1 protein. Examples of such cells or tissues include cells or tissues derived from the testis as well as from cancers or tumors such as leukemia, breast cancer, lymphoma, brain tumor, lung cancer, pancreatic cancer, colorectal cancer, kidney cancer, stomach cancer, uterine cancer, ovary cancer, prostate cancer, bladder cancer, esophagus cancer, sarcoma, mastocytoma, liver cancer, gallbladder cancer, melanoma, adrenal cortex cancer, Ewing's tumor, Hodgkin's lymphoma, mesothelioma, multiple myeloma, testicle cancer, thyroid cancer, and head and neck cancer. These procedures, including the preparation of probes or primers, the construction of a cDNA library, the screening of the cDNA library, and the cloning of the gene of interest, are known to those skilled in the art and can be carried out according to methods described in, for example, Sambrook et al., Molecular Cloning, the 2nd edition, Current Protocols in Molecular Biology (1989), and Ausubel et al. (ibid.). The DNA encoding the human CAPRIN-1 protein or the partial peptide thereof can be obtained from the DNA thus obtained.

The host cells to receive the expression vectors may be any cell capable of expressing the polypeptide. Examples of prokaryotic cells include, but are not limited to, *E. coli*. Examples of eukaryotic cells include, but are not limited to: mammalian cells such as monkey kidney cells COS1 and Chinese hamster ovary cells CHO; a human embryonic kidney cell line HEK293; a mouse embryonic skin cell line NIH3T3; yeast cells such as budding yeast and fission yeast cells; silkworm cells; and *Xenopus* egg cells.

In the case of using prokaryotic cells as the host cells, expression vectors having an origin that permits replication in the prokaryotic cells, a promoter, a ribosomal binding site, a multicloning site, a terminator, a drug resistance gene, an auxotrophic complementary gene, etc., are used as the expression vectors. Examples of expression vectors for *E. coli* can include pUC series, pBluescript II, pET expression systems, and pGEX expression systems. The DNA encoding the polypeptide is incorporated into such expression vectors, and prokaryotic host cells can be transformed with these vectors, followed by the culture of the obtained transformants so that the polypeptide encoded by the DNA is expressed in the prokaryotic host cells. In this respect, the polypeptide may be expressed as a fusion protein with another protein.

In the case of using eukaryotic cells as the host cells, expression vectors for eukaryotic cells having a promoter, a splicing region, a poly(A) addition site, etc., are used as the expression vectors. Examples of such expression vectors can include pKA1, pCDM8, pSVK3, pMSG, pSVL, pBK-CMV, pBK-RSV, EBV, pRS, pcDNA3, and pYES2 vectors. In the same way as above, the DNA encoding the polypeptide is incorporated into such expression vectors, and eukaryotic host cells can be transformed with these vectors, followed by the culture of the obtained transformants so that the polypeptide encoded by the DNA is expressed in the eukaryotic host cells. In the case of using expression vectors such as pIND/V5-His, pFLAG-CMV-2, pEGFP-N1, or pEGFP-C1, the polypeptide can be expressed as various fusion proteins tagged with His tag (e.g., $(His)_6$ to $(His)_{10}$), FLAG tag, myc tag, HA tag, GFP, or the like.

The transfer of the expression vectors to the host cells can employ a well-known method such as electroporation, a calcium phosphate method, a liposome method, a DEAE dextran method, microinjection, viral infection, lipofection, or binding with cell-penetrating peptides.

Separation treatments known in the art can be carried out in combination for isolating and purifying the polypeptide of interest from the host cells. Examples thereof include, but are not limited to, treatment with a denaturant (e.g., urea) or a surfactant, ultrasonication, enzymatic digestion, salting-out, solvent fractionation and precipitation, dialysis, centrifugation, ultrafiltration, gel filtration, SDS-PAGE, isoelectric focusing electrophoresis, ion-exchange chromatography, hydrophobic chromatography, affinity chromatography, and reverse-phase chromatography.

The antigen thus prepared can be used as a sensitizing antigen as mentioned later for producing the antibody according to the present invention.

<Structure of Antibody>

Antibodies (immunoglobulins) are usually heteromultimeric glycoproteins each comprising at least two heavy chains and two light chains. The immunoglobulins, except for IgM, are heterotetrameric glycoproteins of approximately 150 kDa each composed of two identical light (L) chains and two identical heavy (H) chains. Typically, each light chain is connected to a heavy chain via a single covalent disulfide bond, though the number of disulfide bonds varies among heavy chains of different immunoglobulin isotypes. Each heavy chain and light chain also have an intrachain disulfide bond. Each heavy chain has a variable domain (VH region) at one end, followed by a series of constant regions. Each light chain has a variable domain (VL region) at one end and has a single constant region at the other end. The light chain constant region is aligned with the first heavy chain constant region, while the light chain variable domain is aligned with the heavy chain variable domain. Particular regions called complementarity-determining regions (CDRs) in the antibody variable domains exhibit specific variability and impart binding specificity to the antibody. Moietys relatively conserved in the variable regions are called framework regions (FRs). The complete heavy chain and light chain variable domains each has a structure in which four framework regions are connected via three complementarity-determining regions, i.e., a structure in which FR1, CDR1, FR2, CDR2, FR3, CDR3, and FR4 are connected in this order from the N-terminus. These three complementarity-determining regions in the heavy chain are called CDRH1, CDRH2, and CDRH3 in this order from the N-terminus thereof. Likewise, the complementarity-determining regions in the light chain are called CDRL1, CDRL2, and CDRL3. CDRH3 is most important for the binding specificity of the antibody for its antigen. In addition, CDRs in each chain are kept close to each other by the framework regions and contribute to the formation of an antigen-binding site in the antibody, together with the complementarity-determining regions derived from the other chain. The constant regions do not directly contribute to antibody-antigen binding, but exhibit various effector functions, for example, involvement in antibody-dependent cellular cytotoxicity (ADCC), phagocytosis (ADCP) mediated by binding to an Fcγ receptor, half-life/clearance rates mediated by a neonatal Fc receptor (FcRn), and complement-dependent cytotoxicity (CDC) mediated by a C1q component in the complement cascade.

<Preparation of Antibody>

The anti-CAPRIN-1 antibody according to the present invention means an antibody having immunological reactivity with a full-length CAPRIN-1 protein or a fragment thereof.

In this context, the "immunological reactivity" means the property of the antibody binding to the CAPRIN-1 antigen (a full-length CAPRIN-1 protein or a partial polypeptide thereof) in vivo. Via such binding to CAPRIN-1, the antibody of the present invention exerts the function of damaging (e.g., killing, suppressing, or regressing) tumor cells. The antibody of the present invention can damage tumor, for example, breast cancer, kidney cancer, pancreatic cancer, colorectal cancer (e.g., colon cancer), lung cancer, brain tumor, stomach cancer, uterine cancer, ovary cancer, prostate cancer, bladder cancer, esophagus cancer, leukemia, lymphoma, liver cancer, gallbladder cancer, sarcoma, mastocytoma, melanoma, adrenal cortex cancer, Ewing's tumor, Hodgkin's lymphoma, mesothelioma, multiple myeloma, testicle cancer, thyroid cancer, or head and neck cancer through binding to the CAPRIN-1 protein.

The antibody of the present invention is not particularly limited, preferably, as long as the antibody is a monoclonal antibody. The antibody of the present invention includes synthetic antibodies, multispecific antibodies (e.g., diabodies and triabodies), human antibodies, humanized antibodies, chimeric antibodies, single-chain antibodies, antibody fragments (e.g., Fab, $F(ab')_2$, and Fv), and the like. Also, the antibody is an immunoglobulin molecule of any class, for example, IgG, IgE, IgM, IgA, IgD, or IgY, or of any subclass, for example, IgG1, IgG2, IgG3, IgG4, IgA1, or IgA2.

The antibody may be further modified by deglycosylation, acetylation, formylation, amidation, phosphorylation, PEGylation, or the like, in addition to glycosylation.

Hereinafter, preparation examples of various monoclonal antibodies will be given.

For example, a breast cancer cell line SK-BR-3 expressing CAPRIN-1 is administered to a mouse for immunization. The spleen is extracted from this mouse. After separation of spleen cells, the cells are fused with mouse myeloma cells. Clones producing antibodies having a cancer cell growth inhibitory effect are selected from among the obtained fusion cells (hybridomas). The hybridomas producing monoclonal antibodies having a cancer cell growth inhibitory effect are isolated, and these hybridomas are cultured. The antibody of the present invention can be prepared by purification from the culture supernatant according to a general affinity purification method.

The monoclonal antibody-producing hybridomas may be prepared, for example, as follows: first, animals are immunized with the sensitizing antigen according to a method known in the art. This immunization method generally involves intraperitoneally or subcutaneously injecting the sensitizing antigen to mammals. Specifically, the sensitizing antigen diluted with or suspended in PBS (phosphate-buffered saline), physiological saline, or the like into an appropriate amount is mixed, if desired, with an appropriate amount of a conventional adjuvant, for example, a Freund's complete adjuvant. After emulsification, the resulting emulsion is administered to each mammal several times every 4 to 21 days. Alternatively, an appropriate carrier may be used for the immunization with the sensitizing antigen.

After confirmation of a rise in the level of the desired antibody in the serum of the mammal thus immunized, immunocytes are collected from the mammal and subjected to cell fusion. Preferred examples of the immunocytes particularly include spleen cells.

Mammalian myeloma cells are used as partner parent cells to be fused with the immunocytes. Various cell lines known in the art, for example, P3U1 (P3-X63Ag8U1), P3 (P3x63Ag8.653) (J. Immunol. (1979) 123, 1548-1550), P3x63Ag8U.1 (Current Topics in Microbiology and Immunology (1978) 81, 1-7), NS-1 (Kohler. G. and Milstein, C. Eur. J. Immunol. (1976) 6, 511-519), MPC-1 (Margulies. D. H. et al., Cell (1976) 8, 405-415), SP2/0 (Shulman, M. et al., Nature (1978) 276, 269-270), FO (deSt. Groth, S. F. et al., J. Immunol. Methods (1980) 35, 1-21), S194 (Trowbridge, I. S. J. Exp. Med. (1978) 148, 313-323), R210 (Galfre, G. et al., Nature (1979) 277, 131-133), 240E-1, 240E-W and 240E-W2 are preferably used as the myeloma cells.

The cell fusion between the immunocytes and the myeloma cells can be carried out basically according to a method known in the art, for example, the method of Kohler and Milstein (Kohler, G. and Milstein, C. Methods Enzymol. (1981) 73, 3-46).

More specifically, the cell fusion is carried out, for example, in the presence of a cell fusion promoter in a conventional nutrient medium. For example, polyethylene glycol (PEG) or hemagglutinating virus of Japan (HVJ) is used as the fusion promoter. If desired, an auxiliary such as dimethyl sulfoxide may be further added for use in order to enhance fusion efficiency.

The ratio between the immunocytes and the myeloma cells used can be arbitrarily set. For example, an RPMI1640 medium or a MEM medium suitable for the growth of the myeloma cell lines, or a conventional medium for use in this type of cell culture can be used as the medium for use in the cell fusion. In addition, a serum supplement such as fetal calf serum (FCS) may be used in combination with the medium.

For the cell fusion, the immunocytes and the myeloma cells are well mixed in a predetermined amount of the medium. A PEG solution (average molecular weight: for example, approximately 1000 to 6000) preheated to approximately 37° C. is usually added to the mixture at a concentration of 30 to 60% (w/v) and mixed therewith to form the hybridomas of interest. Subsequently, it is preferred to remove cell fusion agents or the like unfavorable for the growth of the hybridomas by repeating the procedures of sequentially adding an appropriate medium and removing the supernatant by centrifugation.

The hybridomas thus obtained are cultured in a conventional selective medium, for example, a HAT medium (medium containing hypoxanthine, aminopterin, and thymidine) for selection. This culture in the HAT medium is continued for a period (usually, several days to several weeks) sufficient for the death of cells (non-fused cells) other than the hybridomas of interest. Subsequently, hybridomas producing the antibody of interest are screened for and cloned as single clones by a conventional limiting dilution method.

In addition to such obtainment of the hybridomas by the immunization of non-human animals with the antigen, hybridomas producing human antibodies having the desired activity (e.g., cell growth inhibitory activity) may be obtained by sensitizing human lymphocytes, for example, EB virus-infected human lymphocytes, with the protein, protein-expressing cells, or lysates thereof in vitro and fusing the sensitized lymphocytes with human-derived myeloma cells capable of dividing permanently, for example, U266 (Registration No. TIB196).

The monoclonal antibody-producing hybridomas thus prepared can be subcultured in a conventional medium and can also be stored for a long period in liquid nitrogen.

Specifically, the desired antigen or cells expressing the desired antigen are used as a sensitizing antigen in immunization according to a conventional immunization method. The obtained immunocytes are fused with parent cells known in the art according to a conventional cell fusion method. Monoclonal antibody-producing cells (hybridomas) can be screened for by a conventional screening method to prepare the antibody of interest.

The antigen can be prepared according to, for example, a method using animal cells (JP Patent Publication (Kohyo) No. 2007-530068 A (2007)) or a method using baculovirus (e.g., International Publication No. WO98/46777). When the antigen has low immunogenicity, this antigen can be bound to an immunogenic macromolecule such as albumin for immunization. The antigen may be administered together with an adjuvant for immunization.

Alternatively, the antibody of the present invention may be obtained as a gene recombinant antibody produced using a gene recombination technique which involves: cloning a gene of the antibody from a hybridoma; incorporating the antibody gene into appropriate vectors; and transferring the vectors into hosts (see, e.g., Carl, A. K. Borrebaeck, James, W. Larrick, THERAPEUTIC MONOCLONAL ANTIBODIES, Published in the United Kingdom by MACMILLAN PUBLISHERS LTD, 1990). Specifically, variable region (V region) cDNAs of the antibody are synthesized from the mRNAs of the hybridoma using reverse transcriptase. After obtainment of DNAs encoding the V regions of the antibody of interest, the DNAs are ligated with DNAs encoding the desired antibody constant regions (C regions). The resulting ligation products are incorporated into expression vectors. Alternatively, the antibody V region-encoding DNAs may be incorporated into expression vectors containing antibody C region DNAs. These DNAs are incorporated into the expression vectors so as to be expressed under the control of expression control regions, for example, an enhancer and a promoter. Next, host cells can be transformed with the resulting expression vectors and allowed to express the antibody.

The anti-CAPRIN-1 antibody of the present invention is preferably a monoclonal antibody. The monoclonal antibody includes human monoclonal antibodies, non-human animal monoclonal antibodies (e.g., mouse, rat, rabbit, and chicken monoclonal antibodies), chimeric monoclonal antibodies, and the like. The monoclonal antibody may be prepared by culturing hybridomas obtained by the fusion between spleen cells from non-human mammals (e.g., mice, human antibody-producing mice, chickens, or rabbits) immunized with the CAPRIN-1 protein or a fragment thereof and myeloma cells. The chimeric antibody is an antibody prepared from a combination of sequences derived from different animals and is, for example, an antibody composed of heavy chain and light chain variable regions of a mouse antibody and heavy chain and light chain constant regions of a human antibody. The chimeric antibody can be prepared using a method known in the art and is obtained, for example, by: ligating DNAs encoding the antibody V regions with DNAs encoding the human antibody C regions; incorporating the resulting ligation products into expression vectors; and transferring the vectors into hosts for antibody production.

In Examples mentioned later, a plurality of humanized monoclonal antibodies and a human-rabbit chimeric monoclonal antibody were prepared and confirmed to have a strong antitumor effect. All of these monoclonal antibodies have a heavy chain variable region (VH region) comprising CDR1 represented by the amino acid sequence of SEQ ID NO: 1, CDR2 represented by the amino acid sequence of SEQ ID NO: 2, and CDR3 represented by the amino acid sequence of SEQ ID NO: 3, and a light chain variable region (VL region) comprising CDR1 represented by the amino acid sequence of SEQ ID NO: 4, CDR2 represented by the amino acid sequence of SEQ ID NO: 5, and CDR3 represented by the amino acid sequence of SEQ ID NO: 6. These monoclonal antibodies include humanized antibody #0 consisting of a VH region having the amino acid sequence of SEQ ID NO: 7 and a VL region having the amino acid sequence of SEQ ID NO: 11, humanized antibody #1 consisting of a VH region having the amino acid sequence of SEQ ID NO: 8 and a VL region having the amino acid sequence of SEQ ID NO: 11, humanized antibody #2 consisting of a VH region having the amino acid sequence of SEQ ID NO: 8 and a VL region having the amino acid sequence of SEQ ID NO: 12, humanized antibody #3 consisting of a VH region having the amino acid sequence of SEQ ID NO: 8 and a VL region having the amino acid sequence of SEQ ID NO: 13, humanized antibody #4 consisting of a VH region having the amino acid sequence of SEQ ID NO: 7 and a VL region having the amino acid sequence of SEQ ID NO: 12, humanized antibody #5 consisting of a VH region having the amino acid sequence of SEQ ID NO: 7 and a VL region having the amino acid sequence of SEQ ID NO: 13, humanized antibody #6 consisting of a VH region having the amino acid sequence of SEQ ID NO: 7 and a VL region having the amino acid sequence of SEQ ID NO: 15, humanized antibody #7 consisting of a VH region having the amino acid sequence of SEQ ID NO: 8 and a VL region having the amino acid sequence of SEQ ID NO: 15, humanized antibody #8 consisting of a VH region having the amino acid sequence of SEQ ID NO: 9 and a VL region having the amino acid sequence of SEQ ID NO: 15, humanized antibody #9 consisting of a VH region having the amino acid sequence of SEQ ID NO: 10 and a VL region having the amino acid sequence of SEQ ID NO: 14, humanized antibody #10 consisting of a VH region having the amino acid sequence of SEQ ID NO: 10 and a VL region having the amino acid sequence of SEQ ID NO: 15, and a human-rabbit chimeric antibody consisting of a VH region having the amino acid sequence of SEQ ID NO: 20 and a VL region having the amino acid sequence of SEQ ID NO: 21.

The humanized antibody, also called reshaped human antibody, is an engineered antibody. The humanized antibody is constructed by grafting complementarity-determining regions of a human antibody with complementarity-determining regions of an antibody derived from an immunized animal. A general gene recombination approach therefor is also known.

Specifically, DNA sequences designed so as to link complementarity-determining regions of, for example, a mouse, rabbit, or chicken antibody, and framework regions of a human antibody are synthesized by PCR from several prepared oligonucleotides having terminal portions overlapping with each other. The obtained DNAs are ligated with DNAs encoding human antibody constant regions. Subsequently, the resulting ligation products are incorporated into expression vectors, which are then transferred to hosts for antibody production to obtain the antibody of interest (see European Patent Application Publication No. EP239400 and International Publication No. WO96/02576). The framework regions of a human antibody connected via the complementarity-determining regions are selected such that the complementarity-determining regions form a favorable antigen-binding site. If necessary, amino acids in the framework regions of antibody variable regions may be substituted such that the complementarity-determining regions of the resulting reshaped human antibody form an appropriate antigen-binding site (Sato K. et al., Cancer Research 1993, 53: 851-856). In addition, these framework regions may be replaced with framework regions derived from various human antibodies (see International Publication No. WO99/51743).

For preparing the chimeric antibody or the humanized antibody, amino acids in variable regions (e.g., FRs) or constant regions may be substituted, for example, by other amino acids.

The amino acid substitution is the substitution of one or more, for example, less than 15, less than 10, 8 or less, 7 or less, 6 or less, 5 or less, 4 or less, 3 or less, or 2 or less amino acids, preferably 1 to 9 amino acids. The substituted antibody should be functionally equivalent to an unsubstituted antibody.

In this context, the phrase "functionally equivalent" means that an antibody concerned has biological or biochemical activity similar to that of the antibody of the present invention, specifically, the antibody concerned has the function of damaging tumor and essentially causes no rejection when applied to humans, for example. Examples of such activity can include cell growth inhibitory activity and binding activity.

An amino acid substitution method which involves introducing a mutation into a polypeptide is well known to those skilled in the art as a method for preparing a polypeptide functionally equivalent to a certain polypeptide. For example, those skilled in the art can appropriately introduce amino acid substitution into the antibody of the present invention using site-directed mutagenesis (Hashimoto-Gotoh, T. et al., (1995) Gene 152, 271-275; Zoller, M J., and Smith, M. (1983) Methods Enzymol. 100, 468-500; Kramer, W. et al., (1984) Nucleic Acids Res. 12, 9441-9456; Kramer, W. and Fritz, H J., (1987) Methods Enzymol. 154, 350-367; Kunkel, T A., (1985) Proc. Natl. Acad. Sci. USA. 82, 488-492; Kunkel (1988) Methods Enzymol. 85, 2763-2766) or the like, thereby preparing an antibody functionally equivalent to the antibody of the present invention.

In the case of introducing amino acid substitution, the substitution is desirably conservative amino acid substitution. The conservative amino acid substitution is the substitution between amino acids similar in properties such as charge, side chains, polarity, and aromaticity. The amino acids can be classified in terms of similar properties into, for example: basic amino acids (arginine, lysine, and histidine); acidic amino acids (aspartic acid and glutamic acid); uncharged polar amino acids (glycine, asparagine, glutamine, serine, threonine, cysteine, and tyrosine); nonpolar amino acids (leucine, isoleucine, alanine, valine, proline, phenylalanine, tryptophan, and methionine); branched amino acids (leucine, valine, and isoleucine); and aromatic amino acids (phenylalanine, tyrosine, tryptophan, and histidine).

Examples of modified antibodies can include antibodies bound with various molecules such as polyethylene glycol (PEG). In the modified antibody of the present invention, the substance to be bound is not limited. In order to obtain such a modified antibody, the obtained antibody can be chemically modified. A method therefor has already been established in the art.

The antibody that recognizes a CAPRIN-1 protein or a CAPRIN-1 fragment polypeptide can be obtained by a method generally known to those skilled in the art. The antibody can be obtained by, for example, a method which involves determining an epitope of the CAPRIN-1 protein recognized by an anti-CAPRIN-1 antibody by a conventional method (e.g., epitope mapping or an epitope identification method mentioned later) and preparing an antibody using a polypeptide having an amino acid sequence contained in the epitope as an immunogen, or a method which involves determining an epitope for an antibody prepared by a conventional method and selecting an antibody that recognizes the same epitope as that for an anti-CAPRIN-1 antibody.

The antibody of the present invention is an antibody having immunological reactivity with CAPRIN-1, an antibody that specifically recognizes CAPRIN-1, or an antibody that specifically binds to CAPRIN-1 and exhibits cytotoxic activity against a cancer or a tumor growth inhibitory effect. It is preferred that the antibody should be an antibody having a structure so as to cause little or no rejection in recipient animals. Examples of such antibodies include human antibodies, humanized antibodies, chimeric antibodies (e.g., human-rabbit chimeric antibodies), single-chain antibodies, and bispecific antibodies when the recipient animals are humans. These antibodies are recombinant antibodies having heavy chain and light chain variable regions derived from a human antibody, having heavy chain and light chain variable regions comprising complementarity-determining regions (CDR1, CDR2, and CDR3) derived from a non-human animal antibody and framework regions (FR1, FR2, FR3, and FR4) derived from a human antibody, or having heavy chain and light chain variable regions derived from a non-human animal antibody and heavy chain and light chain constant regions derived from a human antibody. Preferred antibodies are the former two antibodies.

These recombinant antibodies can be prepared as follows: a DNA encoding the monoclonal antibody (e.g., a human, mouse, rat, rabbit, or chicken monoclonal antibody) against human CAPRIN-1 is cloned from antibody-producing cells such as hybridomas, and this is used as a template in RT-PCR or the like to prepare DNAs encoding the light chain and heavy chain variable regions of the antibody. The respective sequences of the light chain and heavy chain variable regions, the respective sequences of CDR1, CDR2, and CDR3 in each region, or the respective sequences of FR1, FR2, FR3, and FR4 in each region can be determined on the basis of, for example, the Kabat EU numbering system (Kabat et al., Sequences of Proteins of Immunological Interest, 5th Ed. Public Health Service, National Institute of Health, Bethesda, Md. (1991)).

Such a DNA encoding each of these variable regions or a DNA encoding each complementarity-determining region is further prepared using a gene recombination technique (Sambrook et al., Molecular Cloning A Laboratory Manual, Cold Spring Harbor Laboratory Press (1989)) or a DNA synthesizer. In this context, the human monoclonal antibody-producing hybridomas can be prepared by immunizing human antibody-producing animals (e.g., mice) with human CAPRIN-1 and then fusing spleen cells excised from the immunized animals with myeloma cells. Aside from this, DNAs encoding human antibody-derived light chain or heavy chain variable and constant regions are prepared, if necessary, using a gene recombination technique or a DNA synthesizer.

For the humanized antibody, the CDR coding sequences in the DNA encoding the human antibody-derived light chain or heavy chain variable region can be substituted by corresponding CDR coding sequences of a non-human animal (e.g., mouse, rat, rabbit, or chicken)-derived antibody to thereby prepare a humanized antibody-encoding DNA. In the case of, for example, a humanized antibody in which CDR coding sequences derived from a human antibody is substituted by corresponding CDR coding sequences derived from a mouse antibody, each variable region is constituted by human FR1, mouse CDR1, human FR2, mouse CDR2, human FR3, mouse CDR4, and human FR4 in this order from the N-terminus.

For the chimeric antibody, the DNA encoding the light chain or heavy chain variable region of a non-human animal (e.g., mouse, rat, rabbit, or chicken)-derived antibody can be ligated with the DNA encoding a light chain or heavy chain constant region derived from a human antibody to prepare a chimeric antibody-encoding DNA.

In the case of the single-chain antibody, this antibody refers to an antibody comprising a heavy chain variable region and a light chain variable region linearly linked via a linker. A DNA encoding the single-chain antibody can be prepared by ligating a DNA encoding the heavy chain variable region, a DNA encoding the linker, and a DNA encoding the light chain variable region. In this context, both of the heavy chain variable region and the light chain variable region are derived from a human antibody or derived from a human antibody having complementarity-determining regions alone substituted by complementarity-determining regions of a non-human animal (e.g., mouse, rat, rabbit, or chicken)-derived antibody. The linker consists of 12 to 19 amino acids. Examples thereof include $(G_4S)_3$ consisting of 15 amino acids (G.-B. Kim et al., Protein Engineering Design and Selection 2007, 20 (9): 425-432).

In the case of the bispecific antibody (e.g., diabody), this antibody refers to an antibody capable of specifically binding to two different epitopes. A DNA encoding the bispecific antibody can be prepared by ligating, for example, a DNA encoding heavy chain variable region A, a DNA encoding light chain variable region B, a DNA encoding heavy chain variable region B, and a DNA encoding light chain variable region A in this order (provided that the DNA encoding a light chain variable region B and the DNA encoding a heavy chain variable region B are ligated via a DNA encoding a linker as described above). In this context, all of the heavy chain variable regions and the light chain variable regions are derived from a human antibody or derived from a human antibody having complementarity-determining regions alone substituted by complementarity-determining regions of a non-human animal (e.g., mouse, rat, rabbit, or chicken)-derived antibody.

The recombinant DNAs thus prepared can be incorporated into one or more appropriate vectors, which are then transferred to host cells (e.g., mammalian cells, yeast cells, and insect cells) so that the DNAs are (co)expressed to produce the recombinant antibody of interest (P. J. Delves, ANTIBODY PRODUCTION ESSENTIAL TECHNIQUES, 1997 WILEY; P. Shepherd and C. Dean, Monoclonal Antibodies, 2000 OXFORD UNIVERSITY PRESS; J. W. Goding, Monoclonal Antibodies: principles and practice, 1993 ACADEMIC PRESS).

Examples of the antibody of the present invention prepared by any of the methods described above include the following antibodies (a) to (l) comprising a heavy chain variable region comprising SEQ ID NOs: 1, 2, and 3 and a light chain variable region comprising SEQ ID NOs: 4, 5, and 6, obtained in Examples mentioned later:

(a) an antibody constituted by a heavy chain variable region of SEQ ID NO: 8 and a light chain variable region of SEQ ID NO: 15, (b) an antibody constituted by a heavy chain variable region of SEQ ID NO: 10 and a light chain variable region of SEQ ID NO: 15, (c) an antibody constituted by a heavy chain variable region of SEQ ID NO: 7 and a light chain variable region of SEQ ID NO: 15, (d) an antibody constituted by a heavy chain variable region of SEQ ID NO: 8 and a light chain variable region of SEQ ID NO: 13, (e) an antibody constituted by a heavy chain variable region of SEQ ID NO: 7 and a light chain variable region of SEQ ID NO: 12, (f) an antibody constituted by a heavy chain variable region of SEQ ID NO: 8 and a light chain variable region of SEQ ID NO: 12, (g) an antibody constituted by a heavy chain variable region of SEQ ID NO: 7 and a light chain variable region of SEQ ID NO: 13, (h) an antibody constituted by a heavy chain variable region of SEQ ID NO: 10 and a light chain variable region of SEQ ID NO: 14, (i) an antibody constituted by a heavy chain variable region of SEQ ID NO: 8 and a light chain variable region of SEQ ID NO: 11, (j) an antibody constituted by a heavy chain variable region of SEQ ID NO: 7 and a light chain variable region of SEQ ID NO: 11, (k) an antibody constituted by a heavy chain variable region of SEQ ID NO: 9 and a light chain variable region of SEQ ID NO: 15, and (l) an antibody constituted by a heavy chain variable region of SEQ ID NO: 20 and a light chain variable region of SEQ ID NO: 21.

In this context, the amino acid sequences represented by SEQ ID NOs: 1, 2, and 3 correspond to CDR1, CDR2, and CDR3, respectively, of the heavy chain variable region of the rabbit antibody, and the amino acid sequences represented by SEQ ID NOs: 4, 5, and 6 correspond to CDR1, CDR2, and CDR3, respectively, of the light chain variable region of the rabbit antibody.

The humanized antibody, the chimeric antibody, the single-chain antibody, or the bispecific antibody of the present invention is, for example, any of the following antibodies (i) to (xiv):

(i) an antibody comprising a heavy chain variable region comprising the amino acid sequences of SEQ ID NOs: 1, 2, and 3 and the amino acid sequences of human antibody-derived framework regions, or substituted forms thereof, and a light chain variable region comprising the amino acid sequences of SEQ ID NOs: 4, 5, and 6 and the amino acid sequences of human antibody-derived framework regions, or substituted forms thereof, (ii) an antibody comprising a heavy chain variable region comprising the amino acid sequences of SEQ ID NOs: 1, 2, and 3 and the amino acid sequences of human antibody-derived framework regions, or substituted forms thereof and a heavy chain constant region comprising a human antibody-derived amino acid sequence, and a light chain variable region comprising the amino acid sequences of SEQ ID NOs: 4, 5, and 6 and the amino acid sequences of human antibody-derived framework regions, or substituted forms thereof and a light chain constant region comprising a human antibody-derived amino acid sequence, (iii) an antibody comprising a heavy chain variable region comprising the amino acid sequence of SEQ ID NO: 8 and a heavy chain constant region comprising a human antibody-derived amino acid sequence, and a light chain variable region comprising the amino acid sequence of SEQ ID NO: 15 and a light chain constant region comprising a human antibody-derived amino acid sequence, (iv) an antibody comprising a heavy chain variable region comprising the amino acid sequence of SEQ ID NO: 10 and a heavy chain constant region comprising a human antibody-derived amino acid sequence, and a light chain variable region comprising the amino acid sequence of SEQ ID NO: 15 and a light chain constant region comprising a human antibody-derived amino acid sequence, (v) an antibody comprising a heavy chain variable region comprising the amino acid sequence of SEQ ID NO: 7 and a heavy chain constant region comprising a human antibody-derived amino acid sequence, and a light chain variable region comprising the amino acid sequence of SEQ ID NO: 15 and a light chain constant region comprising a human antibody-derived amino acid sequence, (vi) an antibody comprising a heavy chain variable region comprising the amino acid sequence of SEQ ID NO: 8 and a heavy chain constant region comprising a human antibody-derived amino acid sequence, and a light chain variable region comprising the amino acid sequence of SEQ ID NO: 13 and a light chain constant region comprising a human antibody-derived amino acid sequence, (vii) an antibody comprising a heavy chain variable region comprising the amino acid sequence of SEQ ID NO: 7 and a heavy chain constant region comprising a human antibody-derived amino acid sequence, and a light chain variable region comprising the amino acid sequence of SEQ ID NO: 12 and a light chain constant region comprising a human antibody-derived amino acid sequence, (viii) an antibody comprising a heavy chain variable region comprising the amino acid sequence of SEQ ID NO: 8 a heavy chain constant region comprising a human antibody-derived amino acid sequence, and a light chain variable region comprising the amino acid sequence of SEQ ID NO: 12 and a light chain constant region comprising a human antibody-derived amino acid sequence, (ix) an antibody comprising a heavy chain variable region comprising the amino acid sequence of SEQ ID NO: 7 and a heavy chain constant region comprising a human antibody-derived amino acid sequence, and a light chain variable region comprising the amino acid sequence of SEQ ID NO: 13 and a light chain constant region comprising a human antibody-derived amino acid sequence, (x) an antibody comprising a heavy chain variable region comprising the amino acid sequence of SEQ ID NO: 10 and a heavy chain constant region comprising a human antibody-derived amino acid sequence, and a light chain variable region comprising the amino acid sequence of SEQ ID NO: 14 and a light chain constant region comprising a human antibody-derived amino acid sequence, (xi) an antibody comprising a heavy chain variable region comprising the amino acid sequence of SEQ ID NO: 8 and a heavy chain constant region comprising a human antibody-derived amino acid sequence, and a light chain variable region comprising the amino acid sequence of SEQ ID NO: 11 and a light chain constant region comprising a human antibody-derived amino acid sequence, (xii) an antibody comprising a heavy chain variable region comprising the amino acid sequence of SEQ ID NO: 7 and a heavy chain constant region comprising a human antibody-derived amino acid sequence, and a light chain variable region comprising the amino acid sequence of SEQ ID NO: 11 and a light chain constant region comprising a human antibody-derived amino acid sequence, (xiii) an antibody comprising a heavy chain variable region comprising the amino acid sequence of SEQ ID NO: 9 and a heavy chain constant region comprising a human antibody-derived amino acid sequence, and a light chain variable region comprising the amino acid sequence of SEQ ID NO: 15 and a light chain constant region comprising a human antibody-derived amino acid sequence, and (xiv) an antibody comprising a heavy chain variable region comprising the amino acid sequence of SEQ ID NO: 20 and a heavy chain constant region comprising a human antibody-derived amino acid sequence, and a light chain variable region comprising the amino acid sequence of SEQ ID NO: 21 and a light chain constant region comprising a human antibody-derived amino acid sequence.

The sequences of framework regions of the human antibody heavy chain and light chain constant and variable regions are available from, for example, NCBI (USA; GenBank, UniGene, etc.). For example, the following sequences can be referred to: Registration No. J00228 for a human IgG1 heavy chain constant region; Registration No. J00230 for a human IgG2 heavy chain constant region; Registration No. X03604 for a human IgG3 heavy chain constant region; Registration No. K01316 for a human IgG4 heavy chain constant region; Registration Nos. V00557, X64135, X64133, etc., for a human light chain κ constant region; and Registration Nos. X64132, X64134, etc., for a human light chain λ constant region.

Preferably, these antibodies have cytotoxic activity and can thereby exert an antitumor effect (or antitumor activity).

The aforementioned antibodies may each have the substitution, deletion, or addition of one or several amino acids in a complementarity-determining region sequence, a framework region sequence, and/or a constant region sequence, as long as the resulting antibody has such specificity that it can specifically recognize CAPRIN-1. In this context, the term "several" means preferably 1 to 9.

The affinity constant Ka ($k_{on}/k_{off}$) of the antibody of the present invention for a CAPRIN-1 protein or a fragment thereof is preferably at least $5 \times 10^8$ M$^{-1}$, at least $10^9$ M$^{-1}$, at least $5 \times 10^9$ M$^{-1}$, at least $10^{10}$ M$^{-1}$, at least $5 \times 10^{10}$ M$^{-1}$, at least $10^{11}$ M$^{-1}$, at least $5 \times 10^{11}$ M$^{-1}$, at least $10^{12}$ M$^{-1}$, at least $10^{13}$ M$^{-1}$, or at least $10^{14}$ M$^{-1}$.

One mechanism underlying the antitumor effect of the antibody of the present invention on CAPRIN-1-expressing cancer cells is the antibody-dependent cellular cytotoxicity (ADCC) of effector cells against the CAPRIN-1-expressing cells. The antitumor activity of the antibody of the present invention through ADCC can be enhanced by substituting one or several amino acids in the heavy chain constant region of the antibody of the present invention or by removing fucose added to N-acetylglucosamine in a N-glycoside-linked sugar chain attached to the heavy chain constant region. The antitumor activity of the antibody of the present invention through ADCC can be further enhanced by combining the amino acid substitution and fucose removal of the heavy chain constant region.

Such an antibody lacking fucose added to N-acetylglucosamine in a N-glycoside-linked sugar chain attached to the heavy chain constant region according to the present invention may be used alone or may be a composition with a fucosylated antibody. It is preferred that the antibody composition should be composed mainly of the antibody lacking fucose.

The antibody in which one or several amino acids in the heavy chain constant region are substituted can be prepared with reference to, for example, International Publication No. WO2004/063351, International Publication No. WO2011/120135, U.S. Pat. No. 8,388,955, International Publication No. WO2011/005481, U.S. Pat. No. 6,737,056, and International Publication No. WO2005/063351. The antibody lacking fucose added to N-acetylglucosamine in a N-glycoside-linked sugar chain in the heavy chain constant region, or cells producing the antibody can be prepared with reference to, for example, U.S. Pat. No. 6,602,684, European Patent No. 1914244, and U.S. Pat. No. 7,579,170. The composition of the antibody lacking fucose added to N-acetylglucosamine in a N-glycoside-linked sugar chain attached to the heavy chain constant region, and the fucosylated antibody, or cells producing the composition can be prepared with reference to, for example, U.S. Pat. No. 8,642,292.

The antibody of the present invention can be conjugated with an antitumor agent. The conjugation of the antibody with the antitumor agent can be carried out via a spacer having a group (e.g., a succinimidyl group, a formyl group, a 2-pyridyldithio group, a maleimidyl group, an alkoxycarbonyl group, or a hydroxy group) reactive with an amino group, a carboxyl group, a hydroxy group, a thiol group, or the like.

Examples of the antitumor agent include the following antitumor agents publicly known in literatures, etc.: paclitaxel, doxorubicin, daunorubicin, cyclophosphamide, methotrexate, 5-fluorouracil, thiotepa, busulfan, improsulfan, piposulfan, benzodopa, carboquone, meturedopa, uredopa, altretamine, triethylenemelamine, triethylenephosphoramide, triethylenethiophosphoramide, trimethylolomelamine, bullatacin, bullatacinone, camptothecin, bryostatin, callystatin, cryptophycin 1, cryptophycin 8, dolastatin, duocarmycin, eleutherobin, pancratistatin, sarcodictyin, spongistatin, chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, calicheamicin, dynemicin, clodronate, esperamicin, aclacinomycin, actinomycin, authramycin, azaserine, bleomycin, cactinomycin, carabicin, carminomycin, carzinophilin, chromomycin, dactinomycin, detorbicin, 6-diazo-5-oxo-L-norleucine, Adriamycin, epirubicin, esorubicin, idarubicin, marcellomycin, mitomycin C, mycophenolic acid, nogalamycin, olivomycin, peplomycin, potfiromycin, puromycin, quelamycin, rodorubicin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, androgens (e.g., calusterone, dromostanolone propionate, epitiostanol, mepitiostane, and testolactone), aminoglutethimide, mitotane, trilostane, frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, epothilone, etoglucid, lentinan, lonidamine, maytansine, ansamitocin, mitoguazone, mitoxantrone, mopidanmol, nitraerine, pentostatin, phenamet, pirarubicin, losoxantrone, podophyllinic acid, 2-ethylhydrazide, procarbazine, razoxane, rhizoxin, schizophyllan, spirogermanium, tenuazonic acid, triaziquone, roridin A, anguidine, urethane, vindesine, dacarbazine, mannomustine, mitobronitol, mitolactol, pipobroman, gacytosine, docetaxel, chlorambucil, gemcitabine, 6-thioguanine, mercaptopurine, cisplatin, oxaliplatin, carboplatin, vinblastine, etoposide, ifosfamide, mitoxantrone, vincristine, vinorelbine, novantrone, teniposide, edatrexate, daunomycin, aminopterin, Xeloda, ibandronate, irinotecan, topoisomerase inhibitors, difluoromethylomithine (DMFO), retinoic acid, capecitabine, and pharmaceutically acceptable salts and derivatives thereof.

When the antibody is an antibody conjugated with an antitumor agent, a method for evaluating whether to exert antitumor activity can involve, for example, for the mouse-derived anti-CAPRIN-1 antibody, reacting a drug-attached secondary antibody binding to a mouse antibody together therewith to evaluate ex vivo the antitumor effect on human cancer cells. This evaluation can be conducted using, for example, an anti-human IgG antibody (Hum-ZAP (Advanced Targeting Systems, Inc.)), which is a second immunotoxin bound with saporin.

Alternatively, the antibody of the present invention can be administered in combination with an antitumor agent to thereby produce a higher therapeutic effect. This approach is adaptable to a patient with a CAPRIN-1-expressing cancer either before or after surgical treatment. This approach can be applied, particularly after surgery, to a CAPRIN-1-expressing cancer, which has been treated conventionally with an antitumor agent alone, to produce higher prevention of cancer recurrence or prolongation of survival time.

For example, any of the antitumor agents described above can be used as the antitumor agent for use in the combined administration with the antibody of the present invention. Particularly, cyclophosphamide, paclitaxel, docetaxel, or vinorelbine is preferably used.

Alternatively, the antibody of the present invention may be bound to a radioisotope publicly known in literatures, etc., such as $^{211}$At, $^{131}$I, $^{125}$I, $^{90}$Y, $^{186}$Re, $^{188}$Re, $^{153}$SM, $^{212}$Bi, $^{32}$P, $^{175}$Lu, $^{176}$Lu, $^{89}$Sr, $^{64}$Cu, or $^{111}$In (Hideo Saji, YAKUGAKU ZASSHI 128 (3) 323-332, 8 (2008), Jpn). A radioisotope effective for the treatment or diagnosis of tumor is desirable. Such a radioisotope is also included in the antitumor agent according to the present invention.

<Antitumor Effect>

The antitumor effect of the anti-CAPRIN-1 antibody used in the present invention on CAPRIN-1-expressing cancer cells is considered to take place under the following mechanism or the like: the antibody-dependent cellular cytotoxicity (ADCC) of effector cells against the CAPRIN-1-expressing cells mentioned above and the antibody-dependent cellular phagocytosis (ADCP) of the CAPRIN-1-expressing cells. However, the scope of the present invention is not intended to be limited by this mechanism.

Thus, the activity of the anti-CAPRIN-1 antibody used in the present invention can be evaluated, as specifically shown below in Examples, by measuring ex vivo the ADCC activity or the ADCP activity against CAPRIN-1-expressing cancer cells.

The anti-CAPRIN-1 antibody used in the present invention binds to the CAPRIN-1 protein on cancer cells and exhibits an antitumor effect through the activity or the like. Thus, the anti-CAPRIN-1 antibody of the present invention is presumably useful in the treatment or prevention of a cancer. Specifically, the present invention provides a pharmaceutical composition for the treatment and/or prevention of a cancer, comprising the anti-CAPRIN-1 antibody as an active ingredient. The anti-CAPRIN-1 antibody used for the purpose of administration to human bodies (antibody therapy) is preferably a human antibody or a humanized antibody for reducing immunogenicity.

An anti-CAPRIN-1 antibody with higher binding affinity for the CAPRIN-1 protein on the surface of cancer cells exerts stronger antitumor activity. Thus, the antibody of the present invention has high binding affinity for the CAPRIN-1 protein and can therefore be expected to have a stronger antitumor effect. Accordingly, the antibody of the present invention is adaptable to a pharmaceutical composition intended for the treatment and/or prevention of a cancer. Such high binding affinity of the antibody of the present invention is preferably at least $5 \times 10^8$ M$^{-1}$, at least $10^9$ M$^{-1}$, at least $5 \times 10^9$ M$^{-1}$, at least $10^{10}$ M$^{-1}$, at least $5 \times 10^{10}$ M$^{-1}$, at least $10^{11}$ M$^{-1}$, at least $5 \times 10^{11}$ M$^{-1}$, at least $10^{12}$ M$^{-1}$, at least $10^{13}$ M$^{-1}$, or at least $10^{14}$ M$^{-1}$, in terms of an association constant (affinity constant) Ka ($k_{on}/k_{off}$), as described above.

<Binding to Antigen-Expressing Cell>

The ability of the antibody to bind to CAPRIN-1 can be determined by use of binding assay using, for example, ELISA, Western blot, immunofluorescence, and flow cytometry analysis, as described in Examples.

<Immunohistochemical Staining>

The antibody that recognizes CAPRIN-1 can be used in immunohistochemistry by a method well known to those skilled in the art. The antibody that recognizes CAPRIN-1 can be tested for its reactivity with CAPRIN-1, for example, using a paraformaldehyde- or acetone-fixed frozen section or a paraformaldehyde-fixed and paraffin-embedded section of a tissue obtained from a patient during surgical treatment or a tissue obtained from an animal carrying a xenograft tissue inoculated with a cell line expressing CAPRIN-1 either spontaneously or after transfection.

For immunohistochemical staining, the antibody reactive with CAPRIN-1 can be stained by various methods. For example, the antibody can be visualized through reaction with a horseradish peroxidase-conjugated goat anti-mouse antibody, goat anti-rabbit antibody, or goat anti-chicken antibody.

<Pharmaceutical Composition and Method for Treating and/or Preventing Cancer>

The target of the pharmaceutical composition for the treatment and/or prevention of a cancer of the present invention is not particularly limited as long as the target is cancer (cells) expressing a CAPRIN-1 gene.

The terms "tumor" and "cancer" used in the present specification mean malignant neoplasm and are used interchangeably with each other.

The cancer targeted in the present invention may be any cancer expressing the CAPRIN-1 protein on the cell membrane surface. The cancer is preferably breast cancer, kidney cancer, pancreatic cancer, colorectal cancer, lung cancer, brain tumor, stomach cancer, uterine cancer, ovary cancer, prostate cancer, bladder cancer, esophagus cancer, leukemia, lymphoma, liver cancer, gallbladder cancer, sarcoma, mastocytoma, melanoma, adrenal cortex cancer, Ewing's tumor, Hodgkin's lymphoma, mesothelioma, multiple myeloma, testicle cancer, thyroid cancer, or head and neck cancer as mentioned above.

More specifically, examples of these cancers include, but are not limited to, breast adenocarcinoma, complex-type breast adenocarcinoma, malignant mixed tumor of the mammary gland, intraductal papillary adenocarcinoma, lung adenocarcinoma, squamous cell cancer, small-cell cancer, large-cell cancer, glioma which is tumor of neuroepithelial tissue, glioblastoma, neuroblastoma, ependymoma, neuronal tumor, embryonal neuroectodermal tumor, neurilemmoma, neurofibroma, meningioma, chronic lymphocytic leukemia, gastrointestinal lymphoma, alimentary lymphoma, small to medium cell-type lymphoma, cecal cancer, ascending colon cancer, descending colon cancer, transverse colon cancer, sigmoid colon cancer, rectal cancer, epithelial ovarian cancer, germ cell tumor, stromal cell tumor, pancreatic ductal carcinoma, invasive pancreatic ductal carcinoma, pancreatic adenocarcinoma, acinar cell carcinoma, adenosquamous carcinoma, giant cell tumor, intraductal papillary-mucinous neoplasm, mucinous cystic neoplasm, pancreatoblastoma, islet-cell adenoma. Frants tumor, serous cystadenocarcinoma, solid-pseudopapillary tumor, gastrinoma, glucagonoma, insulinoma, multiple endocrine neoplasia type-1 (Wermer's syndrome), nonfunctional islet cell tumor, somatostatinoma, VIPoma, uterine cervix cancer, uterine body cancer, fibrosarcoma, sarcoma of bones or joints, Ewing's sarcoma, Wilms tumor, hepatoblastoma, soft tissue sarcoma, acute leukemia, chronic leukemia, spinal cord tumor, malignant soft tissue tumor, teratoma group tumor, and head and neck cancer including hypopharynx cancer, oropharynx cancer, tongue cancer, epipharynx cancer, oral cancer, lip cancer, sinus cancer, and throat cancer.

The recipient subjects (patients) are preferably mammals, for example, mammals including primates, pet animals, livestock, and sport animals and are particularly preferably humans, dogs, and cats.

In the case of using the antibody of the present invention as a pharmaceutical composition, the pharmaceutical composition can be formulated by a method generally known to those skilled in the art. For example, the pharmaceutical composition can be used in the form of a parenteral injection of an aseptic solution or suspension with water or any other pharmaceutically acceptable liquid. For example, the pharmaceutical composition may be formulated with the antibody mixed in a unit dosage form required for generally accepted pharmaceutical practice, in appropriate combination with pharmacologically acceptable carriers or media, specifically, sterilized water, physiological saline, a plant oil, an emulsifier, a suspending agent, a surfactant, a stabilizer, a flavoring agent, an excipient, a vehicle, a preservative, a binder, etc. The amount of the active ingredient in such a preparation is determined such that an appropriate dose within the prescribed range can be achieved.

An aseptic composition for injection can be formulated according to conventional pharmaceutical practice using a vehicle such as injectable distilled water.

Examples of aqueous solutions for injection include physiological saline, isotonic solutions containing glucose and other adjuvants, for example, D-sorbitol, D-mannose, D-mannitol, and sodium chloride. These solutions may be used in combination with an appropriate solubilizer, for example, an alcohol (specifically, ethanol) or a polyalcohol (e.g., propylene glycol and polyethylene glycol), or a nonionic surfactant, for example, Polysorbate 80™ or HCO-60.

Examples of oily solutions include sesame oil and soybean oil. These solutions may be used in combination with benzyl benzoate or benzyl alcohol as a solubilizer. The solutions may be further mixed with a buffer (e.g., a phosphate buffer solution and a sodium acetate buffer solution), a soothing agent (e.g., procaine hydrochloride), a stabilizer (e.g., benzyl alcohol and phenol), and an antioxidant. The injection solutions thus prepared are usually charged into appropriate ampules.

The pharmaceutical composition of the present invention is administered orally or parenterally, preferably parenterally. Specific examples of its dosage forms include injections, intranasal administration agents, transpulmonary administration agents, and percutaneous administration agents. Examples of the injections include intravenous injection, intramuscular injection, intraperitoneal injection, and subcutaneous injection, through which the pharmaceutical composition can be administered systemically or locally.

Also, the administration method can be appropriately selected depending on the age, weight, sex, symptoms, etc., of a patient. The dose of a pharmaceutical composition containing the antibody or a polynucleotide encoding the antibody can be selected within a range of, for example, 0.0001 to 1000 mg/kg of body weight per dose. Alternatively, the dose can be selected within a range of, for example, 0.001 to 100000 mg/body of a patient, though the dose is not necessarily limited to these numeric values. Although the dose and the administration method vary depending on the weight, age, sex, symptoms, etc., of a patient, those skilled in the art can appropriately select the dose and the method.

The pharmaceutical composition comprising the antibody of the present invention or the fragment thereof can be administered to a subject to treat and/or prevent a cancer, preferably breast cancer, kidney cancer, pancreatic cancer, colorectal cancer, lung cancer, brain tumor, stomach cancer, uterine cancer, ovary cancer, prostate cancer, bladder cancer, esophagus cancer, leukemia, lymphoma, liver cancer, gallbladder cancer, sarcoma, mastocytoma, melanoma, adrenal cortex cancer, Ewing's tumor, Hodgkin's lymphoma, mesothelioma, multiple myeloma, testicle cancer, thyroid cancer, or head and neck cancer.

The present invention further encompasses a method for treating and/or preventing a cancer, comprising administering the pharmaceutical composition of the present invention in combination with the antitumor agent as exemplified above or a pharmaceutical composition comprising the antitumor agent to a subject. The antibody of the present invention or the fragment thereof may be administered simultaneously with or separately from the antitumor agent to the subject. In the case of separate administration, either of their pharmaceutical compositions may be administered first or later. Their dosing intervals, doses, administration routes, and the number of doses can be appropriately selected by a specialist. In the case of simultaneous administration, the dosage form also includes, for example, a pharmaceutical composition formulated by mixing the antibody of the present invention or the fragment thereof and the antitumor agent in a pharmacologically acceptable carrier (or medium). The above descriptions about prescription, formulation, administration routes, doses, cancers, etc., as to the pharmaceutical compositions and dosage forms containing the antibody of the present invention are also applicable to any of the pharmaceutical compositions and dosage forms containing the antitumor agent.

Thus, the present invention also provides a combination drug product for the treatment and/or prevention of a cancer, comprising the pharmaceutical composition of the present invention and a pharmaceutical composition comprising the antitumor agent as exemplified above, and a method for treating and/or preventing a cancer, comprising administering the combination drug product. The present invention also provides a pharmaceutical composition for the treatment and/or prevention of a cancer, comprising the antibody of the present invention or the fragment thereof and the antitumor agent together with a pharmacologically acceptable carrier.

<Polypeptide and DNA>

The present invention further provides a DNA encoding the antibody of the present invention, a DNA encoding the heavy chain or the light chain of the antibody, and a DNA encoding the heavy chain or light chain variable region of the antibody. Such DNAs include, in the case of the antibody (a), for example, a DNA encoding a heavy chain variable region, comprising nucleotide sequences encoding the amino acid sequences of SEQ ID NOs: 1, 2, and 3, and a DNA encoding a light chain variable region, comprising nucleotide sequences encoding the amino acid sequences of SEQ ID NOs: 4, 5, and 6.

Since the complementarity-determining regions encoded by the DNAs having these sequences are regions that determine the specificity of the antibody, sequences encoding the other regions (i.e., constant regions and framework regions) of the antibody may be sequences derived from a different antibody. In this context, the different antibody also includes an antibody derived from a non-human organism, but is preferably one derived from a human from the viewpoint of reduction in adverse reaction. Specifically, for the DNAs mentioned above, it is preferred that regions encoding the respective framework regions of the heavy chain and the light chain and each constant region should comprise nucleotide sequences encoding the corresponding amino acid sequences derived from a human antibody.

Further examples of the DNA encoding the antibody of the present invention include a DNA encoding a heavy chain variable region, comprising a nucleotide sequence encoding the amino acid sequence of SEQ ID NO: 8, and a DNA in which a region encoding a light chain variable region comprises a nucleotide sequence encoding the amino acid sequence of SEQ ID NO: 15. In this context, an example of the nucleotide sequence encoding the amino acid sequence of SEQ ID NO: 8 is the nucleotide sequence of SEQ ID NO: 23. Also, an example of the nucleotide sequence encoding the amino acid sequence of SEQ ID NO: 15 is the nucleotide sequence of SEQ ID NO: 30. For these DNAs, it is also preferred that regions encoding the respective constant regions of the heavy chain and the light chain should comprise nucleotide sequences encoding the corresponding amino acid sequences derived from a human antibody.

These antibody DNAs can be obtained by, for example, the method mentioned above or the following method: first, total RNA is prepared from the hybridoma related to the antibody of the present invention using a commercially available RNA extraction kit, and cDNA is synthesized with reverse transcriptase using random primers or the like. Subsequently, the cDNA encoding the antibody is amplified by PCR using, as primers, oligonucleotides having sequences respectively conserved in the respective variable regions of a known mouse antibody heavy chain gene and light chain gene. Sequences encoding constant regions can be obtained by amplifying known sequences by PCR. The nucleotide sequence of the resulting DNA can be determined by a routine method, for example, by integration into a plasmid or a phage for sequencing.

The present invention further provides polypeptides and DNAs described in the following (i) to (xv) related to the antibodies (i) to (xiv):

(i) a heavy chain CDR polypeptide selected from the group consisting of the amino acid sequences represented by SEQ ID NOs: 1, 2, and 3, and a DNA encoding the polypeptide, (ii) a light chain CDR polypeptide selected from the amino acid sequences represented by SEQ ID NOs: 4, 5, and 6, and a DNA encoding the polypeptide, (iii) a polypeptide comprising the amino acid sequences of SEQ ID NO: 8 or SEQ ID NO: 15, and a DNA encoding the polypeptide, for example, a DNA comprising the nucleotide sequences of SEQ ID NO: 23 or SEQ ID NO: 30, respectively, (iv) a polypeptide comprising the amino acid sequences of SEQ ID NO: 10 or SEQ ID NO: 15, and a DNA encoding the polypeptide, for example, a DNA comprising the nucleotide sequences of SEQ ID NO: 25 or SEQ ID NO: 30, respectively, (v) a polypeptide comprising the amino acid sequences of SEQ ID NO: 7 or SEQ ID NO: 15, and a DNA encoding the polypeptide, for example, a DNA comprising the nucleotide sequences of SEQ ID NO: 22 or SEQ ID NO: 30, respectively, (vi) a polypeptide comprising the amino acid sequences of SEQ ID NO: 8 or SEQ ID NO: 13, and a DNA encoding the polypeptide, for example, a DNA comprising the nucleotide sequences of SEQ ID NO: 23 or SEQ ID NO: 28, respectively, (vii) a polypeptide comprising the amino acid sequences of SEQ ID NO: 7 or SEQ ID NO: 12, and a DNA encoding the polypeptide, for example, a DNA comprising the nucleotide sequences of SEQ ID NO: 22 or SEQ ID NO: 27, respectively, (viii) a polypeptide comprising the amino acid sequences of SEQ ID NO: 8 or SEQ ID NO: 12, and a DNA encoding the polypeptide, for example, a DNA comprising the nucleotide sequences of SEQ ID NO: 23 or SEQ ID NO: 27, respectively, (ix) a polypeptide comprising the amino acid sequences of SEQ ID NO: 7 or SEQ ID NO: 13, and a DNA encoding the polypeptide, for example, a DNA comprising the nucleotide sequences of SEQ ID NO: 22 or SEQ ID NO: 28, respectively, (x) a polypeptide comprising the amino acid sequences of SEQ ID NO: 10 or SEQ ID NO: 14, and a DNA encoding the polypeptide, for example, a DNA comprising the nucleotide sequences of SEQ ID NO: 25 or SEQ ID NO: 29, respectively, (xi) a polypeptide comprising the amino acid sequences of SEQ ID NO: 8 or SEQ ID NO: 11, and a DNA encoding the polypeptide, for example, a DNA comprising the nucleotide sequences of SEQ ID NO: 23 or SEQ ID NO: 26, respectively, (xii) a polypeptide comprising the amino acid sequences of SEQ ID NO: 7 or SEQ ID NO: 11, and a DNA encoding the polypeptide, for example, a DNA comprising the nucleotide sequences of SEQ ID NO: 22 or SEQ ID NO: 26, respectively, (xiii) a polypeptide comprising the amino acid sequences of SEQ ID NO: 9 or SEQ ID NO: 15, and a DNA encoding the polypeptide, for example, a DNA comprising the nucleotide sequences of SEQ ID NO: 24 or SEQ ID NO: 30, respectively, (xiv) a polypeptide comprising the amino acid sequences of SEQ ID NO: 20 or SEQ ID NO: 21, and a DNA encoding the polypeptide, for example, a DNA comprising the nucleotide sequences of SEQ ID NO: 31 or SEQ ID NO: 32, respectively, and (xv) a polypeptide derived from any of the polypeptides described in (i) to (xiv) by comprising the substitution of one or more amino acids in the heavy chain constant region, or a fragment thereof, and a DNA encoding the polypeptide or the fragment thereof.

These polypeptides and DNAs can be prepared, as described above, using a gene recombination technique.

<Summary of Present Invention>

The present invention described above will be summarized below.

(1) An antibody which comprises a heavy chain variable region comprising complementarity-determining regions of SEQ ID NOs: 1, 2, and 3 and a light chain variable region comprising complementarity-determining regions of SEQ ID NOs: 4, 5, and 6, and has immunological reactivity with a CAPRIN-1 protein, or a fragment thereof.

(2) The antibody or the fragment thereof according to (1), wherein the heavy chain variable region comprises the amino acid sequence of SEQ ID NO: 8, and the light chain variable region comprises the amino acid sequence of SEQ ID NO: 15.

(3) The antibody or the fragment thereof according to (1), wherein the heavy chain variable region comprises the amino acid sequence of SEQ ID NO: 10, and the light chain variable region comprises the amino acid sequence of SEQ ID NO: 15.

(4) The antibody or the fragment thereof according to (1), wherein the heavy chain variable region comprises the amino acid sequence of SEQ ID NO: 7, and the light chain variable region comprises the amino acid sequence of SEQ ID NO: 15.

(5) The antibody or the fragment thereof according to (1), wherein the heavy chain variable region comprises the amino acid sequence of SEQ ID NO: 8, and the light chain variable region comprises the amino acid sequence of SEQ ID NO: 13.

(6) The antibody or the fragment thereof according to (1), wherein the heavy chain variable region comprises the amino acid sequence of SEQ ID NO: 7, and the light chain variable region comprises the amino acid sequence of SEQ ID NO: 12.

(7) The antibody or the fragment thereof according to (1), wherein the heavy chain variable region comprises the amino acid sequence of SEQ ID NO: 8, and the light chain variable region comprises the amino acid sequence of SEQ ID NO: 12.

(8) The antibody or the fragment thereof according to (1), wherein the heavy chain variable region comprises the amino acid sequence of SEQ ID NO: 7, and the light chain variable region comprises the amino acid sequence of SEQ ID NO: 13.

(9) The antibody or the fragment thereof according to (1), wherein the heavy chain variable region comprises the amino acid sequence of SEQ ID NO: 10, and the light chain variable region comprises the amino acid sequence of SEQ ID NO: 14.

(10) The antibody or the fragment thereof according to (1), wherein the heavy chain variable region comprises the amino acid sequence of SEQ ID NO: 8, and the light chain variable region comprises the amino acid sequence of SEQ ID NO: 11.

(11) The antibody or the fragment thereof according to (1), wherein the heavy chain variable region comprises the amino acid sequence of SEQ ID NO: 7, and the light chain variable region comprises the amino acid sequence of SEQ ID NO: 11.

(12) The antibody or the fragment thereof according to (1), wherein the heavy chain variable region comprises the amino acid sequence of SEQ ID NO: 9, and the light chain variable region comprises the amino acid sequence of SEQ ID NO: 15.

(13) The antibody or the fragment thereof according to (1), wherein the heavy chain variable region comprises the amino acid sequence of SEQ ID NO: 20, and the light chain variable region comprises the amino acid sequence of SEQ ID NO: 21.

(14) The antibody or the fragment thereof according to any of (1) to (13), wherein the antibody is a human antibody, a humanized antibody, a chimeric antibody, a single-chain antibody, or a multispecific antibody.

(15) The antibody or the fragment thereof according to any of (1) to (13), wherein the antibody or the fragment is conjugated with an antitumor agent.

(16) The antibody according to any of (1) to (15), wherein the antibody comprises the substitution of one or more amino acids in the heavy chain constant region thereof.

(17) The antibody according to any of (1) to (16), wherein the antibody is an antibody lacking fucose added to N-acetylglucosamine at the sugar chain reducing end of a N-glycoside-linked sugar chain attached to the heavy chain constant region.

(18) An antibody composition comprising an antibody according to (17) and an antibody according to any of (1) to (16) having fucose added to N-acetylglucosamine at the sugar chain reducing end of a N-glycoside-linked sugar chain attached to the heavy chain constant region.

(19) A cell producing an antibody according to (17) or an antibody composition according to (18).

(20) A pharmaceutical composition for the treatment and/or prevention of a cancer, comprising an antibody or a fragment thereof according to any of (1) to (15), an antibody according to (16) or (17), or an antibody composition according to (18) as an active ingredient.

(21) The pharmaceutical composition according to (20), wherein the cancer is breast cancer, kidney cancer, pancreatic cancer, colorectal cancer, lung cancer, brain tumor, stomach cancer, uterine cancer, ovary cancer, prostate cancer, bladder cancer, esophagus cancer, leukemia, lymphoma, liver cancer, gallbladder cancer, sarcoma, mastocytoma, melanoma, adrenal cortex cancer, Ewing's tumor, Hodgkin's lymphoma, mesothelioma, multiple myeloma, testicle cancer, thyroid cancer, or head and neck cancer.

(22) A combination drug product for the treatment and/or prevention of a cancer, comprising a pharmaceutical composition according to (20) or (21) and a pharmaceutical composition comprising an antitumor agent.

(23) A DNA encoding an antibody or a fragment thereof according to any of (1) to (16).

(24) A method for treating and/or preventing a cancer, comprising administering an antibody or a fragment thereof according to any of (1) to (16), an antibody according to (17), an antibody composition according to (18), a pharmaceutical composition according to (20) or (21), or a combination drug product according to (22) to a subject.

EXAMPLES

Hereinafter, the present invention will be described more specifically with reference to Examples. However, the scope of the present invention is not intended to be limited by these specific examples.

Example 1: Preparation of Anti-CAPRIN-1 Monoclonal Antibody Using Rabbit

300 µg of human CAPRIN-1 protein prepared in Example 3 of WO2010/016526 was mixed with an equal amount of a Freund's complete adjuvant, and this was used as an antigen solution per rabbit. A mixture with a Freund's incomplete adjuvant was used in the second or later immunization. The antigen solution was intraperitoneally administered to each 12-week-old rabbit, and then, administered 8 times every 2 to 3 weeks to complete immunization. Lymphocytes were obtained from the spleen of each rabbit excised 4 days after the final immunization, and mixed with rabbit myeloma cells 240E-W2 at a ratio of 1:2. A PEG solution (heated to 37° C.) prepared by mixing 200 µL of an RPMI medium containing 10% FBS and 800 µL of PEG1500 was added thereto, and the mixture was left standing for 5 minutes fuse cells. After centrifugation and removal of the supernatant, the cells were suspended in 300 mL of an RPMI medium containing 10% FBS supplemented with HAT solution (HAT selective medium) at a concentration of 2% and inoculated at 100 µL/well to 80 96-well plates. Hybridomas generated by the fusion of the spleen cells and the rabbit myeloma cells were obtained by culturing at 37° C. for 7 days under conditions of 5% $CO_2$.

Hybridomas were selected based on the reactivity of antibodies produced by the prepared hybridomas with the CAPRIN-1 protein. A 1 µg/mL CAPRIN-1 protein solution was added at 100 µL/well to the 96-well plates, and the plates were left standing at 4° C. for 18 hours. Each well was washed with PBS-T three times. Then, a 0.5% bovine serum albumin (BSA) solution was added at 400 µL/well, and the plates were left standing at room temperature for 3 hours. The solution was removed, and the wells were washed with 400 µL/well of PBS-T three times. Then, each culture supernatant of the hybridoma obtained above was added at 100 µL/well, and the plates were left standing at room temperature for 2 hours. Each well was washed with PBS-T three times. Then, an HRP-labeled anti-rabbit antibody diluted 5000-fold with PBS was added at 100 µL/well, and the plates were left standing at room temperature for 1 hour. Each well was washed with PBS-T three times. Then, a TMB substrate solution was added at 100 µL/well, and the plates were left standing for 15 to 30 minutes for chromogenic reaction. After the color development, the reaction was terminated by the addition of 1 N sulfuric acid at 100 µL/well, and the absorbance values were measured at 450 nm and 595 nm using an absorption spectrometer. As a result, a plurality of hybridomas producing antibodies that exhibited a high absorbance values were selected.

The selected hybridomas were added at 0.5 cells/well to 96-well plates and cultured. After 1 week, hybridomas that formed single colonies in the wells were observed. The cells in these wells were further cultured, and hybridomas were selected based on the reactivity of antibodies produced by the cloned hybridomas with the CAPRIN-1 protein. As a result of evaluating the reactivity of each antibody with the CAPRIN-1 protein by the same procedure as above, a plurality of hybridoma lines producing rabbit monoclonal antibodies that exhibited reactivity with the CAPRIN-1 protein were obtained.

Next, these rabbit monoclonal antibodies that exhibited reactivity with the CAPRIN-1 protein were screened for ones exhibiting reactivity with the surface of human cancer cells on which CAPRIN-1-was expressed. Specifically, $2\times10^5$ cells each of a human lung cancer cell line QG56 and a human breast cancer cell line BT-474 (obtained from ATCC) were centrifuged in each 1.5 mL microcentrifuge tube, to which 100 µL of the culture supernatant of each of the hybridomas was then added. The tube was left standing on ice for 1 hour. After washing with PBS, an FITC-labeled anti-rabbit IgG (H+L) antibody or Alexa 488-labeled anti-rabbit IgG (H+L) diluted 100-fold with PBS(−) containing 0.5% FBS (0.5% FBS-PBS(−)) was added thereto, and the tube was left standing on ice for 1 hour. After washing with 0.5% FBS-PBS(−), the cells were suspended in 0.2 µg/mL propidium iodide and 0.5% FBS-PBS(−), and the fluorescence intensity was measured using FACSCalibur™ or FACSVerse™ (Becton, Dickinson and Company). On the other hand, the same procedure as above was carried out using a medium for hybridoma culture, and the resultant was used as a sample for a negative control. As a result, one rabbit anti-CAPRIN-1 monoclonal antibody that exhibited stronger fluorescence intensity than that of the negative control, i.e., strongly reacted with the cell surface of the cancer cells QG56 and BT-474 on expressing CAPRIN-1, was selected.

Next, amplification fragments of variable region-encoding genes as to the rabbit anti-CAPRIN-1 monoclonal antibody obtained above were obtained according to the method described in Example 5 of WO2010/016526, and analyzed for their gene sequences and the amino acid sequences encoded thereby. Specifically. mRNA was extracted from the hybridoma producing the rabbit anti-CAPRIN-1 monoclonal antibody, and the genes of the heavy chain variable (VH) region and the light chain variable (VL) region of this antibody were obtained by RT-PCR using primers specific for rabbit variable region sequences. These genes were inserted to cloning vectors, and their respective nucleotide sequences were determined according to a routine method.

The resulting rabbit anti-CAPRIN-1 monoclonal antibody was confirmed to have a heavy chain variable region represented by SEQ ID NO: 20, the heavy chain variable region containing CDR1, CDR2, and CDR3 consisting of the amino acid sequences of SEQ ID NO: 1, SEQ ID NO: 2, and SEQ ID NO: 3, respectively, and to have a light chain variable region represented by SEQ ID NO: 21, the light chain variable region containing CDR1, CDR2, and CDR3 consisting of the amino acid sequences of SEQ ID NO: 4, SEQ ID NO: 5, and SEQ ID NO: 6, respectively.

Next, the reactivity of the obtained rabbit anti-CAPRIN-1 monoclonal antibody with various human cancer cells was confirmed. The obtained antibody was reacted with human cancer cells confirmed to express the gene of CAPRIN-1, i.e., breast cancer cells (BT-474 and MDA-MB-361), colorectal cancer cells (HT-29), lung cancer cells (QG56), stomach cancer cells (NCI-N87), uterine cancer cells (HEC-1-A), prostate cancer cells (22Rv1), pancreatic cancer cells (Panc10.5), liver cancer cells (Hep3B), ovary cancer cells (SKOV3), kidney cancer cells (Caki-2), brain tumor cells (U-87MG), bladder cancer cells (T24 and HT-1376), esophagus cancer cells (OE33), leukemia cells (OCI-AML5), lymphoma cells (Ramos), gallbladder cancer cells (TGBC14TKB), fibrosarcoma cells (HT-1080), melanoma cells (G-361), adrenal cortex cancer cells (A-673), Ewing's tumor cells (RD-ES), Hodgkin's lymphoma cells (RPMI1666), mesothelioma cells (NCI-H2452), multiple myeloma cells (IM-9), testicle cancer cells (NT/D1), thyroid cancer cells (TT), or head and neck cancer cells (FaDu), and the fluorescence intensity was evaluated by flow cytometry. $10^6$ cells of each cancer cell line were collected into each 1.5 mL microcentrifuge tube, and the culture supernatant (100 µL) of the hybridoma producing the rabbit anti-CAPRIN-1 monoclonal antibody obtained above was added to each tube and reacted at 4° C. for 1 hour. After washing with 0.5% FBS-PBS(−), an FITC-labeled goat anti-rabbit IgG (H+L) antibody (manufactured by Jackson ImmunoResearch Laboratories, Inc.) diluted 50-fold with 0.5% FBS-PBS(−) was added thereto, and the tube was left standing at 4° C. for 60 minutes. After washing with 0.5% FBS-PBS(−), the cells were suspended in 0.5% FBS-PBS(−) containing 0.2 µg/mL (final concentration) propidium iodide, and the fluorescence intensity was measured using FACSCalibur® or FACSVerse™ (Becton, Dickinson and Company). On the other hand, the same procedure as above was carried out for a negative control using a medium for hybridoma culture, and the resultant prepared was used as a sample for a negative control. As a result, in all of the cancer cells used in the evaluation, the fluorescence intensity when using the culture supernatant of the hybridoma producing the rabbit anti-CAPRIN-1 monoclonal antibody was stronger than that when using the negative control. From these results, the rabbit anti-CAPRIN-1 monoclonal antibody was confirmed to react with CAPRIN-1 on the cancer cell membrane surface of human cancer cells.

Example 2: Preparation of Human-Rabbit Chimeric Anti-CAPRIN-1 Monoclonal Antibody The gene for expressing the amino acid sequence of the heavy chain variable region represented by SEQ ID NO: 20 of the rabbit anti-CAPRIN-1 monoclonal antibody confirmed in Example 1 and the gene for expressing the light chain variable region represented by SEQ ID NO: 21 thereof were respectively inserted to a vector for expression in mammalian cells having a gene insert of the heavy chain constant region of human IgG and a vector for expression in mammalian cells having a gene insert of the light chain constant region of human IgG1. The prepared two recombinant expression vectors were transferred to mammalian cells according to a routine method, and a culture supernatant containing a human-rabbit chimeric anti-CAPRIN-1 antibody (human-rabbit chimeric antibody) was obtained. The obtained culture supernatant containing the chimerized antibody was purified according to a routine method using Hitrap Protein A Sepharose FF (manufactured by GE Healthcare Japan Corp.). The buffer was replaced with PBS(−), and the resultant was filtered through a 0.22 µm filter (manufactured by Merck Millipore Corp.) to prepare the chimeric antibody.

Example 3: Preparation of Humanized Anti-CAPRIN-1 Monoclonal Antibodies

Next, on the basis of information on the amino acid sequences and the nucleotide sequences of CDR1 to CDR3 in the heavy chain variable region of the rabbit anti-CAPRIN-1 monoclonal antibody confirmed in Example 1 and CDR1 to CDR3 in the light chain variable region thereof, a nucleotide sequence was designed so as to be able to express the amino acid sequence of a heavy chain variable region represented by SEQ ID NO: 7 in which heavy chain variable region CDR1, CDR2, and CDR3 consisted of the amino acid sequences of SEQ ID NO: 1, SEQ ID NO: 2, and SEQ ID NO: 3, respectively. This was inserted to a vector for expression in mammalian cells having a gene insert of the heavy chain constant region of human IgG1. Similarly, a nucleotide sequence was designed so as to be able to express the amino acid sequence of a light chain variable region represented by SEQ ID NO: 11 in which light chain variable region CDR1, CDR2, and CDR3 consisted of the amino acid sequences of SEQ ID NO: 4, SEQ ID NO: 5, and SEQ ID NO: 6, respectively. This was inserted to a vector for expression in mammalian cells having a gene insert of the light chain constant region of human IgG1. These two recombinant expression vectors were transferred to mammalian cells according to a routine method, and a culture supernatant containing humanized antibody #0 consisting of the heavy chain full-length amino acid sequence represented by SEQ ID NO: 7 and the light chain full-length amino acid sequence represented by SEQ ID NO: 11 was obtained.

Similarly, a culture supernatant containing humanized antibody #1 consisting of the amino acid sequence of a heavy chain variable region represented by SEQ ID NO: 8 in which heavy chain variable region CDR1, CDR2, and CDR3 consisted of the amino acid sequences of SEQ ID NO: 1, SEQ ID NO: 2, and SEQ ID NO: 3, respectively, and the amino acid sequence of the light chain variable region represented by SEQ ID NO: 11, was obtained.

Similarly, culture supernatants containing the following humanized antibodies #2 to 10 were further obtained:

humanized antibody #2 consisting of the amino acid sequence of the heavy chain variable region represented by SEQ ID NO: 8 and the light chain full-length amino acid sequence represented by SEQ ID NO: 12 in which light chain variable region CDR1, CDR2, and CDR3 consisted of the amino acid sequences of SEQ ID NO: 4, SEQ ID NO: 5, and SEQ ID NO: 6, respectively;

humanized antibody #3 consisting of the amino acid sequence of the heavy chain variable region represented by SEQ ID NO: 8 and the light chain full-length amino acid sequence represented by SEQ ID NO: 13 in which light chain variable region CDR1, CDR2, and CDR3 consisted of the amino acid sequences of SEQ ID NO: 4, SEQ ID NO: 5, and SEQ ID NO: 6, respectively;

humanized antibody #4 consisting of the amino acid sequence of the heavy chain variable region represented by SEQ ID NO: 7 and the light chain full-length amino acid sequence represented by SEQ ID NO: 12;

humanized antibody #5 consisting of the amino acid sequence of the heavy chain variable region represented by SEQ ID NO: 7 and the light chain full-length amino acid sequence represented by SEQ ID NO: 13;

humanized antibody #6 consisting of the amino acid sequence of the heavy chain variable region represented by SEQ ID NO: 7 and the light chain full-length amino acid sequence represented by SEQ ID NO: 15 in which light chain variable region CDR1, CDR2, and CDR3 consisted of the amino acid sequences of SEQ ID NO: 4, SEQ ID NO: 5, and SEQ ID NO: 6, respectively;

humanized antibody #7 consisting of the amino acid sequence of the heavy chain variable region represented by SEQ ID NO: 8 and the light chain full-length amino acid sequence represented by SEQ ID NO: 15;

humanized antibody #8 consisting of the amino acid sequence of a heavy chain variable region represented by SEQ ID NO: 9 in which heavy chain variable region CDR1, CDR2, and CDR3 consisted of the amino acid sequences of SEQ ID NO: 1, SEQ ID NO: 2, and SEQ ID NO: 3, respectively, and the light chain full-length amino acid sequence represented by SEQ ID NO: 15.

humanized antibody #9 consisting of the amino acid sequence of a heavy chain variable region represented by SEQ ID NO: 10 in which heavy chain variable region CDR1, CDR2, and CDR3 consisted of the amino acid sequences of SEQ ID NO: 1, SEQ ID NO: 2, and SEQ ID NO: 3, respectively, and the light chain full-length amino acid sequence represented by SEQ ID NO: 14 in which light chain variable region CDR1, CDR2, and CDR3 consisted of the amino acid sequences of SEQ ID NO: 4, SEQ ID NO: 5, and SEQ ID NO: 6, respectively; and humanized antibody #10 consisting of the amino acid sequence of the heavy chain variable region represented by SEQ ID NO: 10 and the light chain full-length amino acid sequence represented by SEQ ID NO: 15;

The obtained culture supernatants containing the humanized antibodies #0 to #10 were each purified according to a routine method using Hitrap Protein A Sepharose FF (manufactured by GE Healthcare Japan Corp.). The buffer was replaced with PBS(−), and the resultant was filtered through a 0.22 µm filter (manufactured by Merck Millipore Corp.) to prepare the humanized antibodies.

Example 4: Antigen Specificity of Human-Rabbit Chimeric Antibody and Humanized Antibodies #0 to #10 and Reactivity Thereof with Cancer Cells Next, the specific reactivity of the human-rabbit chimeric antibody prepared in Example 2 and the humanized antibodies #0 to #10 prepared in Example 3 with the CAPRIN-1 protein was confirmed by ELISA according to a routine method. Specifically, at first, a PBS solution containing 5 µg/mL CAPRIN-1 protein was added at 100 µL/well to 96-well plates, and the plates were left standing at 4° C. for 18 hours. Each well was washed with PBS-T. Then, a blocking solution consisting of a PBS solution containing 5% skimmed milk was added at 400 µL/well, and the plates were left standing at room temperature for 3 hours. The solution was removed, and each well was washed with PBS-T. Then, a solution containing each of the human-rabbit chimeric antibody and the humanized antibodies #0 to #10 adjusted to 1 µg/mL with PBS containing 0.2% skimmed milk was added at 50 µL/well to each well, and the plates were left standing at room temperature for 1 hour. A well to which of a human IgG antibody confirmed not to react with the CAPRIN-1 protein was added at the same antibody concentration as above, and a well to which no antibody was added were prepared as negative controls together therewith. Each well was washed with PBS-T three times. Then, an HRP-labeled anti-human IgG antibody diluted 3000-fold with PBS containing 0.2% skimmed milk was added at 50 µL/well, and the plates were left standing at room temperature for 1 hour. Each well was washed with PBS-T three times. Then, a TMB substrate solution (manufactured by Thermo Fischer Scientific, Inc.) was added at 100 µL/well, and the plates were left standing for 1 to 30 minutes for chromogenic reaction. After the color development, the reaction was terminated by the addition of 1 N sulfuric acid at 100 µL/well, and the absorbance values were measured at 450 nm and 630 nm using an absorption spectrometer. Further, wells on which the CAPRIN-1 protein was not immobilized (non-immobilized wells) were prepared together therewith, and each antibody was added and assayed similarly. As a result, the absorbance value of the well used as a negative control to which a human IgG antibody confirmed not to react with the CAPRIN-1 protein was added, was as low as that of the well to which no antibody was added, whereas the wells respectively to which the respective human-rabbit chimeric antibody and the humanized antibodies #0 to #10 exhibited equivalently high absorbance values. The human-rabbit chimeric antibody and the humanized antibodies #0 to #10 in the wells on which the CAPRIN-1 protein was not immobilized merely exhibited an absorbance value equivalent to that of the negative control. From these results, the human-rabbit chimeric antibody and the humanized antibodies #0 to #10 were confirmed to specifically react with the CAPRIN-1 protein.

Next, the reactivity of the human-rabbit chimeric antibody and the humanized antibodies #0 to #10 specifically reacting with the CAPRIN-1 protein, with various human cancer cells and mouse cancer cells was confirmed. The purified human-rabbit chimeric antibody and humanized antibodies #0 to #10 were each reacted with human cancer cells confirmed to express the gene of CAPRIN-1, i.e., breast cancer cells (BT-474 and MDA-MB-361), colorectal cancer cells (HT-29), lung cancer cells (QG56), stomach cancer cells (NCI-N87), uterine cancer cells (HEC-1-A), prostate cancer cells (22Rv1), pancreatic cancer cells (Panc10.5), liver cancer cells (Hep3B), ovary cancer cells (SKOV3), kidney cancer cells (Caki-2), brain tumor cells (U-87MG), bladder cancer cells (T24 and HT-1376), esophagus cancer cells (OE33), leukemia cells (OCI-AML5), lymphoma cells (Ramos), gallbladder cancer cells (TGBC14TKB), fibrosarcoma cells (HT-1080), melanoma cells (G-361), adrenal cortex cancer cells (A-673), Ewing's tumor cells (RD-ES), Hodgkin's lymphoma cells (RPMI1666), mesothelioma cells (NCI-H2452), multiple myeloma cells (IM-9), testicle cancer cells (NT/D1), thyroid cancer cells (TT), or head and neck cancer cells (FaDu), and the fluorescence intensity was evaluated by flow cytometry. Specifically, $5 \times 10^5$ cells of each cancer cell line were collected into each 1.5 mL microcentrifuge tube, and each of the human-rabbit chimeric antibody and the humanized antibodies #0 to #10 was added at 50 µg/mL (final concentration) to each tube and reacted at 4° C. for 1 hour. After washing with 0.5% FBS-PBS(−) twice, an Alexa 488-labeled goat anti-human IgG (H+L) antibody (manufactured by Life Technologies Corp.) diluted 100-fold with 0.5% FBS-PBS(−) was added thereto, and the tube was left standing at 4° C. for 60 minutes. After washing with 0.5% FBS-PBS(−), the cells were suspended in 0.5% FBS-PBS(−) containing 0.2 µg/mL (final concentration) propidium iodide, and the fluorescence intensity was measured using FACSCalibur™ or FACSVerse™ (Becton, Dickinson and Company). On the other hand, the same procedure as above was carried out using a medium for hybridoma culture, and the resultant prepared was used for a negative control. As a result, in all of the cancer cells used in the evaluation, the fluorescence intensity from the human-rabbit chimeric antibody and the humanized antibodies #0 to #10 was stronger than that in the case of using the negative control. From these results, the human-rabbit chimeric antibody and the humanized antibodies #0 to #10 were confirmed to react with the CAPRIN-1 protein expressed on the membrane surface of human cancer cells.

Example 5: Antitumor Activity of Human-Rabbit Chimeric Antibody and Humanized Antibodies #0 to #10 Against Various Human Cancer Cells Next, the human-rabbit chimeric antibody prepared in Example 2 and the humanized antibodies #0 to #10 prepared in Example 3 were evaluated for their antitumor effects on various human cancer cells on the basis of ADCC activity.

The following anti-CAPRIN-1 antibodies were used as comparative antibodies for the human-rabbit chimeric antibody and the humanized antibodies #0 to #10:

antibodies described in WO2010/016526, i.e., comparative antibody 1 having a heavy chain variable region of SEQ ID NO: 26 and a light chain variable region of SEQ ID NO: 27 in this literature, comparative antibody 2 having a heavy chain variable region of SEQ ID NO: 28 and a light chain variable region of SEQ ID NO: 29 therein, comparative antibody 3 having a heavy chain variable region of SEQ ID NO: 30 and a light chain variable region of SEQ ID NO: 31 therein, comparative antibody 4 having a heavy chain variable region of SEQ ID NO: 32 and a light chain variable region of SEQ ID NO: 33 therein, comparative antibody 5 having a heavy chain variable region of SEQ ID NO: 34 and a light chain variable region of SEQ ID NO: 35 therein, comparative antibody 6 having a heavy chain variable region of SEQ ID NO: 36 and a light chain variable region of SEQ ID NO: 37 therein, comparative antibody 7 having a heavy chain variable region of SEQ ID NO: 38 and a light chain variable region of SEQ ID NO: 39 therein, comparative antibody 8 having a heavy chain variable region of SEQ ID NO: 40 and a light chain variable region of SEQ ID NO: 41 therein, comparative antibody 9 having a heavy chain variable region of SEQ ID NO: 42 and a light chain variable region of SEQ ID NO: 43 therein, comparative antibody 10 having a heavy chain variable region of SEQ ID NO: 44 and a light chain variable region of SEQ ID NO: 45 therein, and comparative antibody 11 having a heavy chain variable region of SEQ ID NO: 46 and a light chain variable region of SEQ ID NO: 47 therein;

antibodies described in WO2011/096517, i.e., comparative antibody 12 having a heavy chain variable region of SEQ ID NO: 43 and a light chain variable region of SEQ ID NO: 47 in this literature, and comparative antibody 13 having a heavy chain variable region of SEQ ID NO: 43 and a light chain variable region of SEQ ID NO: 53 therein:

antibodies described in WO2011/096528, i.e., comparative antibody 14 having a heavy chain variable region of SEQ ID NO: 43 and a light chain variable region of SEQ ID NO: 47 in this literature, comparative antibody 15 having a heavy chain variable region of SEQ ID NO: 51 and a light chain variable region of SEQ ID NO: 55 therein, comparative antibody 16 having a heavy chain variable region of SEQ ID NO: 59 and a light chain variable region of SEQ ID NO: 63 therein, comparative antibody 17 having a heavy chain variable region of SEQ ID NO: 76 and a light chain variable region of SEQ ID NO: 80 therein, comparative antibody 18 having a heavy chain variable region of SEQ ID NO: 84 and a light chain variable region of SEQ ID NO: 88 therein, and comparative antibody 19 having a heavy chain variable region of SEQ ID NO: 92 and a light chain variable region of SEQ ID NO: 96 therein;

an antibody described in WO2011/096519, i.e., comparative antibody 20 having a heavy chain variable region of SEQ ID NO: 42 and a light chain variable region of SEQ ID NO: 46 in this literature;

antibodies described in WO2011/096533, i.e., comparative antibody 21 having a heavy chain variable region of SEQ ID NO: 43 and a light chain variable region of SEQ ID NO: 51 in this literature, comparative antibody 22 having a heavy chain variable region of SEQ ID NO: 47 and a light chain variable region of SEQ ID NO: 51 therein, and comparative antibody 23 having a heavy chain variable region of SEQ ID NO: 63 and a light chain variable region of SEQ ID NO: 67 therein;

antibodies described in WO2011/096534, i.e., comparative antibody 24 having a heavy chain variable region of SEQ ID NO: 43 and a light chain variable region of SEQ ID NO: 47 in this literature, comparative antibody 25 having a heavy chain variable region of SEQ ID NO: 43 and a light chain variable region of SEQ ID NO: 51 therein, and comparative antibody 26 having a heavy chain variable region of SEQ ID NO: 63 and a light chain variable region of SEQ ID NO: 67 therein;

antibodies described in WO2013/018894, i.e., comparative antibody 27 having a heavy chain variable region of SEQ ID NO: 9 and a light chain variable region of SEQ ID NO: 13 in this literature, comparative antibody 28 having a heavy chain variable region of SEQ ID NO: 19 and a light chain variable region of SEQ ID NO: 23 therein, comparative antibody 29 having a heavy chain variable region of SEQ ID NO: 9 and a light chain variable region of SEQ ID NO: 53 therein, comparative antibody 30 having a heavy chain variable region of SEQ ID NO: 58 and a light chain variable region of SEQ ID NO: 62 therein, comparative antibody 31 having a heavy chain variable region of SEQ ID NO: 63 and a light chain variable region of SEQ ID NO: 65 therein, comparative antibody 32 having a heavy chain variable region of SEQ ID NO: 69 and a light chain variable region of SEQ ID NO: 73 therein, and comparative antibody 33 having a heavy chain variable region of SEQ ID NO: 77 and a light chain variable region of SEQ ID NO: 81 therein:

an antibody described in WO2013/018892, i.e., comparative antibody 34 having a heavy chain variable region of SEQ ID NO: 8 and a light chain variable region of SEQ ID NO: 12 in this literature;

an antibody described in WO2013/018891, i.e., comparative antibody 35 having a heavy chain variable region of SEQ ID NO: 8 and a light chain variable region of SEQ ID NO: 12 in this literature;

an antibody described in WO2013/018889, i.e., comparative antibody 36 having a heavy chain variable region of SEQ ID NO: 8 and a light chain variable region of SEQ ID NO: 12 in this literature;

an antibody described in WO2010/018883, i.e., comparative antibody 37 having a heavy chain variable region of SEQ ID NO: 8 and a light chain variable region of SEQ ID NO: 12 in this literature;

an antibody described in WO2013/125636, i.e., comparative antibody 38 having a heavy chain variable region of SEQ ID NO: 6 and a light chain variable region of SEQ ID NO: 7 in this literature;

antibodies described in WO2013/125654, i.e., comparative antibody 39 having a heavy chain variable region of SEQ ID NO: 52 and a light chain variable region of SEQ ID NO: 54 in this literature, comparative antibody 40 having a heavy chain variable region of SEQ ID NO: 21 and a light chain variable region of SEQ ID NO: 23 therein, comparative antibody 41 having a heavy chain variable region of SEQ ID NO: 25 and a light chain variable region of SEQ ID NO: 23 therein, comparative antibody 42 having a heavy chain variable region of SEQ ID NO: 16 and a light chain variable region of SEQ ID NO: 18 therein, comparative antibody 43 having a heavy chain variable region of SEQ ID NO: 29 and a light chain variable region of SEQ ID NO: 33 therein, comparative antibody 44 having a heavy chain variable region of SEQ ID NO: 39 and a light chain variable region of SEQ ID NO: 43 therein, and comparative antibody 45 having a heavy chain variable region of SEQ ID NO: 49 and a light chain variable region of SEQ ID NO: 43 therein;

an antibody described in WO2013/125630, i.e., comparative antibody 46 having a heavy chain variable region of SEQ ID NO: 11 and a light chain variable region of SEQ ID NO: 15 in this literature; and antibodies described in WO2013/125640, i.e., comparative antibody 47 having a heavy chain variable region of SEQ ID NO: 11 and a light chain variable region of SEQ ID NO: 15 in this literature, and comparative antibody 48 having a heavy chain variable region of SEQ ID NO: 21 and a light chain variable region of SEQ ID NO: 25 therein.

The aforementioned compared antibodies (comparative antibodies 1 to 48) were each prepared as follows: the gene for expressing the amino acid sequence of the heavy chain variable region and the gene for expressing the light chain variable region were respectively inserted to a vector pcDNA4/myc-His for expression in mammalian cells (manufactured by Life Technologies Corp.) having a gene insert of the heavy chain constant region of human IgG1 and a vector pcDNA3.1/myc-His for expression in mammalian cells (manufactured by Life Technologies Corp.) having a gene insert of the light chain constant region of human IgG1; the prepared two recombinant expression vectors were transferred to mammalian cells according to a routine method; the obtained human-chimerized or humanized antibody was purified using Hitrap Protein A Sepharose FF (manufactured by GE Healthcare Japan Corp.); the buffer was replaced with PBS(−); and the resultant was filtered through a 0.22 μm filter (manufactured by Merck Millipore Corp.).

A well to which an isotype control antibody was added, a well to which no antibody was added, and a well to which an antibody reacting with the CAPRIN-1 protein but exhibiting no reactivity with the surface of human cancer cells, on which CAPRIN-1 was expressed, was added were prepared as negative controls. Each antibody was added at 5 μg/mL (final concentration) to V-bottomed 96-well plates.

Human NK cells separated from human peripheral blood mononuclear cells by using a routine method were used as effector cells. The human peripheral blood mononuclear cells were separated using a specific gravity separation solution Histopaque for peripheral blood mononuclear cell separation (Sigma-Aldrich Corp.), and reacted with antibodies (anti-human CD3 antibody, anti-human CD20 antibody, anti-human CD19 antibody, anti-human CD11c antibody, anti-HLA-DR antibody (BD Pharmingen)) labeled with an FITC fluorescent dye. A cell population containing NK cells that were not stained with these antibodies was separated using a cell sorter (FACS Vantage SE (Becton, Dickinson and Company)). Alternatively, a cell population separated using a human NK cell separation kit (manufactured by Miltenyi Biotec K.K.) was used. The V-bottomed 96-well plates to which each of the antibodies was added and the human NK cells were added at 0.4 to $2.0 \times 10^5$ cells/well were prepared.

Breast cancer cells (BT-474 and MDA-MB-361), colorectal cancer cells (HT-29), lung cancer cells (QG56), stomach cancer cells (NCI-N87), uterine cancer cells (HEC-1-A), prostate cancer cells (22Rv1), pancreatic cancer cells (Panc10.5), liver cancer cells (Hep3B), ovary cancer cells (SKOV3), kidney cancer cells (Caki-2), brain tumor cells (U-87MG), bladder cancer cells (T24 and HT-1376), esophagus cancer cells (OE33), leukemia cells (OCI-AML5), lymphoma cells (Ramos), gallbladder cancer cells (TGBC14TKB), fibrosarcoma cells (HT-1080), melanoma cells (G-361), adrenal cortex cancer (A-673), Ewing's tumor (RD-ES), Hodgkin's lymphoma (RPMI1666), mesothelioma (NCI-H2452), multiple myeloma (IM-9), testicle cancer (NT/D1), thyroid cancer (TT), and head and neck cancer (FaDu) were used as target cells. $10^6$ cells of each human cancer cell line mentioned above were collected into each 50 mL centrifugal tube. 100 μCi of chromium 51 (manufactured by PerkinElmer, Inc.) was added thereto, and the tube was incubated at 37° C. for 1 hour. Then, the cells were washed with an RPMI1640 medium containing 10% FBS three times, added at $2 \times 10^3$ cells/well to the 96-well V-bottomed plates to which the effector cells and each antibody were added as described above, and reacted at 37° C. for 4 hours under conditions of 5% $CO_2$. After the reaction, 50 μL of a culture supernatant containing chromium 51 released into the culture supernatant from damaged cancer cells was recovered from each well, added to LumaPlate-96 (manufactured by PerkinElmer, Inc.) with the bottom of each well coated with a solid scintillator, and dried. The amount of chromium 51 released into the culture supernatant from damaged cancer cells was measured to calculate the antitumor effects of the anti-CAPRIN-1 antibodies on the cancer cells.

As a result, for the breast cancer cells (BT-474), the humanized antibody #7, the humanized antibody #10, and the humanized antibody #6 exhibited 54% or higher antitumor effect, the humanized antibody #3, the humanized antibody #4, the humanized antibody #2, and the humanized antibody #5 exhibited 50% or higher activity, and the humanized antibody #9, the humanized antibody #1, the humanized antibody #0, the human-rabbit chimeric antibody, and the humanized antibody #8 exhibited 46% or higher activity. By contrast, all of the comparative antibodies 1 to 48 exhibited 25% or lower activity, and all of the negative control groups exhibited 10% or lower activity.

For the breast cancer cells (MDA-MB-361), the humanized antibody #7, the humanized antibody #10, and the humanized antibody #6 exhibited 52% or higher antitumor effect, the humanized antibody #3, the humanized antibody #4, the humanized antibody #2, and the humanized antibody #5 exhibited 45% or higher activity, and the humanized antibody #9, the humanized antibody #1, the humanized antibody #0, the human-rabbit chimeric antibody, and the humanized antibody #8 exhibited 40% or higher activity. By contrast, all of the comparative antibodies 1 to 48 exhibited 25% or lower activity, and all of the negative control groups exhibited 6% or lower activity.

For the colorectal cancer cells (HT-29), the humanized antibody #7, the humanized antibody #10, and the humanized antibody #6 exhibited 43% or higher antitumor effect, the humanized antibody #3, the humanized antibody #4, the humanized antibody #2, and the humanized antibody #5 exhibited 40% or higher activity, and the humanized antibody #9, the humanized antibody #1, the humanized antibody #0, the human-rabbit chimeric antibody, and the humanized antibody #8 exhibited 35% or higher activity. By contrast, all of the comparative antibodies 1 to 48 exhibited 20% or lower activity, and all of the negative control groups exhibited 3% or lower activity.

For the lung cancer cells (QG56), the humanized antibody #7, the humanized antibody #10, and the humanized antibody #6 exhibited 46% or higher antitumor effect, the humanized antibody #3, the humanized antibody #4, the humanized antibody #2, and the humanized antibody #5 exhibited 42% or higher activity, and the humanized antibody #9, the humanized antibody #1, the humanized antibody #0, the human-rabbit chimeric antibody, and the humanized antibody #8 exhibited 38% or higher activity. By contrast, all of the comparative antibodies 1 to 48 exhibited 22% or lower activity, and all of the negative control groups exhibited 10% or lower activity.

For the stomach cancer cells (NCI-N87), the humanized antibody #7, the humanized antibody #10, and the humanized antibody #6 exhibited 45% or higher antitumor effect, the humanized antibody #3, the humanized antibody #4, the humanized antibody #2, and the humanized antibody #5 exhibited 38% or higher activity, and the antibody #9, the humanized antibody #1, the humanized antibody #0, the human-rabbit chimeric antibody, and the humanized antibody #8 exhibited 34% or higher activity. By contrast, all of the comparative antibodies 1 to 48 exhibited 15% or lower activity, and all of the negative control groups exhibited 8% or lower activity.

For the uterine cancer cells (HEC-1-A), the humanized antibody #7, the humanized antibody #10, and the humanized antibody #6 exhibited 52% or higher antitumor effect, the humanized antibody #3, the humanized antibody #4, the humanized antibody #2, and the humanized antibody #5 exhibited 45% or higher activity, and the humanized antibody #9, the humanized antibody #1, the humanized antibody #0, the human-rabbit chimeric antibody, and the humanized antibody #8 exhibited 40% or higher activity. By contrast, all of the comparative antibodies 1 to 48 exhibited 20% or lower activity, and all of the negative control groups exhibited 5% or lower activity.

For the prostate cancer cells (22Rv1), the humanized antibody #7, the humanized antibody #10, and the humanized antibody #6 exhibited 49% or higher antitumor effect, the humanized antibody #3, the antibody #4, the humanized antibody #2, and the humanized antibody #5 exhibited 45% or higher activity, and the humanized antibody #9, the humanized antibody #1, the humanized antibody #0, the human-rabbit chimeric antibody, and the humanized antibody #8 exhibited 38% or higher activity. By contrast, all of the comparative antibodies 1 to 48 exhibited 20% or lower activity, and all of the negative control groups exhibited 12% or lower activity.

For the pancreatic cancer cells (Panc10.5), the humanized antibody #7, the humanized antibody #10, and the humanized antibody #6 exhibited 35% or higher antitumor effect, the humanized antibody #3, the humanized antibody #4, the humanized antibody #2, and the humanized antibody #5 exhibited 30% or higher activity, and the humanized antibody #9, the humanized antibody #1, the humanized antibody #0, the human-rabbit chimeric antibody, and the humanized antibody #8 exhibited 24% or higher activity. By contrast, all of the comparative antibodies 1 to 48 exhibited 10% or lower activity, and all of the negative control groups exhibited 2% or lower activity.

For the liver cancer cells (Hep3B), the humanized antibody #7, the humanized antibody #10, and the humanized antibody #6 exhibited 28% or higher antitumor effect, the humanized antibody #3, the humanized antibody #4, the humanized antibody #2, and the humanized antibody #5 exhibited 25% or higher activity, and the humanized antibody #9, the humanized antibody #1, the humanized antibody #0, the human-rabbit chimeric antibody, and the humanized antibody #8 exhibited 21% or higher activity. By contrast, all of the comparative antibodies 1 to 48 exhibited 12% or lower activity, and all of the negative control groups exhibited 5% or lower activity.

For the ovary cancer cells (SKOV3), the humanized antibody #7, the humanized antibody #10, and the humanized antibody #6 exhibited 35% or higher antitumor effect, the humanized antibody #3, the humanized antibody #4, the humanized antibody #2, and the humanized antibody #5 exhibited 31% or higher activity, and the humanized antibody #9, the humanized antibody #1, the humanized antibody #0, the human-rabbit chimeric antibody, and the humanized antibody #8 exhibited 27% or higher activity. By contrast, all of the comparative antibodies 1 to 48 exhibited 15% or lower activity, and all of the negative control groups exhibited 5% or lower activity.

For the kidney cancer cells (Caki-2), the humanized antibody #7, the humanized antibody #10, and the humanized antibody #6 exhibited 37% or higher antitumor effect, the humanized antibody #3, the humanized antibody #4, the humanized antibody #2, and the humanized antibody #5 exhibited 33% or higher activity, and the humanized antibody #9, the humanized antibody #1, the humanized antibody #0, the human-rabbit chimeric antibody, and the humanized antibody #8 exhibited 26% or higher activity. By contrast, all of the comparative antibodies 1 to 48 exhibited 15% or lower activity, and all of the negative control groups exhibited 5% or lower activity.

For the brain tumor cells (U-87MG), the humanized antibody #7, the humanized antibody #10, and the humanized antibody #6 exhibited 36% or higher antitumor effect, the humanized antibody #3, the humanized antibody #4, the humanized antibody #2, and the humanized antibody #5 exhibited 29% or higher activity, and the humanized antibody #9, the humanized antibody #1, the humanized antibody #0, the human-rabbit chimeric antibody, and the humanized antibody #8 exhibited 24% or higher activity. By contrast, all of the comparative antibodies 1 to 48 exhibited 10% or lower activity, and all of the negative control groups exhibited 6% or lower activity.

For the bladder cancer cells (T24), the humanized antibody #7, the humanized antibody #10, and the humanized antibody #6 exhibited 36% or higher antitumor effect, the humanized antibody #3, the humanized antibody #4, the humanized antibody #2, and the humanized antibody #5 exhibited 33% or higher activity, and the humanized antibody #9, the humanized antibody #1, the humanized antibody #0, the human-rabbit chimeric antibody, and the humanized antibody #8 exhibited 30% or higher activity. By contrast, all of the comparative antibodies 1 to 48 exhibited 15% or lower activity, and all of the negative control groups exhibited 6% or lower activity.

For the bladder cancer cells (HT-1376), the humanized antibody #7, the humanized antibody #10, and the humanized antibody #6 exhibited 45% or higher antitumor effect, the humanized antibody #3, the humanized antibody #4, the humanized antibody #2, and the humanized antibody #5 exhibited 40% or higher activity, and the humanized antibody #9, the humanized antibody #1, the humanized antibody #0, the human-rabbit chimeric antibody, and the humanized antibody #8 exhibited 28% or higher activity. By contrast, all of the comparative antibodies 1 to 48 exhibited 20% or lower activity, and all of the negative control groups exhibited 7% or lower activity.

For the esophagus cancer cells (OE33), the humanized antibody #7, the humanized antibody #10, and the humanized antibody #6 exhibited 35% or higher antitumor effect, the humanized antibody #3, the humanized antibody #4, the humanized antibody #2, and the humanized antibody #5 exhibited 33% or higher activity, and the humanized antibody #9, the humanized antibody #1, the humanized antibody #0, the human-rabbit chimeric antibody, and the humanized antibody #8 exhibited 30% or higher activity. By contrast, all of the comparative antibodies 1 to 48 exhibited 15% or lower activity, and all of the negative control groups exhibited 6% or lower activity.

For the leukemia cells (OCI-AML5), the humanized antibody #7, the humanized antibody #10, and the humanized antibody #6 exhibited 20% or higher antitumor effect, the humanized antibody #3, the humanized antibody #4, the humanized antibody #2, and the humanized antibody #5 exhibited 18% or higher activity, and the humanized antibody #9, the humanized antibody #1, the humanized antibody #0, the human-rabbit chimeric antibody, and the humanized antibody #8 exhibited 15% or higher activity. By contrast, all of the comparative antibodies 1 to 48 exhibited 10% or lower activity, and all of the negative control groups exhibited 6% or lower activity.

For the lymphoma cells (Ramos), the humanized antibody #7, the humanized antibody #10, and the humanized antibody #6 exhibited 20% or higher antitumor effect, the humanized antibody #3, the humanized antibody #4, the humanized antibody #2, and the humanized antibody #5 exhibited 18% or higher activity, and the antibody #9, the antibody #1, the humanized antibody #0, the human-rabbit chimeric antibody, and the humanized antibody #8 exhibited 15% or higher activity. By contrast, all of the comparative antibodies 1 to 48 exhibited 10% or lower activity, and all of the negative control groups exhibited 6% or lower activity.

For the gallbladder cancer cells (TGBC14TKB), the humanized antibody #7, the humanized antibody #10, and the humanized antibody #6 exhibited 35% or higher antitumor effect, the humanized antibody #3, the humanized antibody #4, the humanized antibody #2, and the humanized antibody #5 exhibited 30% or higher activity, and the humanized antibody #9, the humanized antibody #1, the humanized antibody #0, the human-rabbit chimeric antibody, and the humanized antibody #8 exhibited 25% or higher activity. By contrast, all of the comparative antibodies 1 to 48 exhibited 15% or lower activity, and all of the negative control groups exhibited 6% or lower activity.

For the fibrosarcoma cells (HT-1080), the humanized antibody #7, the humanized antibody #10, and the humanized antibody #6 exhibited 30% or higher antitumor effect, the humanized antibody #3, the antibody #4, the humanized antibody #2, and the humanized antibody #5 exhibited 25% or higher activity, and the humanized antibody #9, the humanized antibody #1, the humanized antibody #0, the human-rabbit chimeric antibody, and the humanized antibody #8 exhibited 20% or higher activity. By contrast, all of the comparative antibodies 1 to 48 exhibited 10% or lower activity, and all of the negative control groups exhibited 6% or lower activity.

For the melanoma (G-361), the humanized antibody #7, the humanized antibody #10, and the humanized antibody #6 exhibited 25% or higher antitumor effect, the humanized antibody #3, the humanized antibody #4, the humanized antibody #2, and the humanized antibody #5 exhibited 21% or higher activity, and the humanized antibody #9, the humanized antibody #1, the humanized antibody #0, the human-rabbit chimeric antibody, and the humanized antibody #8 exhibited 15% or higher activity. By contrast, all of the comparative antibodies 1 to 48 exhibited 8% or lower activity, and all of the negative control groups exhibited 6% or lower activity.

For the adrenal cortex cancer cells (A-673), the humanized antibody #7, the humanized antibody #10, and the humanized antibody #6 exhibited 50% or higher antitumor effect, the humanized antibody #3, the humanized antibody #4, the humanized antibody #2, and the humanized antibody #5 exhibited 46% or higher activity, and the humanized antibody #9, the humanized antibody #1, the humanized antibody #0, the human-rabbit chimeric antibody, and the humanized antibody #8 exhibited 40% or higher activity. By contrast, all of the comparative antibodies 1 to 48 exhibited 20% or lower activity, and all of the negative control groups exhibited 8% or lower activity.

For the Ewing's tumor cells (RD-ES), the humanized antibody #7, the humanized antibody #10, and the humanized antibody #6 exhibited 48% or higher antitumor effect, the humanized antibody #3, the humanized antibody #4, the humanized antibody #2, and the humanized antibody #5 exhibited 40% or higher activity, and the humanized antibody #9, the humanized antibody #1, the humanized antibody #0, the human-rabbit chimeric antibody, and the humanized antibody #8 exhibited 31% or higher activity. By contrast, all of the comparative antibodies 1 to 48 exhibited 15% or lower activity, and all of the negative control groups exhibited 6% or lower activity.

For the Hodgkin's lymphoma cells (RPMI1666), the humanized antibody #7, the humanized antibody #10, and the humanized antibody #6 exhibited 40% or higher antitumor effect, the humanized antibody #3, the humanized antibody #4, the humanized antibody #2, and the humanized antibody #5 exhibited 36% or higher activity, and the humanized antibody #9, the humanized antibody #1, the humanized antibody #0, the human-rabbit chimeric antibody, and the humanized antibody #8 exhibited 30% or higher activity. By contrast, all of the comparative antibodies 1 to 48 exhibited 20% or lower activity, and all of the negative control groups exhibited 5% or lower activity.

For the mesothelioma cells (NCI-H2452), the humanized antibody #7, the humanized antibody #10, and the humanized antibody #6 exhibited 35% or higher antitumor effect, the humanized antibody #3, the humanized antibody #4, the humanized antibody #2, and the humanized antibody #5 exhibited 39% or higher activity, and the humanized antibody #9, the humanized antibody #1, the humanized antibody #0, the human-rabbit chimeric antibody, and the humanized antibody #8 exhibited 31% or higher activity. By contrast, all of the comparative antibodies 1 to 48 exhibited 10% or lower activity, and all of the negative control groups exhibited 5% or lower activity.

For the multiple myeloma cells (IM-9), the humanized antibody #7, the humanized antibody #10, and the humanized antibody #6 exhibited 35% or higher antitumor effect, the humanized antibody #3, the humanized antibody #4, the antibody #2, and the humanized antibody #5 exhibited 30% or higher activity, and the humanized antibody #9, the antibody #1, the humanized antibody #0, the human-rabbit chimeric antibody, and the humanized antibody #8 exhibited 27% or higher activity. By contrast, all of the comparative antibodies 1 to 48 exhibited 10% or lower activity, and all of the negative control groups exhibited 6% or lower activity.

For the testicle cancer cells (NT/D1), the humanized antibody #7, the humanized antibody #10, and the humanized antibody #6 exhibited 37% or higher antitumor effect, the humanized antibody #3, the humanized antibody #4, the humanized antibody #2, and the humanized antibody #5 exhibited 30% or higher activity, and the humanized antibody #9, the humanized antibody #1, the humanized antibody #0, the human-rabbit chimeric antibody, and the humanized antibody #8 exhibited 25% or higher activity. By contrast, all of the comparative antibodies 1 to 48 exhibited 11% or lower activity, and all of the negative control groups exhibited 5% or lower activity.

For the thyroid cancer cells (TT), the humanized antibody #7, the humanized antibody #10, and the humanized antibody #6 exhibited 42% or higher antitumor effect, the humanized antibody #3, the humanized antibody #4, the humanized antibody #2, and the humanized antibody #5 exhibited 35% or higher activity, and the humanized antibody #9, the humanized antibody #1, the humanized antibody #0, the human-rabbit chimeric antibody, and the humanized antibody #8 exhibited 30% or higher activity. By contrast, all of the comparative antibodies 1 to 48 exhibited 15% or lower activity, and all of the negative control groups exhibited 5% or lower activity.

For the head and neck cancer cells (FaDu), the humanized antibody #7, the humanized antibody #10, and the humanized antibody #6 exhibited 50% or higher antitumor effect, the humanized antibody #3, the humanized antibody #4, the humanized antibody #2, and the humanized antibody #5 exhibited 40% or higher activity, and the humanized antibody #9, the humanized antibody #1, the humanized antibody #0, the human-rabbit chimeric antibody, and the antibody #8 exhibited 35% or higher activity. By contrast, all of the comparative antibodies 1 to 48 exhibited 20% or lower activity, and all of the negative control groups exhibited 8% or lower activity.

These results demonstrated that the humanized antibodies #0 to #10 and the human-rabbit chimeric antibody exhibit a significantly stronger antitumor effect on breast cancer, kidney cancer, pancreatic cancer, colorectal cancer, lung cancer, brain tumor, stomach cancer, uterine cancer, ovary cancer, prostate cancer, bladder cancer, esophagus cancer, leukemia, lymphoma, liver cancer, gallbladder cancer, sarcoma, melanoma, adrenal cortex cancer, Ewing's tumor, Hodgkin's lymphoma, mesothelioma, multiple myeloma, testicle cancer, thyroid cancer, or head and neck cancer than that of the comparative antibodies.

Moreover, the humanized antibodies #0 to #10 and the human-rabbit chimeric antibody exhibited significantly stronger antitumor activity against breast cancer, kidney cancer, pancreatic cancer, colorectal cancer, lung cancer, brain tumor, stomach cancer, uterine cancer, ovary cancer, prostate cancer, bladder cancer, esophagus cancer, leukemia, lymphoma, liver cancer, gallbladder cancer, sarcoma, melanoma, adrenal cortex cancer, Ewing's tumor, Hodgkin's lymphoma, mesothelioma, multiple myeloma, testicle cancer, thyroid cancer, or head and neck cancer as described above than that of all of the antibodies against CAPRIN-1 described in Examples of WO2010/016526, WO2011/096517, WO2011/096528, WO2011/096519, WO2011/096533, WO2011/096534, WO2011/096535, WO2013/018886, WO20131018894, WO2013/018892, WO2013/018891, WO2013/018889, WO2013/018883, WO2013/125636, WO2013/125654, WO2013/125630, WO2013/125640, WO2013/147169, and WO2013/147176.

The antitumor effect was shown as cytotoxic activity against the cancer cell lines that was determined by mixing each antibody against CAPRIN-1, effector cells, and chromium 51-incorporated target cells, culturing the cells for 4 hours, and measuring the amount of chromium 51 released into the medium after the cultivation, followed by calculating according to the following formula*:

Cytotoxic activity (%)=(Amount of chromium 51 released from the target cells when the antibody against CAPRIN-1 and effector cells are added−Amount of chromium 51 naturally released from the target cells)/(Amount of chromium 51 released from the target cells to which 1 N hydrochloric acid is added−Amount of chromium 51 naturally released from the target cells)×100.    *Formula:

Example 6-1: Preparation of Humanized Anti-CAPRIN-1 Monoclonal Antibodies in which Amino Acid in Heavy Chain Constant Region was Substituted Anti-CAPRIN-1 antibodies having a heavy chain constant region described in SEQ ID NO: 33 in which a portion of amino acids in the heavy chain constant region of the humanized antibody #0, #2, #3, #4, #5, #6, #7, #8, #9, or #10 obtained in Example 3 was substituted (hereinafter, referred to as engineered I-type anti-CAPRIN-1 antibodies) were prepared. A DNA encoding the amino acid sequence of a heavy chain having the heavy chain constant region mentioned above and a heavy chain variable region represented by SEQ ID NO: 7 was synthesized, and this was inserted to a vector for expression in mammalian cells according to a routine method. Furthermore, a DNA encoding the amino acids of a light chain variable region represented by SEQ ID NO: 11 was inserted to a vector for expression in mammalian cells having an insert of a gene encoding the light chain constant region of human IgG to prepare a recombinant expression vector. The prepared two recombinant expression vectors were transferred to mammalian cells according to a routine method, and a culture supernatant of engineered I-type anti-CAPRIN-1 antibody #0 of the humanized antibody #0 was obtained. Culture supernatants containing engineered I-type anti-CAPRIN-1 antibodies #1, #2, #3, #4, #5, #6, #7, #8, #9, and #10 described in Example 3 were further obtained in the same way as above as to the humanized antibodies #1, #2, #3, #4, #5, #6, #7, #8, #9, and #10, respectively. The obtained culture supernatants containing the engineered I-type anti-CAPRIN-1 antibodies #0 to #10 were each purified according to a routine method using Hitrap Protein A Sepharose FF (manufactured by GE Healthcare Japan Corp.). The buffer was replaced with PBS(−), and the resultant was filtered through a 0.22 μm filter (manufactured by Merck Millipore Corp.) to prepare the engineered I-type anti-CAPRIN-1 antibodies.

Next, anti-CAPRIN-1 antibodies having a heavy chain constant region described in SEQ ID NO: 34, in which a portion of amino acids in the heavy chain constant region of the humanized antibody #0, #1, #2, #3, #4, #5, #6, #7, #8, #9, or #10 obtained in Example 3 was substituted (hereinafter, referred to as engineered II-type anti-CAPRIN-1 antibodies), were prepared. A DNA encoding the amino acid sequence of a heavy chain having the heavy chain constant region mentioned above and a heavy chain variable region represented by SEQ ID NO: 7 was synthesized, and this was inserted to a vector for expression in mammalian cells according to a routine method. Further, as prepared above, a DNA encoding the amino acids of a light chain variable region represented by SEQ ID NO: 11 was inserted to a vector for expression in mammalian cells having an insert of a gene encoding the light chain constant region of human IgG1 to prepare a recombinant expression vector. These two recombinant expression vectors were transferred to mammalian cells according to a routine method, and a culture supernatant of engineered II-type anti-CAPRIN-1 antibody #0 was obtained. Culture supernatants containing engineered II-type anti-CAPRIN-1 antibodies #1, #2, #3, #4, #5, #6, #7, #8, #9, and #10 described in Example 3, were further obtained in the same way as above as to the humanized antibodies #1, #2, #3, #4, #5, #6, #7, #8, #9, and #10, respectively. The obtained culture supernatants containing the engineered II-type anti-CAPRIN-1 antibodies #0 to #10 were each purified according to a routine method using Hitrap Protein A Sepharose FF (manufactured by GE Healthcare Japan Corp.). The buffer was replaced with PBS(−), and the resultant was filtered through a 0.22 μm filter (manufactured by Merck Millipore Corp.) to prepare the engineered II-type anti-CAPRIN-1 antibodies.

Example 6-2: Preparation of Anti-CAPRIN-1 Antibodies Having Sugar Chain with No Fucose Added to N-Acetylglucosamine at Sugar Chain Reducing End Among all N-Glycoside-Linked Sugar Chains Attached to Heavy Chain Constant Region Next, anti-CAPRIN-1 antibodies having a sugar chain with no fucose added to N-acetylglucosamine at the sugar chain reducing end among all N-glycoside-linked sugar chains attached to the heavy chain constant region of the humanized antibody #0, #1, #2, #3, #4, #5, #6, #7, #8, #9, or #10 obtained in Example 3 (hereinafter, referred to as engineered III-type anti-CAPRIN-1 antibodies) were obtained by the following method: a neomycin resistance gene-containing mammalian cell expression vector harboring a gene of GDP-6-deoxy-D-lyxo-4-hexulose reductase (RMD), which is an enzyme that does not catalyze the reaction of converting GDP-6-deoxy-D-lyxo-4-hexulose to GDP-L-fucose, was transferred to mammalian cell line CHO cells according to a routine method using a transfection reagent FreeStyle™ MAX Reagent (Life Technologies Corp.). The transfected CHO cells were cultured in a medium containing G-418 to prepare a stable pool of CHO cells expressing RMD. From this stable pool, 7 CHO cells constitutively expressing RMD were cloned by the limiting dilution method. The RMD gene expression level in each of the cloned 7 RMD-CHO cells was evaluated three times every other week by quantitative PCR to select CHO cells constitutively and stably expressing the RMD gene (RMD-CHO cells). In the same way as in Example 3, the gene encoding the amino acid sequence of the heavy chain variable region represented by SEQ ID NO: 7 and the gene encoding the amino acids of the light chain variable region represented by SEQ ID NO: 11 were respectively transferred through a vector for expression in mammalian cells having a gene insert of the heavy chain constant region of human IgG1 and a vector for expression in mammalian cells having a gene insert of the light chain constant region of human IgG1 to the RMD-CHO cells constitutively expressing RMD according to a routine method, and a culture supernatant containing engineered III-type anti-CAPRIN-1 antibody #0 was obtained. Culture supernatants containing engineered III-type anti-CAPRIN-1 antibodies #1, #2, #3, #4, #5, #6, #7, #8, #9, and #10 described in Example 3, were further obtained in the same way as above as to the humanized antibodies #1, #2, #3, #4, #5, #6, #7, #8, #9, and #10, respectively. The obtained culture supernatants containing the engineered III-type anti-CAPRIN-1 antibodies #0 to #10 were each purified according to a routine method using Hitrap Protein A Sepharose FF (manufactured by GE Healthcare Japan Corp.). The buffer was replaced with PBS(−), and the resultant was filtered through a 0.22 μm filter (manufactured by Merck Millipore Corp.) to prepare an antibody composition containing the engineered III-type anti-CAPRIN-1 antibody #0. Similarly, antibody purified products containing engineered III-type anti-CAPRIN-1 antibodies #1 to #10 were obtained. The proportion of the anti-CAPRIN-1 antibody having a sugar chain with no fucose added to N-acetylglucosamine at the sugar chain reducing end among all N-glycoside-linked sugar chains attached to the heavy chain constant region, contained in each of these purified antibody compositions was evaluated using LabChip® GXII (PerkinElmer, Inc.) and consequently, was 80% or higher in all cases.

In the same way as in Example 3, the gene encoding the amino acid sequence of the heavy chain variable region represented by SEQ ID NO: 7 and the gene encoding the amino acids of the light chain variable region represented by SEQ ID NO: 11 were respectively transferred through a hygromycin resistance gene-containing vector for expression in mammalian cells having a gene insert of the heavy chain constant region of human IgG1 and a hygromycin resistance gene-containing vector for expression in mammalian cells having a gene insert of the light chain constant region of human IgG1 to the RMD-CHO cells according to a routine method, and the resulting cells were cultured in a medium containing hygromycin B to prepare a stable pool expressing engineered III-type anti-CAPRIN-1 antibody #0. From this stable pool, cells constitutively and stably expressing the engineered III-type anti-CAPRIN-1 antibody #0 were prepared by the limiting dilution method. The proportion of the anti-CAPRIN-1 antibody having a sugar chain with no fucose added to N-acetylglucosamine at the sugar chain reducing end among all N-glycoside-linked sugar chains attached to the heavy chain constant region, contained in each of the purified antibody compositions comprising the engineered III-type anti-CAPRIN-1 antibodies #0 to #10 produced by the respective cells was evaluated using LabChip® GXII (PerkinElmer, Inc.) and consequently, was 80% or higher in all cases.

Example 6-3: Preparation of Anti-CAPRIN-1 Antibodies Having Amino Acid Substitution in Heavy Chain Constant Region and Having Sugar Chain with No Fucose Added to N-Acetylglucosamine at Sugar Chain Reducing End Among all N-Glycoside-Linked Sugar Chains Attached to Heavy Chain Constant Region Next, anti-CAPRIN-1 antibodies having a heavy chain constant region described in SEQ ID NO: 34 in which a portion of amino acids in the heavy chain constant region of the humanized antibody #0, #1, #2, #3, #4, #5, #6, #7, #8, #9, or #10 described in Example 3 was substituted, and having a sugar chain with no fucose added to N-acetylglucosamine at the sugar chain reducing end among all N-glycoside-linked sugar chains attached to the heavy chain constant region of the antibody (hereinafter, referred to as engineered N-type anti-CAPRIN-1 antibodies) were prepared. A DNA encoding the amino acid sequence of a heavy chain having the variant heavy chain constant region prepared in Example 6-1 and the heavy chain variable region of human IgG1 represented by SEQ ID NO: 7 was synthesized and inserted to a vector for expression in mammalian cells according to a routine method, while a DNA encoding the amino acids of a light chain variable region represented by SEQ ID NO: 11 was synthesized and inserted to a vector for expression in mammalian cells having an insert of a gene encoding the amino acids of the light chain constant region of human IgG1, and the resulting vectors were transferred to the RMD-CHO cells constitutively expressing GDP-6-deoxy-D-lyxo-4-hexulose reductase (RMD) prepared in Example 6-2. A culture supernatant of engineered N-type anti-CAPRIN-1 antibody #0 of the humanized antibody #0 was obtained. Culture supernatants containing engineered N-type anti-CAPRIN-1 antibodies #1, #2, #3, #4, #5, #6, #7, #8, #9, and #10 were further obtained in the same way as above as to the humanized antibodies #1, #2, #3, #4, #5, #6, #7, #8, #9, and #10, respectively, described in Example 3. The obtained culture supernatants containing the engineered IV-type anti-CAPRIN-1 antibodies #0 to #10 were each purified according to a routine method using Hitrap Protein A Sepharose FF (manufactured by GE Healthcare Japan Corp.). The buffer was replaced with PBS(−), and the resultant was filtered through a 0.22 μm filter (manufactured by Merck Millipore Corp.) to prepare an antibody composition containing the engineered IV-type anti-CAPRIN-1 antibody #0. Similarly, antibody purified products containing engineered IV-type anti-CAPRIN-1 antibodies #1 to #10 were obtained. The proportion of the anti-CAPRIN-1 antibody having a sugar chain with no fucose added to N-acetylglucosamine at the sugar chain reducing end among all N-glycoside-linked sugar chains attached to the heavy chain constant region, contained in each of these purified antibody compositions was evaluated using LabChip® GXII (PerkinElmer, Inc.) and consequently, was 80% or higher in all cases.

A DNA encoding the amino acid sequence of a heavy chain having the modified heavy chain constant region prepared in Example 6-1 and the heavy chain variable region of human IgG1 represented by SEQ ID NO: 7 was synthesized and inserted to a hygromycin resistance gene-containing vector for expression in mammalian cells according to a routine method, while a DNA encoding the amino acids of a light chain variable region represented by SEQ ID NO: 11 was synthesized and inserted to a hygromycin resistance gene-containing vector for expression in mammalian cells having an insert of a gene encoding the amino acids of the light chain constant region of human IgG1, and the resulting vectors were transferred to the cells. The cells were cultured in a medium containing hygromycin B to prepare a stable pool expressing engineered IV-type anti-CAPRIN-1 antibody #0. From this stable pool, cells constitutively and stably expressing the engineered IV-type anti-CAPRIN-1 antibody #0 were prepared by the limiting dilution method. Cells constitutively and stably expressing engineered IV-type anti-CAPRIN-1 antibodies #1, #2, #3, #4, #5, #6, #7, #8, #9, and #10 were further prepared in the same way as above as to the humanized antibodies #1, #2, #3, #4, #5, #6, #7, #8, #9, and #10 described in Example 3, respectively. The proportion of the anti-CAPRIN-1 antibody having a sugar chain with no fucose added to N-acetylglucosamine at the sugar chain reducing end among all N-glycoside-linked sugar chains attached to the heavy chain constant region, contained in each of the purified antibody compositions containing the engineered IV-type anti-CAPRIN-1 antibodies #0 to #10 produced by the respective cells was evaluated using LabChip® GXII (PerkinElmer, Inc.) and consequently, was 80% or higher in all cases.

Example 7: Antigen Specificity of Engineered-Type Anti-CAPRIN-1 Antibodies and Reactivity Thereof with Cancer Cells The specific reactivity of the engineered I-type anti-CAPRIN-1 antibodies #0 to #10, the engineered II-type anti-CAPRIN-1 antibodies #0 to #10, the respective antibody compositions containing the engineered III-type anti-CAPRIN-1 antibodies #0 to #10, and the respective antibody compositions containing the engineered IV-type anti-CAPRIN-1 antibodies #0 to #10 (hereinafter, referred to as engineered-type anti-CAPRIN-1 antibodies) prepared in Examples 6-1 to 6-3 with the CAPRIN-1 protein was confirmed in the same way as in Example 4. As a result, the absorbance value of the well to which a human IgG antibody confirmed not to react with the CAPRIN-1 protein was added, used as a negative control, was as low as that of the well to which no antibody was added, whereas all of the wells respectively to which the engineered-type anti-CAPRIN-1 antibodies were added exhibited equivalently high absorbance values. All of the engineered-type anti-CAPRIN-1 antibodies in the wells on which the CAPRIN-1 protein was not immobilized merely exhibited an absorbance value equivalent to that of the negative control. From these results, all of the engineered-type anti-CAPRIN-1 antibodies were confirmed to specifically react with the CAPRIN-1 protein.

Next, the reactivity of each engineered-type anti-CAPRIN-1 antibody with various human cancer cells was confirmed in the same way as in Example 4. Breast cancer cells (BT-474 and MDA-MB-361), colorectal cancer cells (HT-29), lung cancer cells (QG56), stomach cancer cells (NCI-N87), uterine cancer cells (HEC-1-A), prostate cancer cells (22Rv1), pancreatic cancer cells (Panc10.5), liver cancer cells (Hep3B), ovary cancer cells (SKOV3), kidney cancer cells (Caki-2), brain tumor cells (U-87MG), bladder cancer cells (T24 and HT-1376), esophagus cancer cells (OE33), leukemia cells (OCI-AML5), lymphoma cells (Ramos), gallbladder cancer cells (TGBC14TKB), fibrosarcoma cells (HT-1080), melanoma cells (G-361), adrenal cortex cancer cells (A-673), Ewing's tumor cells (RD-ES), Hodgkin's lymphoma cells (RPMI11666), mesothelioma cells (NCI-H2452), multiple myeloma cells (IM-9), testicle cancer cells (NT/D1), thyroid cancer cells (TT), and head and neck cancer cells (FaDu) were used in this evaluation. As a result, the fluorescence intensity from each engineered-type anti-CAPRIN-1 antibody was stronger in all of the cancer cells used in the evaluation than that in the case of using the negative control. From these results, all of the engineered-type anti-CAPRIN-1 antibodies were confirmed to specifically react with the CAPRIN-1 protein present on the membrane surface of human cancer cells.

Example 8: Antitumor Activity of Engineered-Type Anti-CAPRIN-1 Antibody Against Various Human Cancer Cells The engineered-type anti-CAPRIN-1 antibodies (the engineered I-type anti-CAPRIN-1 antibodies #0 to #10, the engineered II-type anti-CAPRIN-1 antibodies #0 to #10, the respective antibody compositions containing the engineered III-type anti-CAPRIN-1 antibodies #0 to #10, and the respective antibody compositions containing the engineered IV-type anti-CAPRIN-1 antibodies #0 to #10) prepared in Examples 6-1 to 6-3 were evaluated for their antitumor effects on various human cancer cells on the basis of ADCC activity in the same way as in Example 5. A well to which an isotype control antibody was added, a well to which no antibody was added, and a well to which an antibody reacting with the CAPRIN-1 protein but exhibiting no reactivity with the surface of human cancer cells, on which CAPRIN-1 was expressed, was added were prepared as negative controls. The humanized antibodies #0 to #10, which were the corresponding unengineered anti-CAPRIN-1 antibodies, were used as comparative antibodies. Each antibody was added at 0.01 to 1 μg/mL (final concentration) to V-bottomed 96-well plates.

Breast cancer cells (BT-474 and MDA-MB-361), colorectal cancer cells (HT-29), lung cancer cells (QG56), stomach cancer cells (NCI-N87), uterine cancer cells (HEC-1-A), prostate cancer cells (22Rv1), pancreatic cancer cells (Panc10.5), liver cancer cells (Hep3B), ovary cancer cells (SKOV3), kidney cancer cells (Caki-2), brain tumor cells (U-87MG), bladder cancer cells (T24 and HT-1376), esophagus cancer cells (OE33), leukemia cells (OCI-AML5), lymphoma cells (Ramos), gallbladder cancer cells (TGBC14TKB), fibrosarcoma cells (HT-1080), melanoma cells (G-361), adrenal cortex cancer cells (A-673), Ewing's tumor cells (RD-ES), Hodgkin's lymphoma cells (RPMI1666), mesothelioma cells (NCI-H2452), multiple myeloma cells (IM-9), testicle cancer cells (NT/D1), thyroid cancer cells (TT), and head and neck cancer cells (FaDu) were used as target cells. $10^6$ cells of each human cancer cell line mentioned above were collected into each 50 mL centrifugal tube. 100 μCi of chromium 51 (manufactured by PerkinElmer, Inc.) was added thereto, and the tube was incubated at 37° C. for 1 hour. Then, the cells were washed with an RPMI1640 medium containing 10% FBS three times, added at $2 \times 10^3$ cells/well to the 96-well V-bottomed plates to which each of the antibodies was added, and reacted.

Human NK cells separated from human peripheral blood mononuclear cells by using a routine method were used as effector cells. The human NK cells added at 0.4 to $2.0 \times 10^5$ cells/well to the V-bottomed 96-well plates to which each of the antibodies and the target cells were added and reacted were prepared and reacted at 37° C. for 4 hours under conditions of 5% $CO_2$. After the reaction, 50 μL of a culture supernatant containing chromium 51 released from damaged cancer cells was recovered from each well. The amount of chromium 51 released into the culture supernatant from damaged cancer cells was measured in the same way as in Example 5 to calculate the antitumor effects of the anti-CAPRIN-1 antibodies on the cancer cells.

As a result, for the breast cancer cells (BT-474), the engineered-type anti-CAPRIN-1 antibodies, i.e., the engineered I-type anti-CAPRIN-1 antibodies #0 to #10, the engineered II-type anti-CAPRIN-1 antibodies #0 to #10, the respective antibody compositions containing the engineered III-type anti-CAPRIN-1 antibodies #0 to #10, and the respective antibody compositions containing the engineered IV-type anti-CAPRIN-1 antibodies #0 to #10 each exhibited a stronger antitumor effect than that of the negative controls. The engineered I-type anti-CAPRIN-1 antibodies #0 to #10, the engineered II-type anti-CAPRIN-1 antibodies #0 to #10, and the respective antibody compositions containing the engineered III-type anti-CAPRIN-1 antibodies #0 to #10 exhibited the same level of the antitumor effect as that exhibited by the corresponding unengineered antibodies (humanized antibodies #0 to #10) used as comparative antibodies were approximately 1/13 to 1/20 concentrations of the unengineered antibody concentrations, respectively. In order for the respective antibody compositions containing the engineered IV-type anti-CAPRIN-1 antibodies #0 to #10 to achieve the same level of the antitumor effect as that of the corresponding unengineered antibodies, the concentrations were approximately 1/150 of the unengineered antibody concentrations, respectively. These results demonstrated that the engineered-type anti-CAPRIN-1 antibodies (the engineered I-type anti-CAPRIN-1 antibodies #0 to #10, the engineered II-type anti-CAPRIN-1 antibodies #0 to #10, and the respective antibody compositions containing the engineered III-type anti-CAPRIN-1 antibodies #0 to #10 and the engineered IV-type anti-CAPRIN-1 antibodies #0 to #10) exhibit improved antitumor activity as compared with the corresponding unengineered antibodies. These results also demonstrated that the respective antibody compositions containing the engineered IV-type anti-CAPRIN-1 antibodies #0 to #10 produce a stronger antitumor effect than that of the engineered I-type anti-CAPRIN-1 antibodies #0 to #10, the engineered II-type anti-CAPRIN-1 antibodies #0 to #10, and the respective antibody compositions containing the engineered III-type anti-CAPRIN-1 antibodies #0 to #10.

In addition, a similar stronger antitumor effect was also obtained for the breast cancer cells (MDA-MB-361), the colorectal cancer cells (HT-29), the lung cancer cells (QG56), the stomach cancer cells (NCI-N87), the uterine cancer cells (HEC-1-A), the prostate cancer cells (22Rv1), the pancreatic cancer cells (Panc10.5), the liver cancer cells (Hep3B), the ovary cancer cells (SKOV3), the kidney cancer cells (Caki-2), the brain tumor cells (U-87MG), the bladder cancer cells (T24 and HT-1376), the esophagus cancer cells (OE33), the leukemia cells (OCI-AML5), the lymphoma cells (Ramos), the gallbladder cancer cells (TGBC14TKB), the fibrosarcoma cells (HT-1080), the melanoma cells (G-361), the adrenal cortex cancer cells (A-673), the Ewing's tumor cells (RD-ES), the Hodgkin's lymphoma cells (RPMI1666), the mesothelioma cells (NCI-H2452), the multiple myeloma cells (IM-9), the testicle cancer cells (NT/D1), the thyroid cancer cells (TT), and the head and neck cancer cells (FaDu) used in the evaluation.

INDUSTRIAL APPLICABILITY

The antibody of the present invention is useful for the treatment and/or prevention of a cancer.

All publications, patents, and patent applications cited herein are incorporated herein by reference in their entirety.

The invention claimed is:

1. An antibody or an antigen-binding fragment thereof, which comprises
a heavy chain variable region comprising complementarity-determining regions of SEQ ID NOs: 1, 2, and 3 and
a light chain variable region comprising complementarity-determining regions of SEQ ID NOs: 4, 5, and 6, and
has immunological reactivity with a CAPRIN-1 protein.

2. The antibody or the fragment thereof according to claim 1, wherein
the heavy chain variable region comprises the amino acid sequence of SEQ ID NO: 8, and
the light chain variable region comprises the amino acid sequence of SEQ ID NO: 15.

3. The antibody or the fragment thereof according to claim 1, wherein
the heavy chain variable region comprises the amino acid sequence of SEQ ID NO: 10, and
the light chain variable region comprises the amino acid sequence of SEQ ID NO: 15.

4. The antibody or the fragment thereof according to claim 1, wherein
the heavy chain variable region comprises the amino acid sequence of SEQ ID NO: 7, and
the light chain variable region comprises the amino acid sequence of SEQ ID NO: 15.

5. The antibody or the fragment thereof according to claim 1, wherein
the heavy chain variable region comprises the amino acid sequence of SEQ ID NO: 8, and
the light chain variable region comprises the amino acid sequence of SEQ ID NO: 13.

6. The antibody or the fragment thereof according to claim 1, wherein
the heavy chain variable region comprises the amino acid sequence of SEQ ID NO: 7, and
the light chain variable region comprises the amino acid sequence of SEQ ID NO: 12.

7. The antibody or the fragment thereof according to claim 1, wherein
the heavy chain variable region comprises the amino acid sequence of SEQ ID NO: 8, and
the light chain variable region comprises the amino acid sequence of SEQ ID NO: 12.

8. The antibody or the fragment thereof according to claim 1, wherein
the heavy chain variable region comprises the amino acid sequence of SEQ ID NO: 7, and
the light chain variable region comprises the amino acid sequence of SEQ ID NO: 13.

9. The antibody or the fragment thereof according to claim 1, wherein
the heavy chain variable region comprises the amino acid sequence of SEQ ID NO: 10, and
the light chain variable region comprises the amino acid sequence of SEQ ID NO: 14.

10. The antibody or the fragment thereof according to claim 1, wherein
the heavy chain variable region comprises the amino acid sequence of SEQ ID NO: 8, and
the light chain variable region comprises the amino acid sequence of SEQ ID NO: 11.

11. The antibody or the fragment thereof according to claim 1, wherein
the heavy chain variable region comprises the amino acid sequence of SEQ ID NO: 7, and
the light chain variable region comprises the amino acid sequence of SEQ ID NO: 11.

12. The antibody or the fragment thereof according to claim 1, wherein
the heavy chain variable region comprises the amino acid sequence of SEQ ID NO: 9, and
the light chain variable region comprises the amino acid sequence of SEQ ID NO: 15.

13. The antibody or the fragment thereof according to claim 1, wherein
the heavy chain variable region comprises the amino acid sequence of SEQ ID NO: 20, and
the light chain variable region comprises the amino acid sequence of SEQ ID NO: 21.

14. The antibody or the fragment thereof according to claim 1, wherein the antibody is a human antibody, a humanized antibody, a chimeric antibody, a single-chain antibody, or a multispecific antibody.

15. The antibody or the fragment thereof according to claim 1, wherein the antibody or the fragment is conjugated with an antitumor agent.

16. The antibody according to claim 1, wherein the antibody has a heavy chain constant region and comprises the substitution of one or more amino acids in the heavy chain constant region.

17. The antibody according to claim 1, wherein the antibody is an antibody lacking fucose added to N-acetylglucosamine at the sugar chain reducing end of a N-glycoside-linked sugar chain attached to the heavy chain constant region.

18. An antibody composition comprising:
an antibody wherein the antibody is an antibody lacking fucose added to N-acetylglucosamine at the sugar chain reducing end of a N-glycoside-linked sugar chain attached to the heavy chain constant region, and
an antibody according to claim 1 having fucose added to N-acetylglucosamine at the sugar chain reducing end of a N-glycoside-linked sugar chain attached to the heavy chain constant region.

19. A cell producing an antibody according to claim 17.

20. A pharmaceutical composition for the treatment of a CAPRIN-1-expressing cancer, comprising an antibody or a fragment thereof according to claim 1 as an active ingredient.

21. The pharmaceutical composition according to claim 20, wherein the CAPRIN-1-expressing cancer is breast cancer, kidney cancer, pancreatic cancer, colorectal cancer, lung cancer, brain tumor, stomach cancer, uterine cancer, ovary cancer, prostate cancer, bladder cancer, esophagus cancer, leukemia, lymphoma, liver cancer, gallbladder cancer, sarcoma, mastocytoma, melanoma, adrenal cortex cancer, Ewing's tumor, Hodgkin's lymphoma, mesothelioma, multiple myeloma, testicle cancer, thyroid cancer, or head and neck cancer.

22. A combination drug product for the treatment of a CAPRIN-1-expressing cancer, comprising a pharmaceutical composition according to claim 20 and a pharmaceutical composition comprising an antitumor agent.

23. A DNA encoding an antibody or a fragment thereof according to claim 1.

24. A method for treating a CAPRIN-1-expressing cancer, comprising administering an antibody or a fragment thereof according to claim 1 to a subject.

* * * * *